(12) United States Patent
Cohn et al.

(10) Patent No.: US 12,426,965 B2
(45) Date of Patent: Sep. 30, 2025

(54) IMAGE-GUIDED ROBOTIC ARM FOR INSERTING A PENETRATING MEMBER INTO A BODY LUMEN

(71) Applicant: Obvius Robotics, Inc., Asheville, NC (US)

(72) Inventors: William E. Cohn, Bellaire, TX (US);
Russell Seiber, Asheville, NC (US);
James Patrick Herlihy, Houston, TX (US); Kenneth Wayne Rennicks, Pearland, TX (US); Scott Nortman, Sunrise, FL (US)

(73) Assignee: Obvius Robotics, Inc., Asheville, NC (US)

( * ) Notice: Subject to any disclaimer, the term of this patent is extended or adjusted under 35 U.S.C. 154(b) by 219 days.

(21) Appl. No.: 18/210,257

(22) Filed: Jun. 15, 2023

(65) Prior Publication Data
US 2024/0415585 A1    Dec. 19, 2024

(51) Int. Cl.
*A61B 34/30* (2016.01)
*A61B 17/34* (2006.01)
(Continued)

(52) U.S. Cl.
CPC .......... *A61B 34/30* (2016.02); *A61B 17/3401* (2013.01); *A61B 46/10* (2016.02);
(Continued)

(58) Field of Classification Search
CPC ..... A61B 34/30; A61B 17/3401; A61B 46/10; A61B 90/361; A61B 2034/301;
(Continued)

(56) References Cited

U.S. PATENT DOCUMENTS

| | | |
|---|---|---|
| 4,428,748 A | 1/1984 | Peyman et al. |
| 4,527,569 A | 7/1985 | Kolb |
| | (Continued) | |

FOREIGN PATENT DOCUMENTS

| | | |
|---|---|---|
| CA | 2999060 | 3/2017 |
| CA | 2729803 | 8/2017 |
| | (Continued) | |

OTHER PUBLICATIONS

Adebar, Troy K. et al., 3-D Ultrasound-Guided Robotic Needle Steering in Biological Tissue, IEEE Trans Biomed Eng, Dec. 2014, 61(12):2899-2910.
(Continued)

*Primary Examiner* — Masud Ahmed
(74) *Attorney, Agent, or Firm* — Pandiscio & Pandiscio

(57) ABSTRACT

An image-guided robotic system for advancing a penetrating member into a body lumen located beneath a skin surface of a patient, the image-guided robotic system comprising: a detector for obtaining data representative of a location of the body lumen beneath the skin surface of the patient; a robotic arm comprising: a penetrating member; a linear actuator for linearly advancing the penetrating member into the body lumen; a vibrational actuator for vibrating the penetrating member at a selected frequency; a processor in communication with the detector, the linear actuator and the vibrational actuator, the processor being configured to: (i) receive the data representative of the location of the body lumen from the detector; (ii) calculate the distance to a preselected target point within the body lumen; (iii) transmit linear advancement instructions to the linear actuator to linearly advance the penetrating member through the skin surface, through tissue between the skin surface and the body lumen and into the preselected target point within the body lumen, wherein the linear advancement instructions comprise the (Continued)

speed and distance required for the linear actuator to advance the penetrating member through the skin surface, through tissue between the skin surface and the body lumen and into the body lumen at the preselected target point within the body lumen; (iv) transmit vibrational instructions to the vibrational actuator to vibrate the penetrating member; and (v) automatically modify at least one of the linear advancement instructions and the vibrational instructions in order to account for resistance encountered by the penetrating member during advancement of the penetrating member through the skin surface, through the tissue between the skin surface and the body lumen and into the preselected target point within the body lumen, wherein at least one of the linear advancement instructions and the vibrational instructions is modified to mitigate deformation of the body lumen as the penetrating member advances through the skin surface, through tissue between the skin surface and the body lumen and into the preselected target point within the body lumen.

21 Claims, 46 Drawing Sheets

(51) Int. Cl.
A61B 46/10 (2016.01)
A61B 90/00 (2016.01)
(52) U.S. Cl.
CPC ...... *A61B 90/361* (2016.02); *A61B 2034/301* (2016.02); *A61B 2034/305* (2016.02)
(58) Field of Classification Search
CPC ...... A61B 2034/305; A61B 2017/3409; A61B 2017/3413; A61B 2090/378; A61B 17/3403; A61B 34/76
See application file for complete search history.

(56) References Cited

U.S. PATENT DOCUMENTS

| | | |
|---|---|---|
| 4,553,541 A | 11/1985 | Burns |
| 4,623,335 A | 11/1986 | Jackson |
| 4,648,406 A | 3/1987 | Miller |
| 4,771,660 A | 9/1988 | Yacowitz |
| 4,801,293 A | 1/1989 | Jackson |
| 4,911,161 A | 3/1990 | Schechter |
| 5,024,662 A | 6/1991 | Menes et al. |
| 5,095,910 A | 3/1992 | Powers |
| 5,221,282 A | 6/1993 | Wuchinich |
| 5,320,613 A | 6/1994 | Houge |
| 5,403,276 A | 4/1995 | Schechter et al. |
| 5,449,370 A | 9/1995 | Vaitekunas |
| 5,471,102 A | 11/1995 | Becker et al. |
| 5,526,820 A | 6/1996 | Khoury |
| 5,575,789 A | 11/1996 | Bell et al. |
| 5,647,373 A | 7/1997 | Palteli |
| 5,647,851 A | 7/1997 | Pokras |
| 5,681,283 A | 10/1997 | Brownfield |
| 5,711,302 A | 1/1998 | Lampropoulos |
| 5,728,089 A | 3/1998 | Lal et al. |
| 5,728,130 A | 3/1998 | Ishikawa et al. |
| 5,729,077 A | 3/1998 | Newnham et al. |
| 5,735,813 A | 4/1998 | Lewis |
| 5,769,086 A | 6/1998 | Ritchart |
| 5,840,026 A | 11/1998 | Uber, III et al. |
| 5,865,764 A | 2/1999 | Moorhead |
| 5,871,470 A | 2/1999 | McWha |
| 5,885,226 A | 3/1999 | Rubinstein et al. |
| 5,954,701 A | 9/1999 | Matalon |
| 6,019,775 A | 2/2000 | Sakurai |
| 6,019,776 A | 2/2000 | Preissman et al. |
| 6,068,604 A | 5/2000 | Krause et al. |
| 6,096,004 A | 8/2000 | Meglan et al. |
| 6,190,333 B1 | 2/2001 | Valencia |
| 6,245,028 B1 | 6/2001 | Furst et al. |
| 6,273,861 B1 | 8/2001 | Bates et al. |
| 6,379,371 B1 | 4/2002 | Novak et al. |
| 6,402,769 B1 | 6/2002 | Boukhny |
| 6,423,014 B1 | 7/2002 | Churchill et al. |
| 6,443,910 B1 | 9/2002 | Krueger et al. |
| 6,465,936 B1 | 10/2002 | Knowles et al. |
| 6,491,708 B2 | 12/2002 | Madan et al. |
| 6,497,714 B1 | 12/2002 | Ishikawa et al. |
| 6,514,267 B2 | 2/2003 | Jewett |
| 6,602,229 B2 | 8/2003 | Coss |
| 6,623,429 B2 | 9/2003 | Percival et al. |
| 6,629,922 B1 | 10/2003 | Puria |
| 6,664,712 B2 | 12/2003 | Rayner |
| 6,673,086 B1 | 1/2004 | Hofmeier et al. |
| 6,689,087 B2 | 2/2004 | Pal et al. |
| 6,718,196 B1 | 4/2004 | Mah et al. |
| 6,726,698 B2 | 4/2004 | Cimino |
| 6,730,043 B2 | 5/2004 | Krueger et al. |
| 6,785,572 B2 | 8/2004 | Yanof et al. |
| 6,817,973 B2 | 11/2004 | Merril et al. |
| 6,869,439 B2 | 3/2005 | White et al. |
| 6,939,317 B2 | 9/2005 | Zacharias |
| 6,942,677 B2 | 9/2005 | Nita et al. |
| 6,984,220 B2 | 1/2006 | Wuchinich |
| 7,018,343 B2 | 3/2006 | Plishka |
| 7,025,774 B2 | 4/2006 | Freeman et al. |
| 7,206,626 B2 | 4/2007 | Quaid, III |
| 7,297,131 B2 | 11/2007 | Nita |
| 7,328,064 B2 | 2/2008 | Mathiesen et al. |
| 7,335,997 B2 | 2/2008 | Wiener |
| 7,364,567 B2 | 4/2008 | Beyerlein |
| 7,374,544 B2 | 5/2008 | Freeman et al. |
| 7,518,479 B2 | 4/2009 | Mask et al. |
| 7,585,280 B2 | 9/2009 | Wilson |
| 7,618,409 B2 | 11/2009 | Hochman |
| 7,648,468 B2 | 1/2010 | Boecker et al. |
| 7,651,475 B2 | 1/2010 | Angel et al. |
| 7,651,490 B2 | 1/2010 | Boukhny et al. |
| 7,654,825 B2 | 2/2010 | Ray |
| 7,776,027 B2 | 8/2010 | Manna et al. |
| 7,896,833 B2 | 3/2011 | Hochman |
| 7,922,689 B2 | 4/2011 | Lechner |
| 7,955,301 B1 | 6/2011 | McKay |
| 8,043,229 B2 | 10/2011 | Mulvihill et al. |
| 8,043,308 B2 | 10/2011 | Bittenson |
| 8,075,496 B2 | 12/2011 | Deck |
| 8,142,365 B2 | 3/2012 | Miller |
| 8,177,753 B2 | 5/2012 | Vitullo et al. |
| 8,231,645 B2 | 7/2012 | List |
| 8,308,741 B2 | 11/2012 | Hyde et al. |
| 8,328,738 B2 | 12/2012 | Frankhouser et al. |
| 8,777,871 B2 | 7/2014 | Frankhouser et al. |
| 8,870,865 B2 | 10/2014 | Frankhouser et al. |
| 8,945,011 B2 | 2/2015 | Sheldon et al. |
| 8,951,195 B2 | 2/2015 | Sheldon et al. |
| 8,992,439 B2 | 3/2015 | Mulvihill et al. |
| 9,033,880 B2 | 5/2015 | Sheldon et al. |
| 9,220,483 B2 | 12/2015 | Frankhouser et al. |
| 9,408,571 B2 | 8/2016 | Gilgunn et al. |
| 9,420,992 B2 | 8/2016 | Sheldon et al. |
| 9,427,207 B2 | 8/2016 | Sheldon et al. |
| 9,763,661 B2 * | 9/2017 | Zergiebel ............ A61B 17/068 |
| 9,861,739 B2 * | 1/2018 | Sheldon ............... A61B 8/4209 |
| 9,987,468 B2 * | 6/2018 | Bagwell ........... A61B 5/150389 |
| 9,999,440 B2 | 6/2018 | Sheldon et al. |
| 10,052,458 B2 | 8/2018 | Fischer et al. |
| 10,219,832 B2 | 3/2019 | Bagwell et al. |
| 11,648,070 B2 | 5/2023 | Wilson et al. |
| 2001/0014785 A1 | 8/2001 | Sussman et al. |
| 2002/0010390 A1 | 1/2002 | Guice |
| 2002/0026127 A1 | 2/2002 | Balbierz et al. |
| 2002/0042594 A1 | 4/2002 | Lum |
| 2002/0049462 A1 | 4/2002 | Friedman |
| 2002/0077589 A1 | 6/2002 | Tessari |
| 2002/0109433 A1 | 8/2002 | Rayner |

(56) References Cited

U.S. PATENT DOCUMENTS

| | | |
|---|---|---|
| 2002/0156376 A1 | 10/2002 | Wang et al. |
| 2002/0183774 A1 | 12/2002 | Witt et al. |
| 2002/0198555 A1 | 12/2002 | White et al. |
| 2003/0040737 A1 | 2/2003 | Merril |
| 2003/0078495 A1 | 4/2003 | Goodwin |
| 2003/0109871 A1 | 6/2003 | Johnson et al. |
| 2003/0195468 A1 | 10/2003 | Lal et al. |
| 2003/0199899 A1 | 10/2003 | Boecker et al. |
| 2003/0199909 A1 | 10/2003 | Boecker |
| 2003/0233046 A1 | 12/2003 | Ferguson |
| 2004/0010204 A1 | 1/2004 | Weber |
| 2004/0010251 A1 | 1/2004 | Pitaru |
| 2004/0024358 A1 | 2/2004 | Meythaler |
| 2004/0049216 A1 | 3/2004 | Verdaasdonk |
| 2004/0059285 A1 | 3/2004 | Mathiesen |
| 2004/0082884 A1 | 4/2004 | Pal |
| 2004/0106894 A1 | 6/2004 | Hunter et al. |
| 2004/0215080 A1 | 10/2004 | Lechner |
| 2004/0260240 A1 | 12/2004 | Beyerlein |
| 2005/0070458 A1 | 3/2005 | John |
| 2005/0131345 A1 | 6/2005 | Miller |
| 2005/0148940 A1 | 7/2005 | Miller |
| 2005/0177201 A1 | 8/2005 | Freeman |
| 2006/0058783 A1 | 3/2006 | Buchman, III |
| 2006/0122555 A1 | 6/2006 | Hochman |
| 2006/0129091 A1 | 6/2006 | Bonnette et al. |
| 2006/0135882 A1 | 6/2006 | Bleich |
| 2006/0142657 A1 | 6/2006 | Quaid et al. |
| 2006/0149141 A1 | 7/2006 | Sheets |
| 2006/0149161 A1 | 7/2006 | Wilson et al. |
| 2006/0195043 A1 | 8/2006 | Rutherford et al. |
| 2006/0224144 A1 | 10/2006 | Lee |
| 2007/0038129 A1 | 2/2007 | Kishimoto et al. |
| 2007/0063618 A1 | 3/2007 | Bromfield |
| 2007/0079455 A1 | 4/2007 | Brewer et al. |
| 2007/0088297 A1 | 4/2007 | Redding |
| 2007/0088376 A1 | 4/2007 | Zacharias |
| 2007/0123888 A1 | 5/2007 | Bleich et al. |
| 2007/0129628 A1 | 6/2007 | Hirsh |
| 2007/0129732 A1 | 6/2007 | Zacharias |
| 2007/0142766 A1 | 6/2007 | Sundar et al. |
| 2007/0191758 A1 | 8/2007 | Hunter et al. |
| 2007/0219496 A1 | 9/2007 | Kamen et al. |
| 2007/0250113 A1 | 10/2007 | Hegeman et al. |
| 2007/0255220 A1 | 11/2007 | King et al. |
| 2008/0009791 A1 | 1/2008 | Cohen et al. |
| 2008/0021490 A1 | 1/2008 | Briggs et al. |
| 2008/0031413 A1 | 2/2008 | Bouvier et al. |
| 2008/0055028 A1 | 3/2008 | Mask et al. |
| 2008/0097287 A1 | 4/2008 | Nelson et al. |
| 2008/0103413 A1 | 5/2008 | Cicenas et al. |
| 2008/0139961 A1 | 6/2008 | Slama et al. |
| 2008/0147094 A1 | 6/2008 | Bittenson |
| 2008/0154188 A1 | 6/2008 | Hochman |
| 2008/0228104 A1 | 9/2008 | Uber et al. |
| 2008/0255444 A1 | 10/2008 | Li |
| 2009/0005703 A1 | 1/2009 | Fasciano |
| 2009/0030339 A1 | 1/2009 | Cheng et al. |
| 2009/0069712 A1 | 3/2009 | Mulvihill et al. |
| 2009/0131830 A1 | 5/2009 | Freeman et al. |
| 2009/0131832 A1 | 5/2009 | Sacristan Rock et al. |
| 2009/0157044 A1 | 6/2009 | Liyanagama et al. |
| 2009/0204119 A1 | 8/2009 | Bleich et al. |
| 2009/0240205 A1 | 9/2009 | Wen |
| 2009/0247865 A1 | 10/2009 | Spohn et al. |
| 2009/0270759 A1 | 10/2009 | Wilson et al. |
| 2009/0275823 A1 | 11/2009 | Ayati et al. |
| 2010/0004558 A1 | 1/2010 | Frankhouser et al. |
| 2010/0010505 A1 | 1/2010 | Herlihy et al. |
| 2010/0036245 A1 | 2/2010 | Yu et al. |
| 2010/0036256 A1 | 2/2010 | Boukhny et al. |
| 2010/0069828 A1 | 3/2010 | Steen et al. |
| 2010/0069851 A1 | 3/2010 | Vad et al. |
| 2010/0094143 A1 | 4/2010 | Mahapatra et al. |
| 2010/0094310 A1 | 4/2010 | Warring et al. |
| 2011/0004159 A1 | 1/2011 | Nelson et al. |
| 2011/0125107 A1 | 5/2011 | Slocum et al. |
| 2011/0130758 A9 | 6/2011 | Bleich et al. |
| 2011/0224623 A1 | 9/2011 | Velez Rivera |
| 2011/0298628 A1 | 12/2011 | Vad et al. |
| 2012/0078231 A1 | 3/2012 | Hoshinouchi |
| 2012/0210569 A1 | 8/2012 | Schmitt |
| 2012/0220942 A1 | 8/2012 | Hall et al. |
| 2012/0232488 A1 | 9/2012 | Aviles |
| 2012/0259221 A1 | 10/2012 | Sheldon et al. |
| 2013/0072856 A1 | 3/2013 | Frankhouser et al. |
| 2013/0107569 A1 | 5/2013 | Suganuma |
| 2013/0131502 A1 | 5/2013 | Blaivas et al. |
| 2013/0172713 A1 | 7/2013 | Kirschenman |
| 2014/0005667 A1 | 1/2014 | Stulen et al. |
| 2014/0142553 A1 | 5/2014 | Poncon |
| 2014/0221968 A1 | 8/2014 | Ransbury et al. |
| 2014/0299568 A1 | 10/2014 | Browne |
| 2015/0065916 A1 | 3/2015 | Maguire et al. |
| 2015/0182232 A1 | 7/2015 | Peterson et al. |
| 2015/0216557 A1 | 8/2015 | Mulvihill et al. |
| 2015/0297449 A1 | 10/2015 | Browne et al. |
| 2015/0306358 A1 | 10/2015 | Duffy et al. |
| 2016/0317242 A1 | 11/2016 | Herlihy et al. |
| 2017/0188990 A1 | 7/2017 | Von Allmen et al. |
| 2018/0256862 A1 | 9/2018 | Bagwell et al. |
| 2018/0325547 A1 | 11/2018 | Bagwell et al. |
| 2018/0368883 A1 | 12/2018 | Rossa et al. |
| 2020/0253670 A1 | 8/2020 | Doisneau et al. |
| 2020/0261113 A1* | 8/2020 | Bagwell ............... A61B 8/4488 |
| 2020/0405403 A1* | 12/2020 | Shelton, IV ....... A61B 17/3421 |
| 2021/0045711 A1 | 2/2021 | Brattain et al. |

FOREIGN PATENT DOCUMENTS

| | | |
|---|---|---|
| CA | 2967482 | 11/2017 |
| EP | 0266058 | 5/1988 |
| EP | 1647255 | 4/2006 |
| JP | 9239031 | 9/1997 |
| JP | 2001346874 | 12/2001 |
| JP | 2012035010 | 2/2012 |
| JP | 2013172549 | 9/2013 |
| WO | WO 2004091693 | 10/2004 |
| WO | WO 2008086560 | 7/2008 |
| WO | WO 2008097609 | 8/2008 |
| WO | WO 2009083600 | 7/2009 |
| WO | WO 2009092164 | 7/2009 |
| WO | WO 2009097621 | 8/2009 |
| WO | WO 2010006335 | 1/2010 |
| WO | WO 2012109621 | 8/2012 |
| WO | WO 2014066937 | 5/2014 |
| WO | WO 2015037418 | 3/2015 |

OTHER PUBLICATIONS

American College of Surgeons, Revised Statement on Recommendations for Use of Real-Time Ultrasound Guidance for Placement of Central Venous Catheters, Statements from the college, https://www.facs.org/about-acs/statements/60-real-timeultrasound#sthash.fTgorRkl.dpuf, online Feb. 1, 2011.

Backlund, Brandon H. et al., Ultrasound Guidance for Central Venous Access by Emergency Physicians in Colorado, Western Journal of Emergency Medicine, Sep. 2012, pp. 320-325, vol. XIII, No. 4.

Begg, ND, et al., Audible Frequency Vibration of Puncture-Access Medical Devices. Medical Eng Phys 2014; 36:371-7.

Bernard, Robert W. et al., Subclavian Vein Catheterizations: A Prospective Study: I. Non-Infectious Complications, Annals of Surgery, Feb. 1971, pp. 184-190, vol. 173, No. 2.

Castelvecchi, D., This Bite Won't Hurt a Bit-Science News. Science News 2008: 11.

CDC, Guidelines for the Prevention of Intravascular Catheter-Related Infections, 2011, http://stacks.cdc.gov/view/cdc/5916/.

Chan, K.K., et al., The Mode of Action of Surgical Tissue Removing Devices, IEEE 1985 Ultrasonics Symposium, Oct. 1985. 16-18, 1985, p. 855-9.

(56) References Cited

OTHER PUBLICATIONS

Cleary, K. et al., Image-Guided Robotic Delivery System for Precise Placement of Therapeutic Agents, JJ. Controlled Release, 2001, vol. 74, No. 1, pp. 363-368.
Cohen, D., This Won't Hurt a Bit. New Scientist, 2002:21.
Dario, et al., Smart Surgical Tools and Augmenting Devices, IEEE Transactions on Robotics and Automation, vol. 19, No. 5, Oct. 2003, pp. 782-792.
Defalque, Ray J., M.D., Percutaneous Catheterization of the Internal Jugular Vein, Anesthesia and Analgesia, Jan.-Feb. 1974, pp. 116-121, vol. 53, No. 1.
Dodge, Kelly L., MD, et al., Use of Ultrasound Guidance Improves Central Venous Catheter Insertion Success Rates Among Junior Residents, Journal of Ultrasound Medicine, 2012, 31: 1519-26.
Elgezua, et al., Survey on Current State-of-the-Art in Needle Insertion Robots: Open Challenges for Application in Real Surgery, ProCedia CIRP 5 (2013) 94-99, Elsevier, Amsterdam, Netherlands.
European Patent Office, Communication Pursuant to Article 94(3) EPC, Communication from European Application No. 16847434.4; pp. 1-9, publisher European Patent Office, published Munich Germany, copyright and dated Apr. 17, 2019; copy enclosed (9 pages).
Froehlich, Curt D et al., Ultrasound-guided central venous catheter placement decreases complications and decreases placement attempts compared with the landmark technique in patients in a pediatric intensive care unit, Crit Care Med, 2009, pp. 1090-1096, vol. 37, No. 3.
Goethals, P., Tactile Feedback for Robot Assisted Minimally Invasive Surgery: An Overview, Division PMA, Department of Engineering, K.U. Leuven, Jul. 14, 2008.
Hind, Daniel et al., Ultrasonic locating devices for central venous cannulation: meta-analysis, BMJ, Aug. 16, 2003, pp. 1-7, vol. 327:361.
Hing, et al., Reality-Based Estimation of Needle and Soft-Tissue Interaction for Accurate Haptic Feedback in Prostate Brachytherapy Simulation, Program for Robotics, Intelligent Sensing, and Mechatronics (PRISM) Labaoratory, Drexel University, Philadelphia, PA, Drexel University College of Medicine, Philadelphia, PA.
Hing, et al., Reality-Based Needle Insertion Simulation for Haptic Feedback in Prostate Brachytherapy, Proceedings of the 2006 IEEE International Conference on Robotics and Automation, Orlando, Florida, May 2006.
Huang, Y., et al., A Piezoelectric Vibration-Based Syringe for Reducing Insertion Force, IOP Conference Series: Materials Science and Engineering, 2012, 42:012020.
International Preliminary Report on Patentability for PCT Application No. PCT/AU2008/000019, dated Jul. 21, 2009.
International Search Report for PCT Application No. PCT/US2009/060387, dated May 18, 2010.
International Search Report for PCT Application No. PCT/US2009/056864, dated Apr. 26, 2010.
International Searching Authority; International Search Report and Written Opinion of the International Searching Authority; International Application No. PCT/US2016/041499; Patent Cooperation Treaty; pp. 1-8; publisher United States International Searching Authority; Published Alexandria, Virginia, US; copyright and dated Oct. 20, 2016; copy enclosed (8 pages).
International Searching Authority; International Search Report and Written Opinion of the International Searching Authority; International Application No. PCT/US2016/052228; Patent Cooperation Treaty; pp. 1-9; publisher United States International Searching Authority; Published Alexandria, Virginia, US; copyright and dated Dec. 20, 2016; copy enclosed (9 pages).
International Searching Authority; International Search Report and Written Opinion of the International Searching Authority;International Application No. PCT/US2014/062099; Patent Cooperation Treaty; pp. 1-10; publisher United States International Searching Authority; Published Alexandria Virginia, US; copyright and mailing date Mar. 11, 2015; copy enclosed (9 pages).
Khalaji, I., et al., Analysis of Needle-Tissue Friction During Vibration-Assisted Needle Insertion, Intelligent Robots and Systems (IROS), 2013 IEEE/RSJ International Conference on; Nov. 3-7, 2013, 2013, pp. 4099-4104.
Kong, XQ, et al., Mosquito Proboscis: An Elegant Biomicroelectromechanical System. Phys Rev E Stat Nonlin Soft Matter Phys 2010, 82:011910.
Krell, Kenneth, MD, Critical care workforce, Crit Care Med, 2008, pp. 1350-1353, vol. 36, No. 4.
Kwon, et al., Realistic Force Reflection in the Spine Biopsy Simulator, IEEE International Conference on Robotics and Automation, 2001. Proceedings 2001 ICRA, May 21-26, 2001, Seoul, Korea 2001, vol. 2, 1358-1363.
Lal, A., Silicon-Based Ultrasonic Surgical Actuators, Member, IEEE; Proceedings of the 20th Annual International Conference of the IEEE Engineering in Medicine and Biology Society, vol. 20, No. 6, 1998, pp. 2785-2790.
Loeffel, et al., Development of an Advanced Injection Device for Highly Viscous Materials, European Cells and Materials, vol. 11, Supp. 1, 2006, p. 51.
Luis, J., et al., Rectangular Cymbal Arrays for Improved Ultrasonic Transdermal Insulin Delivery, J. Acoust. Soc. Am., vol. 122, Issue 4, Oct. 2007.
Mahvash, M., et al., Fast Needle Insertion to Minimize Tissue Deformation and Damage. IEEE International Conference on Robotics and Automation 2009: 3097-102.
Mahvash, M., et al., Mechanics of Dynamic Needle Insertion into a Biological Material. IEEE Trans Biomed Eng 2009.
Mark V ProVis Angiographic Injection System, Medrad, Inc., Copyright 2006-2010.
Marx, J.A., et al., The Effect of Vibration on the Needle Dynamics of Sclerotherapy, Australian College of Phlebology, 12th Annual Scientific Meeting, 2008; Gold Coast, Australia.
McGee David C., M.D et al., Preventing Complications of Central Venous Catheterization, The New England Journal of Medicine, Mar. 20, 2003, pp. 1123-1133, 348;12.
Meyer, Jr., R.J., et al., Displacement Amplification of Electroactive Materials Using the Cymbal Flextensional Transducer, Sensors and Actuators A 87 (2001) 157-162.
Muralidliaran, K., Mechanics of Soft Tissue Penetration By a Vibrating Needle, Baltimore, Maryland, University of Maryland Baltimore County, 2007.
Okazawa, Stephen et al., Hand-Held Steerable Needle Device, IEEE/ ASME Transactions on Mechatronics, Jun. 2005, vol. 10, Issue 3.
Piccin, et al., "A Robotized Needle Insertion Device for Percutaneous Procedures", Proceedings of IDETC/CIE 2005, 2006 ASME International Design Engineering Technical Conferences and Computers and Information in Engineering Conference, Long Beach, CA, USA, Sep. 24-28, 2005.
Podder, T.K., et al., Effects of Velocity Modulation During Surgical Needle Insertion, Proceedings of the 2005 IEEE, Engineering in Medicine and Biology 27th Annual Conference, Sep. 1-4, 2005.
Proceedings of The First Phantom Users Research Symposium, May 21-22, 1999, Deutsches Krebsfordschungszentrum, Heidelberg, Germany.
R&D 100 Awards Winners Reveal 21st Century Technologies, 38th Annual R&D Awards, R&D Research & Development, Sep. 2000, p. 135.
Ramasubranianian, MK, et al., Mechanics of a Mosquito Bite With Applications to Microneedle Design. Raleigh, NC 27695-7810, USA, North Carolina State University, 2008.
Randolph, Adrienne G. MD, et al., Ultrasound guidance for placement of central venous catheters: A meta-analysis of the literature, Crit Care Med, Dec. 1996, pp. 2053-2058, 24.
Rothschild, Jeffrey M., MD, MPH, Ultrasound Guidance of Central Vein Catheterization, On Making Health Care Safer: A Critical Analysis of Patient Safety Practices. Rockville, MD: AHRQ, Publications; 200 I; Chapter 21: 245-255, https://archive.aluq.gov/clinic/ ptsafety/chap2 1 .htm.
Schweber, Bill, Medical Design, Medical "Vampire" Robot Seeks Human Vein, Inserts Needle, Sucks Blood, Jul. 30, 2020, https://

(56) References Cited

OTHER PUBLICATIONS www.machinedesign.com/medical-design/article/21137988/medical-vampire-robot-seeks-human-vein-inserts-needle-sucks-blood.

Seldinger, Sven Ivar, Catheter Replacement of the Needle in Percutaneous Arteriography: A new technique, Acta Radiologica, 1953, pp. 368-376, 39:5.

Shin-Ei T, et al., Reduction of Insertion Force of Medical Devices Into Biological Tissues By Vibration, Japm1ese Journal of Medical Electronics and Biological Engineering, (2001) 39:292-296 (with English translation).

Sznajder, J. I., et al., Central Vein Catheterization. Failure and Complication Rates by Three Percutaneous Approaches, Arch. Intern. Med., 1986, pp. 259-261, 146.

Terrett, et al., 3538 Study Assessing the Effectiveness of a Vibrating Dental Syringe Attachment, Pain Management, Oral Pathology, Malodor, and Indices, Mar. 13, 2004.

United States Patent and Trademark Office; Office Action; Office Action from U.S. Appl. No. 13/222,363;copyright and dated Dec. 11, 2014; pp. 1-9; publisher United States Patent and Trademark Office; Published Alexandria, Virginia, USA; copyright and dated Dec. 11, 2014; (9 pages).

United States Patent and Trademark Office; Office Action; Office Action from U.S. Appl. No. 14/329,177; copyright and dated Nov. 18, 2014; pp. 1-19; publisher United States Patent and Trademark Office; Published Alexandria, Virginia, USA; copyright and dated Nov. 18, 2014; copy enclosed (19 pages).

United States Patent and Trademark Office; Office Action; Office Action from U.S. Appl. No. 15/205,357; pp. 1-16; publisher United States Patent and Trademark Office;published Alexandria, Virginia, USA; copyright and dated Dec. 13, 2016; copy enclosed (16 pages).

United States Patent and Trademark Office; Office Action; Office Action from U.S. Appl. No. 15/205,357; pp. 1-48; publisher United States Patent and Trademark Office;published Alexandria, Virginia, USA; copyright and dated Jun. 22, 2017; copy enclosed (48 pages).

Van Gerwen, D.J., et al., Needle-Tissue Interaction Forces-A Survey of Experimental Data. Med Eng Phys 2012; 34:665-80.

Visiontech Partners, 2020, Xact Medical Uses Robotics to "Stick" Patients and Wants You to Join Them, http://visiontech-partners.corn/blog/xact-medical-uses-robotics-to-stick-patients-and-wants-you-to-join-thern/.

Xact Medical, Inc., 2018, https://xactmedical.corn/.

Yang, M., et al., Microneedle Insertion Force Reduction Using Vibratory Actuation. Biomed Microdevices, 2004, 6: 177-182, Kluwer Academic Publishers, The Netherlands.

Yonei, Akitomo, M.D. et al., Real-time Ultrasonic Guidance for Percutaneous Puncture of the Internal Jugular Vein, Anesthesiology, Jun. 1986, pp. 830-831, vol. 64, No. 6.

Zevallos, N. et al., Toward Robotically Automated Femoral Vascular Access, ArXiv, Jul. 6, 2021.

Zorcolo, et al., "Catheter Insertion Simulation with Combined Visual and Haptic Feedback", Center for Advanced Studies, Research and Development in Sardinia, 09101 Uta (CA) Italy.

* cited by examiner (TOP VIEW)

(FRONT VIEW)

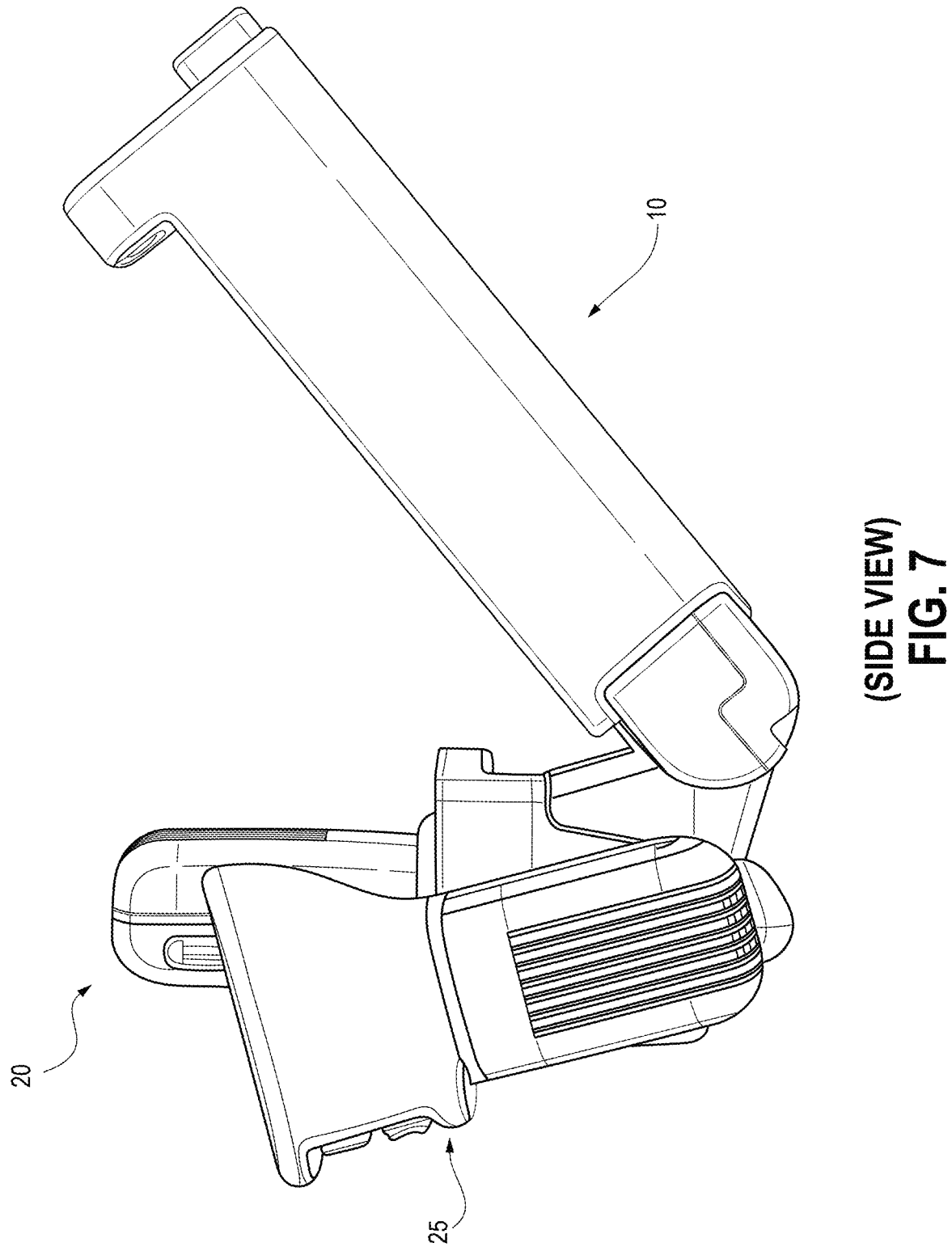

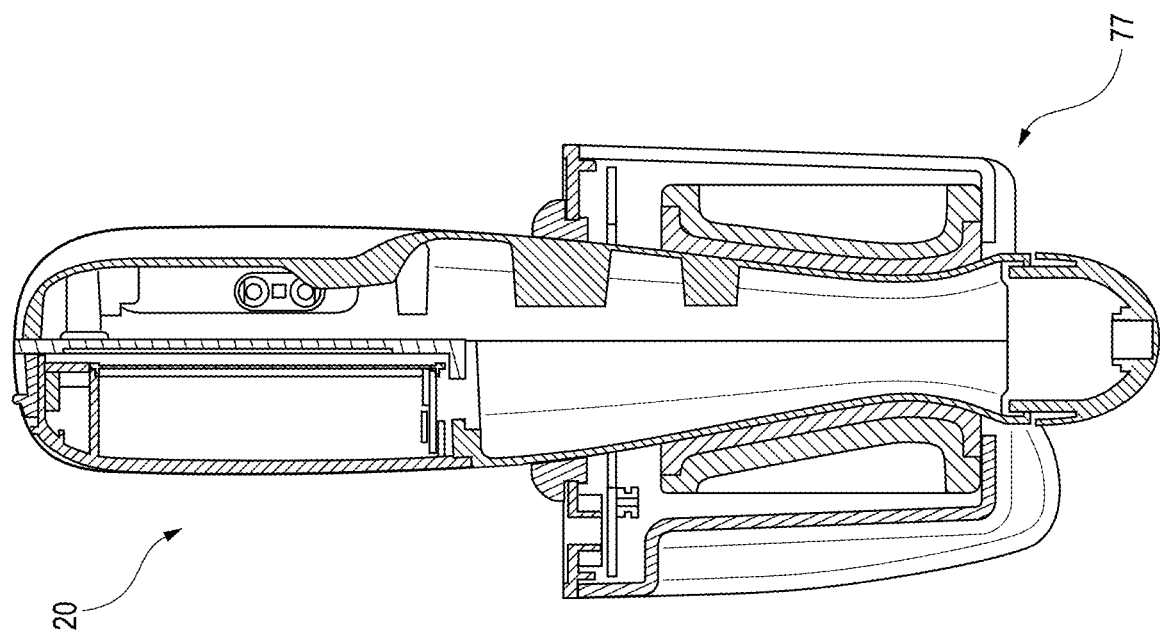
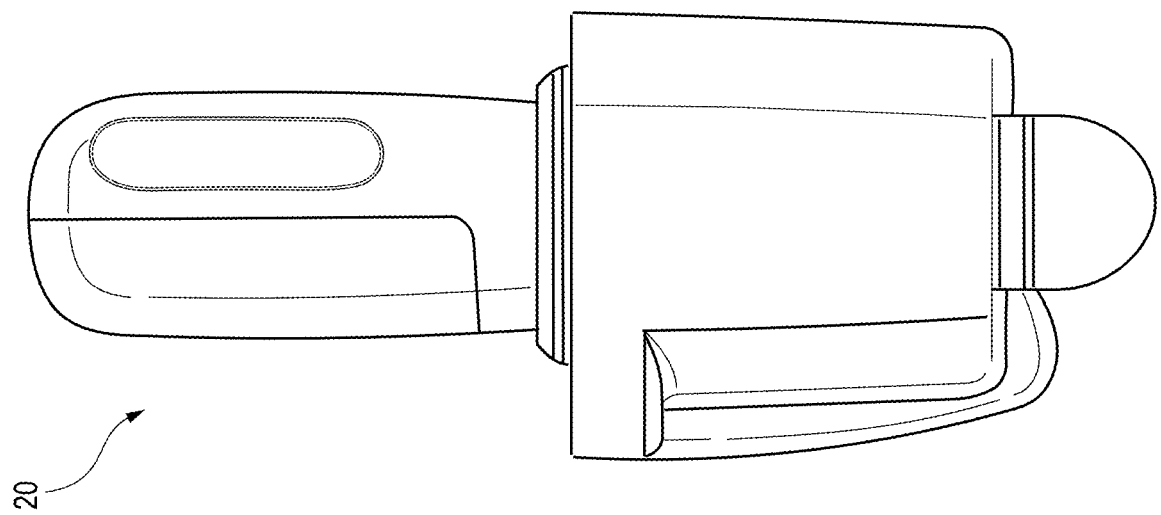
FIG. 8

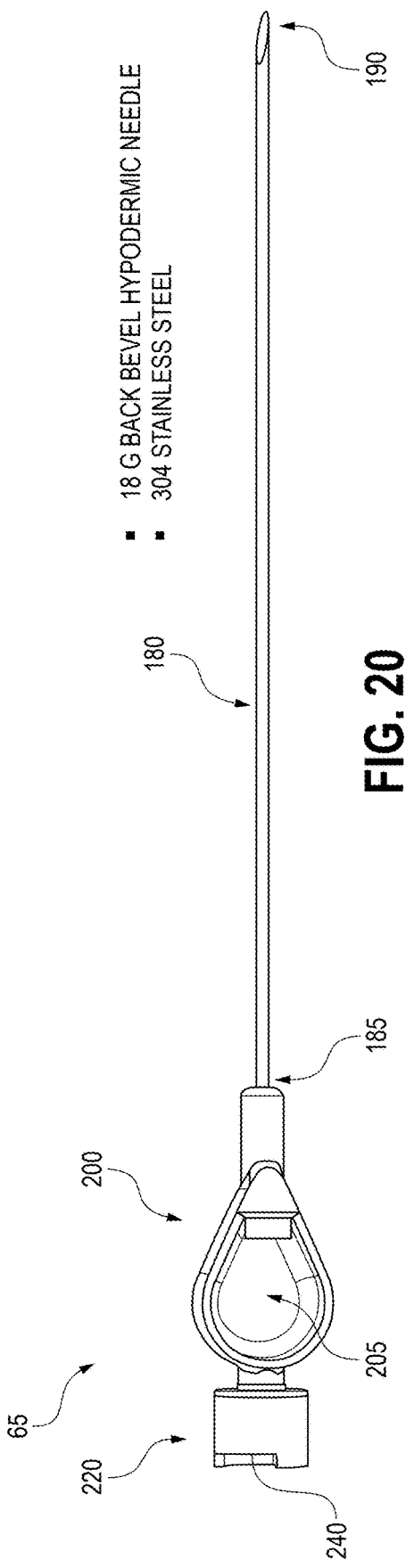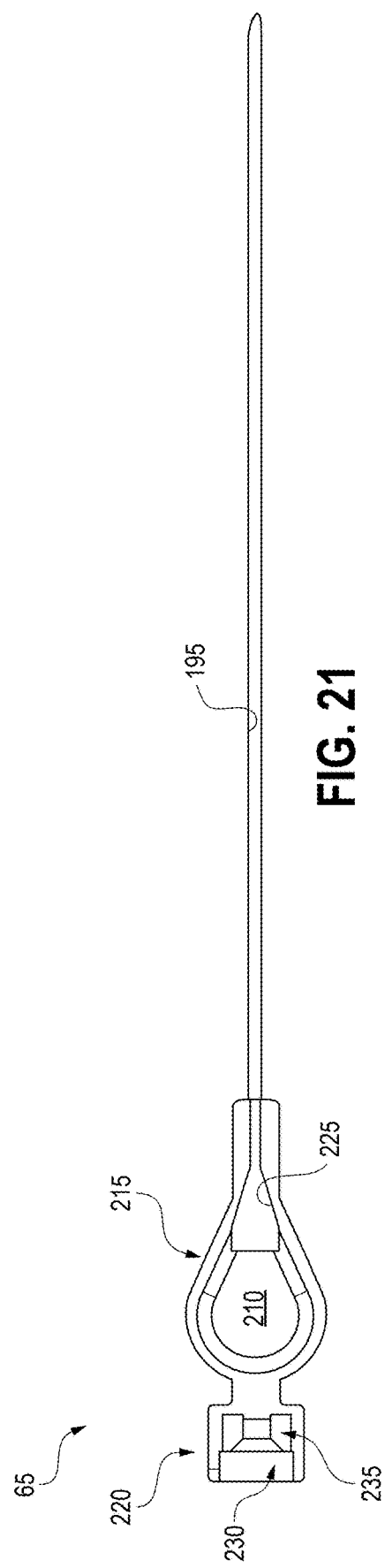

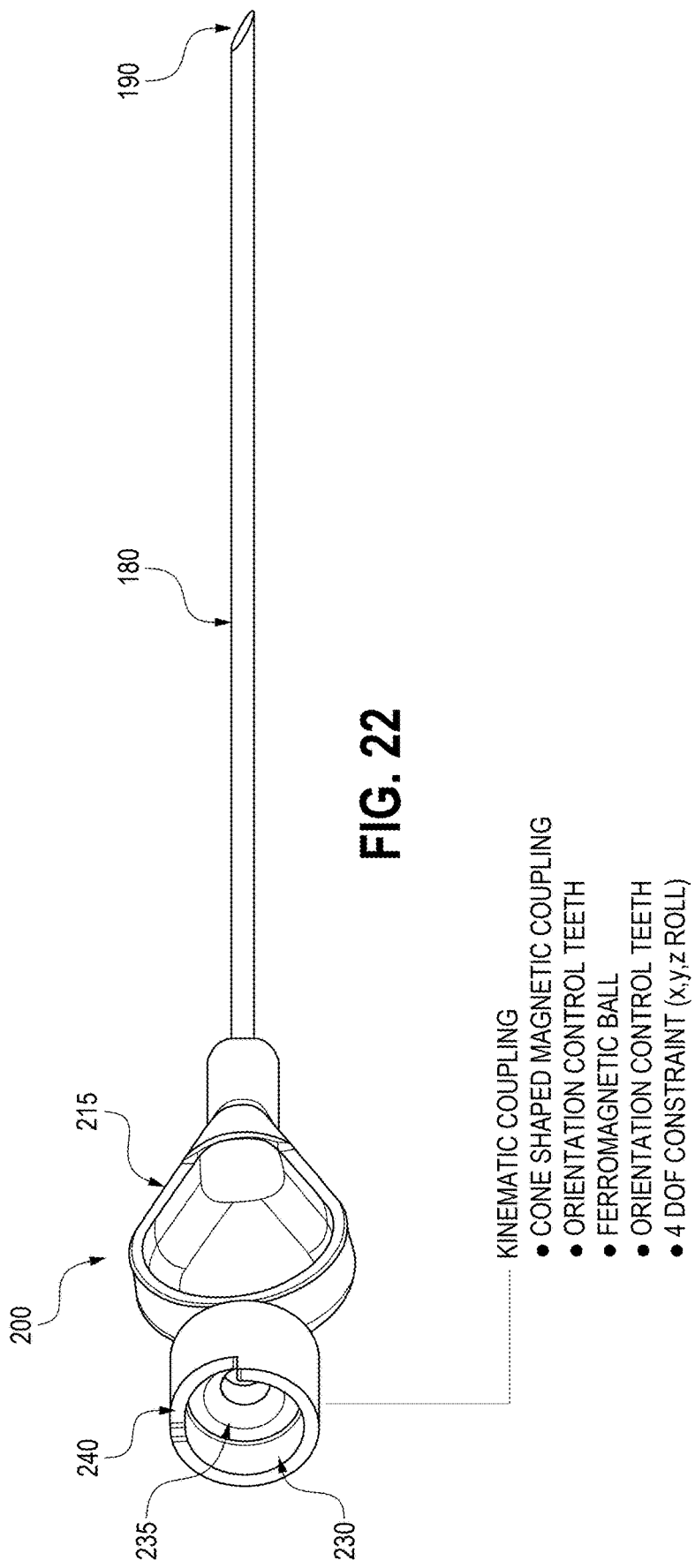

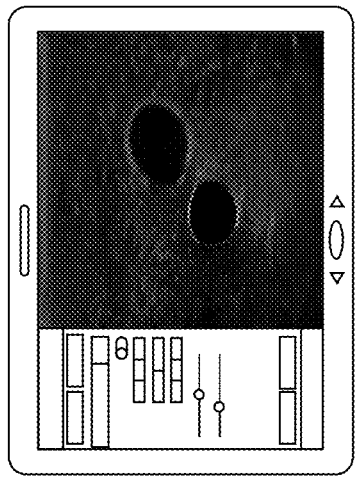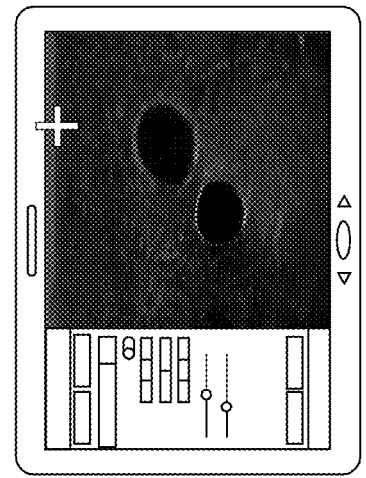
EXEMPLARY ULTRASOUND IMAGE DISPLAY
GUI OVERLAY: OVERLAY WINDOWS (ALLOWS CUSTOM LAYOUTS, INCLUDING POINTER OVER EXISTING APPLICATIONS)
FIG. 33

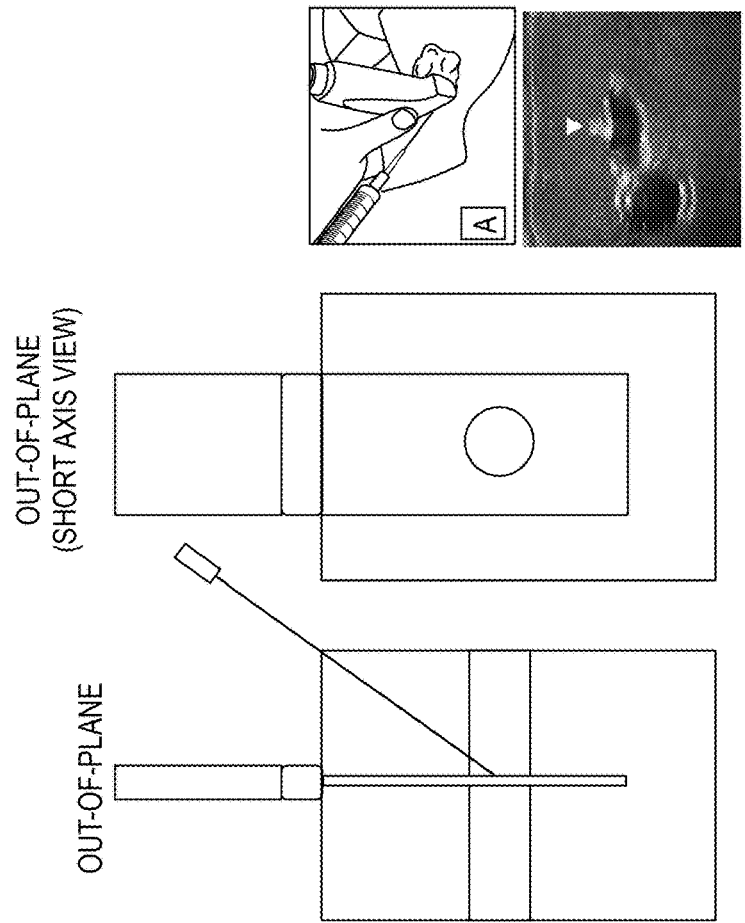

IMAGE-GUIDED ROBOTIC ARM FOR INSERTING A PENETRATING MEMBER INTO A BODY LUMEN

FIELD OF THE INVENTION

The present invention relates to a novel method and robotic arm for penetrating tissue within a body lumen in order to effect the delivery or removal of bodily fluids, tissues, nutrients, medicines, therapies, in general, and more particularly, to a novel method and robotic arm for obtaining percutaneous access to body lumens (e.g., vasculature, spinal cavity) in order to effect the secondary placement of medical devices (e.g., guidewires, catheters, etc.).

BACKGROUND OF THE INVENTION

Central venous catheters (CVCs) are commonly used by physicians to gain access to a vein (e.g., the right subclavian vein) of a patient or to gain access to other hollow anatomical structures. More than 5 million CVCs are placed each year in the United States. A CVC placed in a large vein of a patient is a key platform from which to launch a multitude of critical medical interventions for acutely ill patients, and for patients requiring major surgeries or procedures. By way of example but not limitation, CVCs are often used to administer medication or fluids that the patient is unable to take orally, to obtain access to perform certain blood tests (e.g., central venous oxygen saturation), to administer large volume blood or fluid for resuscitation, to measure central venous pressure, etc.

The intensive care units (ICUs) of U.S. hospitals log over 15 million CVC days (i.e., the total number of days of exposure to CVCs among all patients in the selected population during the selected time period) per year, and 48% of ICU patients have a CVC inserted at some point during their ICU stay. A CVC is also necessary for patients requiring urgent hemodialysis, such as in acute kidney failure, plasma exchange for various immune mediated diseases, multiple forms of chemotherapy for cancer patients, parenteral nutrition for patients whose gastrointestinal tract cannot be used for feeding, and many other medical interventions.

CVC placement has, since the 1950s, been performed using the eponymous technique developed by the Swedish Radiologist Sven-Ivar Seldinger. Using this technique a hollow bore needle, also referred to as an introducer needle, is advanced through a patient's skin and subcutaneous tissue and finally into a central vein, located millimeters to centimeters below the skin surface. The "central veins" are the internal jugular, subclavian, and femoral veins. Once the central vein is entered, a guidewire is manually placed through the hollow bore needle and into the vein. The needle is then removed, and often a plastic co-axial tissue dilator is then run over the wire into the vein, then removed, also over the wire. This dilates the tissue around the guidewire, and allows smooth passage of a CVC, which is installed by placing the CVC over the guidewire and advancing it distally into the vein until the distal end of the CVC is in fluidic connection with the internal lumen of the vein. Once the CVC is in place, the guidewire is removed, leaving the distal end of the CVC inside the internal lumen of the vein, with the proximal end of the CVC disposed exterior to the patient's skin and the CVC passing through the skin and the tissue between the internal lumen of the vein and the exterior surface of the skin.

Since the development of the Seldinger technique, the standard guide used for determining where to place the introducer needle through the skin has been the patient's skin surface anatomy. Veins are usually located millimeters to centimeters below the skin, in specific relationship to certain surface landmarks like bones or muscles. However, CVC placement using surface anatomy landmarks has led to unacceptable failure rates, and the rates of serious complications such as arterial puncture, laceration, and pneumothorax or "collapsed lung" are reported to be as high as 35% and 21%, respectively. These failure rates are attributed to the fact that surface anatomy does not reliably correspond to the location of the deep central veins in every patient. In 1986, ultrasonography (US) began to be used to visualize veins below the skin surface and such images began to be used to more accurately guide the manual placement of CVCs. The use of ultrasonography lowered the failure and complication rates for placement of CVCs to 5-10%. However, ultrasound guided CVC placement technique requires significant training and experience in order for the clinician to perform the procedure reliably. As such, general and cardiovascular surgeons, anesthesiologists, critical care specialists, and interventional radiologists are typically required to effect placement of these catheters. Unfortunately, these specialists are often not available for placement of a CVC in the urgent or emergent time frame in which CVCs are frequently required.

Even well trained, experienced clinicians can fail at unacceptable rates when attempting to place a CVC due to factors that are not possible to account for, or which are beyond their control, given the current state of insertion technique. Two significant factors that can lead to failure when attempting to place a CVC are tissue deformity and venous wall deformation.

By way of example but not limitation, when the introducer needle is pushed through the skin and subcutaneous tissues, the force of the needle on the tissue can cause the central vein that is being targeted to move from its original position, causing what is referred to as a "needle pass miss."

By way of further example but not limitation, when the introducer needle contacts the side wall of a hollow structure (e.g., the venous wall), the needle can push the vein into a different position, an effect sometimes referred to as "rolling" or "off center", again potentially resulting in needle pass miss. Needle pass misses can result in the needle hitting other vital structures located in the vicinity of the central vein that is being accessed (e.g., arteries, lungs, or nerves) and can result in serious complications.

By way of still further example but not limitation, when the introducer needle contacts the side wall of a hollow structure (e.g., the venous wall), the hollow structure can be compressed by the distally-directed force of the needle itself, causing the vein to collapse, and making it nearly impossible for the needle to enter the vessel lumen by piercing the side wall of the hollow structure such that the tip of the needle ends up disposed inside the interior of the lumen. In such a situation, the needle often passes completely through the far side wall of the vessel after crossing the lumen of the vessel, an event sometimes referred to as "back-walling" or "pop through". Back walling (or pop through) often results in bleeding into the peri-venous tissue. Not only is bleeding a notable complication in and of itself, but bleeding also disrupts local anatomy, usually precluding subsequent successful CVC placement.

Thus, there is a need for a new and improved method and apparatus for advancing a penetrating member (e.g., a needle) into a body lumen of a patient, such that the penetrating member minimizes tissue deformation during advancement of the penetrating member through the skin and underlying tissue of the patient, whereby a targeted body lumen (e.g., a vein) will not be moved during advancement of a penetrating member.

Furthermore, it will also be appreciated that when a CVC is installed into a large blood vessel (e.g., the right subclavian vein), it is necessary for the clinician to carefully manage the sterile area of the needle insertion in order to avoid introducing microorganisms into the area of the blood vessel (which may otherwise cause a severe infection).

Where the needle is mounted to a robotic arm or other stationary/moveable object, a sterile drape is often used to cover the stationary/movable object or to cover the patient in the area where the procedure is to be performed. Such a system may be configured so that the needle passes directly through the sterile drape, however, it is possible for the surface of the drape to become contaminated (e.g., via handling of the drape by the clinician). Where such contamination exists, the needle can become contaminated by contacting microorganisms on a surface of the drape as the needle passes through the drape, and the needle may carry those microorganisms into the tissue of the patient as it enters into the patient, causing infection.

Thus, there is a need for a sterile drape which is disposed over the stationary/movable object and/or the patient in a manner which does not require the needle to pass through the sterile drape.

Additionally, and as noted above, CVCs are often utilized to install comparatively large-bore tubing (e.g., to provide for rapid blood infusion, fluid infusion, etc.). To this end, and as noted above, a guidewire is often utilized in combination with one or more tissue dilators in order to prepare an appropriate "tunnel" through the tissue between the surface of the patient's skin and the vessel pierced by the needle. Such a task requires the guidewire to be inserted into the bore of the needle from the proximal end of the needle and advanced distally. The preferably small bore of the needle makes insertion of a guidewire into the bore challenging even for experienced clinicians.

Thus, there is a need for a needle guide which can be used to pass a guidewire through the proximal end of the needle.

In addition, where a needle is to be utilized in combination with, for example, a robotic arm or other stationary/movable device, the needle is typically a disposable component that needs to be removed and replaced prior to each procedure that is to be performed. Such a needle may be secured to a stationary object (e.g., a syringe) by a luer-lock mechanism, however, such a securement mechanism makes it difficult for the clinician to quickly and efficiently remove the needle and replace it between procedures. Also, it may be desirable in such an application for the clinician to have control over the rotational disposition of the needle once it is mounted to the stationary object, and a luer-lock connection does not facilitate automatically and easily controlling the rotational disposition of the installed needle.

Thus, there is a need for a needle connection which facilitates replacement of a needle between procedures.

Finally, in a situation in which an introducer needle is to be advanced using a mechanized system (e.g., a robotic arm, etc.) that automates a portion of the clinician's task of advancing the needle, it is important to provide safety mechanisms to prevent inadvertent advancing of the needle, to monitor the system during use, and to provide a mechanism to calibrate the system prior to use.

Thus, there is a need for a new and improved method and apparatus for advancing a penetrating member (e.g., a needle) through the skin of a patient and into a body lumen (e.g., a vein) of a patient which reduces the incidence of complications inherent in prior art approaches.

SUMMARY OF THE INVENTION

The present invention comprises the provision and use of a novel method and apparatus for advancing a penetrating member (e.g., a needle) through the skin of a patient and into a body lumen (e.g., a vein) of a patient which reduces the incidence of complications inherent in prior art approaches.

In one preferred form of the invention, there is provided an image-guided robotic system for advancing a penetrating member into a body lumen located beneath a skin surface of a patient, the image-guided robotic system comprising:

a detector for obtaining data representative of a location of the body lumen beneath the skin surface of the patient;

a robotic arm comprising:

a penetrating member;

a linear actuator for linearly advancing the penetrating member into the body lumen;

a vibrational actuator for vibrating the penetrating member at a selected frequency;

a processor in communication with the detector, the linear actuator and the vibrational actuator, the processor being configured to:

(i) receive the data representative of the location of the body lumen from the detector;

(ii) calculate the distance to a preselected target point within the body lumen;

(iii) transmit linear advancement instructions to the linear actuator to linearly advance the penetrating member through the skin surface, through tissue between the skin surface and the body lumen and into the preselected target point within the body lumen, wherein the linear advancement instructions comprise the speed and distance required for the linear actuator to advance the penetrating member through the skin surface, through tissue between the skin surface and the body lumen and into the body lumen at the preselected target point within the body lumen;

(iv) transmit vibrational instructions to the vibrational actuator to vibrate the penetrating member; and (v) automatically modify at least one of the linear advancement instructions and the vibrational instructions in order to account for resistance encountered by the penetrating member during advancement of the penetrating member through the skin surface, through the tissue between the skin surface and the body lumen and into the preselected target point within the body lumen, wherein at least one of the linear advancement instructions and the vibrational instructions is modified to mitigate deformation of the body lumen as the penetrating member advances through the skin surface, through tissue between the skin surface and the body lumen and into the preselected target point within the body lumen.

In another preferred form of the invention, there is provided a method for advancing a penetrating member into a body lumen located beneath a skin surface of a patient, the method comprising:

obtaining data representative of a location of a preselected target point within the body lumen;

calculating a distance to the preselected target point within the body lumen;

advancing the penetrating member through the skin surface, through tissue between the skin surface and the body lumen and into the preselected target point within the body lumen; and vibrating the penetrating member during advancement of the penetrating member through the skin surface, through tissue between the skin surface and the body lumen and into the preselected target point within the body lumen;

wherein at least one of speed of distal advancement of the penetrating member and frequency of vibration are modified during advancement of the penetrating member through the skin surface, through tissue between the skin surface and the body lumen and into the preselected target point within the body lumen in order to mitigate deformation of the body lumen as the penetrating member advances through the skin surface, through tissue between the skin surface and the body lumen and into the preselected target point within the body lumen.

In another preferred form of the invention, there is provided a needle comprising:

a shaft comprising a proximal end, a pointed distal end, and a lumen extending therebetween; and a teardrop-shaped cavity disposed at the proximal end of the shaft, the teardrop-shaped cavity being in fluid communication with the lumen.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 2-12 are schematic views showing further details of the novel image-guided robotic system of FIG. 1;

FIGS. 20-22 are schematic views showing a novel needle formed in accordance with the present invention;

FIGS. 32-34 are schematic views showing aspects of novel software for use with the novel image-guided robotic system of the present invention;

FIGS. 54 and 55 are schematic views showing exemplary ultrasound image planes of a body lumen located beneath the skin surface of a patient;

DESCRIPTION OF THE INVENTION

Figure 1:
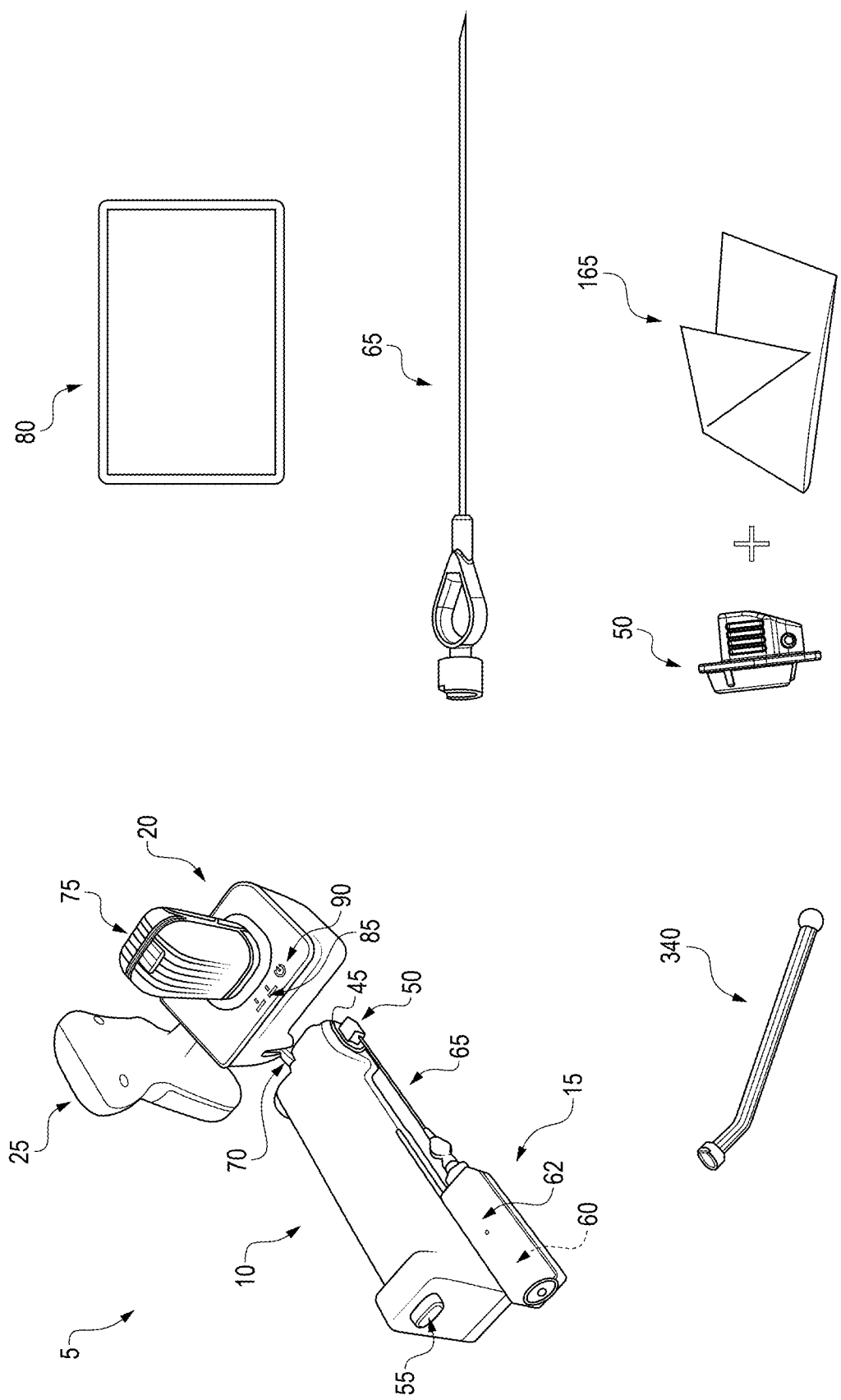
FIG. 1 is a schematic view showing a novel image-guided robotic system for advancing a penetrating member into a body lumen, formed in accordance with the present invention.
Figure 2:
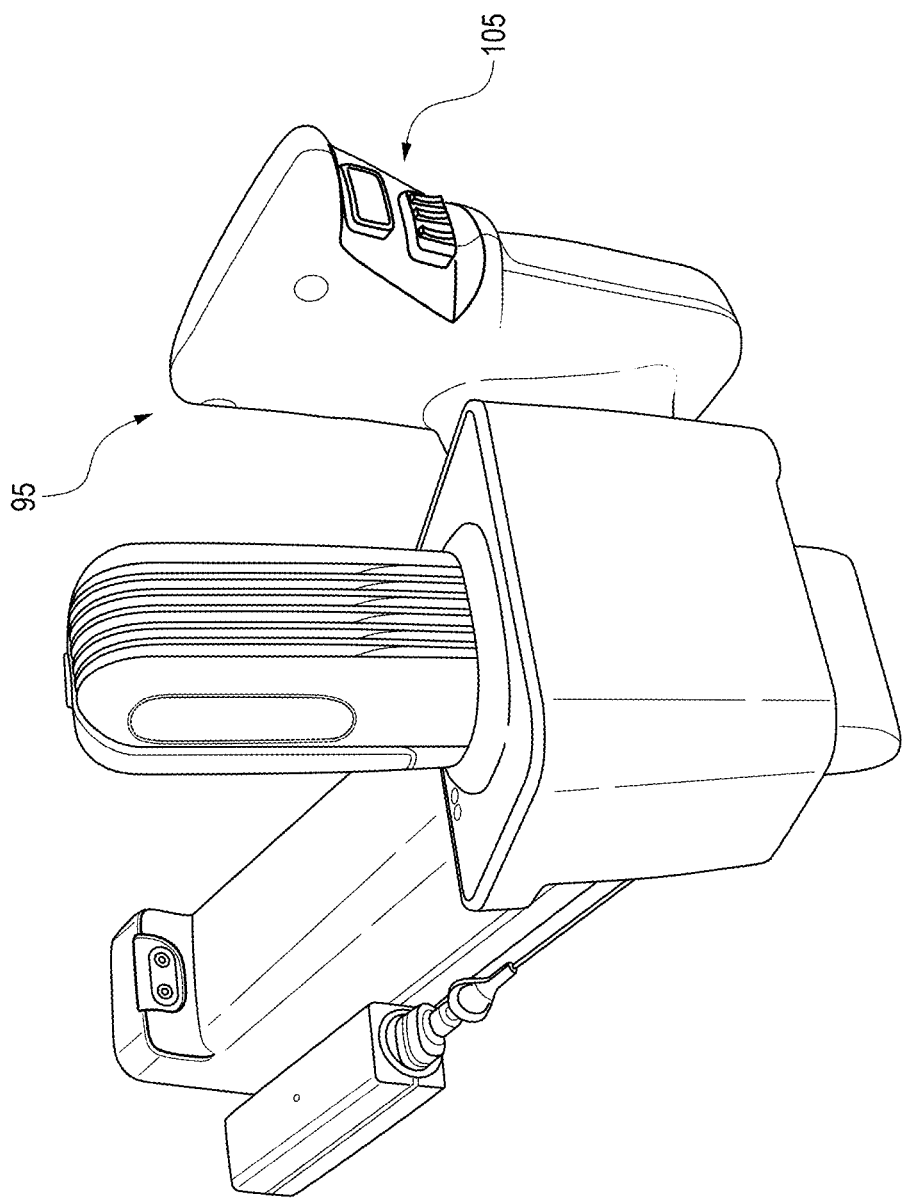
Figure 3:
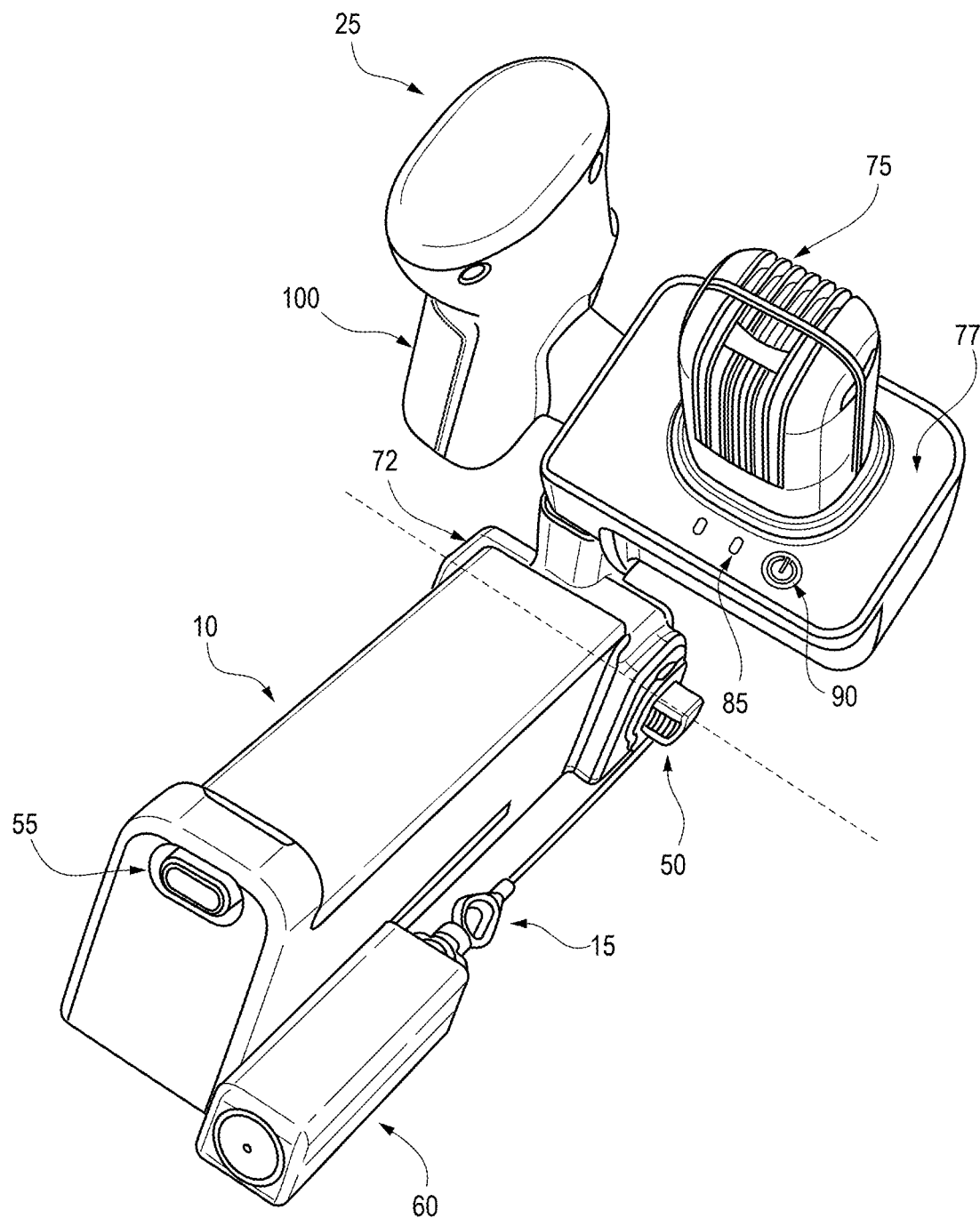

The present invention comprises the provision and use of a novel method and apparatus for advancing a penetrating member (e.g., a needle) through the skin of a patient and into a lumen (e.g., a vein) of the patient which reduces the incidence of complications inherent in prior art approaches.

Overview

Looking at FIGS. 1-9, there is shown a novel hand-held apparatus 5 for advancing a penetrating member (e.g., a needle) through the skin of a patient and into a body lumen (e.g., a vein) of the patient.

Apparatus 5 generally comprises a linear actuator 10, a needle assembly 15, an ultrasound device 20, and a handle 25.

Linear actuator 10 generally comprises a housing 30, a linear actuator motor 35 (e.g., a stepper motor) for selectively moving a needle carriage 40 (FIG. 10) linearly, a needle guide seat 45 for releasably mounting a needle guide 50 to housing 30 and a manual brake release 55 for permitting selective adjustment of the angle of linear actuator 10 relative to ultrasound device 20, as will hereinafter be discussed in further detail.

Needle assembly 15 generally comprises a housing 62 mounted to needle carriage 40 of linear actuator 10, a needle assembly motor 60 for vibrating needle assembly 15, and a needle 65 detachably mounted to housing 62 of needle assembly 15.

Ultrasound device 20 is disposed within a clamping shell 77, which clamping shell 77 is rotatably mounted to linear actuator 10 via a rotary link 70, such that the angle of linear actuator 10 (and hence, the angle of needle assembly 15 mounted thereto) relative to ultrasound device 20 may be selectively adjusted by a clinician, as will hereinafter be discussed in further detail. Rotary link 70 preferably comprises a rotary angle sensor 72 (FIG. 3) for sensing the rotational disposition of linear actuator 10 relative to ultrasound device 20, as will hereinafter be discussed in further detail. Ultrasound device 20 comprises an ultrasound probe 75 which is configured to use high-frequency sound in order to perform ultrasound imaging (sometimes referred to as sonography) in a manner that will be apparent to one of ordinary skill in the art in view of the present disclosure. In one preferred form of the invention, ultrasound device 20 is configured to wirelessly transmit imaging data from ultrasound probe 75 to an electronic device 80 (e.g., a tablet, smartphone, external display, etc.), whereby to display an image of the anatomy imaged by ultrasound probe 75 to the clinician, as will hereinafter be discussed in further detail. If desired, ultrasound device 20 may comprise one or more visual indicators 85 (e.g., LED lights) for displaying the status of apparatus 5, and/or one or more control elements 90 (e.g., buttons, switches, etc.) for controlling apparatus 5, as will hereinafter be discussed in further detail.

Handle 25 generally comprises a grip 95 and a power source 100 (e.g., a removable battery) for powering electronic components of apparatus 5. Grip 95 preferably includes one or more control elements 105 (e.g., buttons) to permit a clinician to operate apparatus 5, as will hereinafter be discussed in further detail.

Linear Actuator 10

Figure 10:
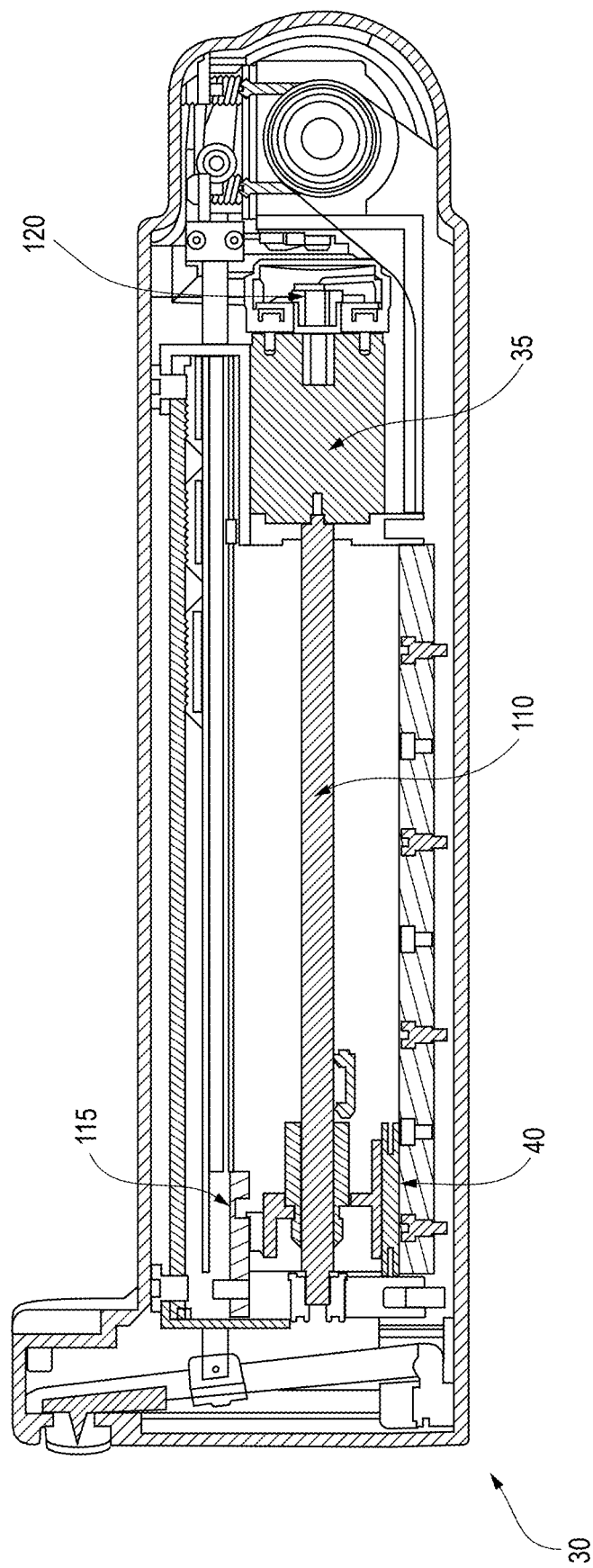
Figure 11:
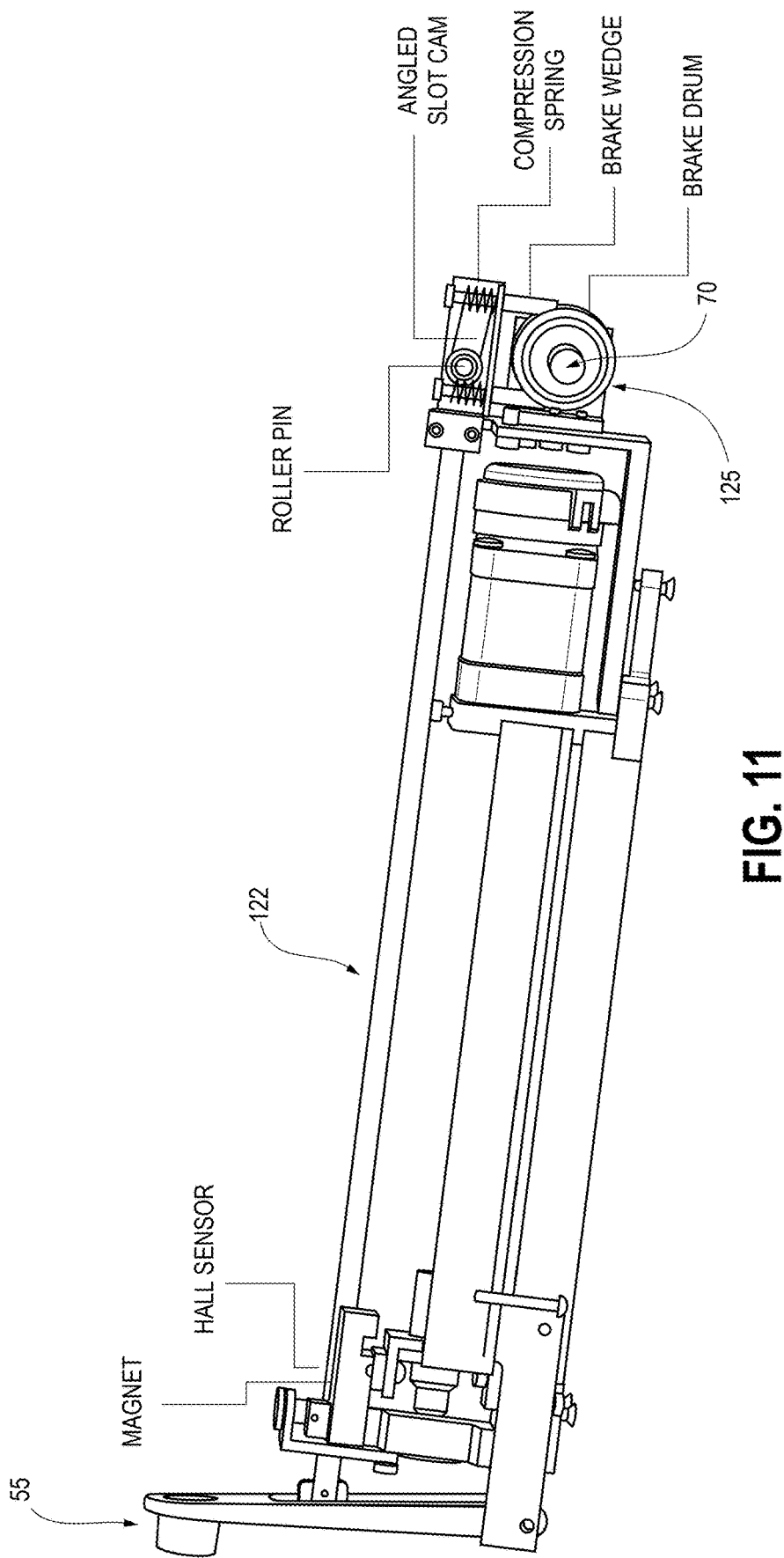
Figure 12:
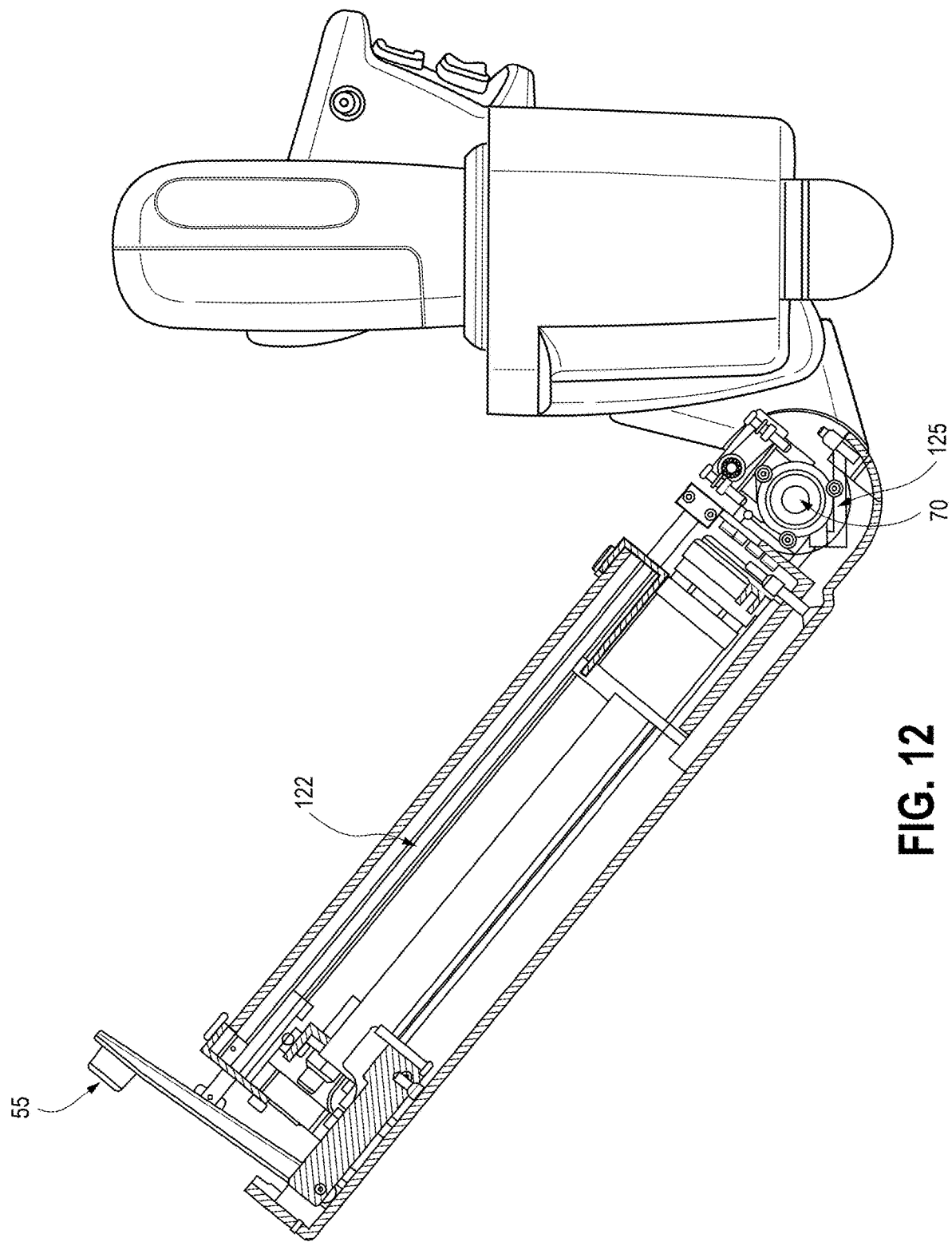

Looking now at FIGS. 10-12, there are shown further details of linear actuator 10. More particularly, linear actuator 10 preferably comprises a ball screw 110 mounted to a linear actuator motor 35 such that the shaft of ball screw 110 may be selectively rotated by actuation of linear actuator motor 35. Needle carriage 40 is mounted to the shaft of ball screw 110 such that rotation of the shaft of ball screw 110 in a first direction effects linear movement of needle carriage 40 (and hence, needle assembly 15 mounted thereto) in a first longitudinal direction relative to housing 30, and such that rotation of the shaft of ball screw 110 in a second, opposite direction effects linear movement of needle carriage 40 (and hence, needle assembly 15 mounted thereto) in a second, opposite direction relative to housing 30. It will be appreciated that, as a result of this construction, needle assembly 15 (and hence needle 65) may be selectively longitudinally advanced (i.e., moved distally) or retracted (i.e., moved proximally) relative to housing 30 of linear actuator 10 via selective operation of linear actuator motor 35.

In a preferred form of the invention, linear actuator 10 comprises a linear potentiometer 115 configured to measure the longitudinal movement of needle carriage 40 relative to housing 30 of linear actuator 10, whereby to provide data concerning the longitudinal disposition of needle carriage 40 (and hence, needle 65) relative to housing 30. If desired, an encoder 120 may be provided for measuring the rotational disposition, or movement, of linear actuator motor 35, whereby to provide data concerning the status of linear actuator motor 35.

Looking now at FIGS. 11 and 12, manual brake release 55 is coupled (e.g., via a brake control link 122) to a brake mechanism 125, such that movement of manual brake release 55 (e.g., distal movement of brake release 55 when pushed distally by the clinician) causes brake mechanism 125 to temporarily release, allowing linear actuator 10 to be rotated about rotary link 70. In a preferred form of the invention, manual brake release 55 is biased proximally so as to lock rotary link 70 and prohibit rotation of linear actuator 10 about rotary link 70 until manual brake release 55 is moved distally (i.e., pushed distally by the clinician) so as to release brake mechanism 125. It will be appreciated that since needle assembly 15 is mounted to needle carriage 40 of linear actuator 10, rotation of linear actuator 10 about rotary link 70 changes the angle of needle 65 relative to ultrasound device 20 (and hence, relative to the skin of a patient contacted by ultrasound device 20), as will hereinafter be discussed in further detail. It will also be appreciated that data obtained from linear potentiometer 115 and/or encoder 120 may be used (e.g., by appropriate software running on electronic device 80) to make adjustment calculations when an automated system is used to align needle 65 with a blood vessel which is targeted, as will hereinafter be discussed in further detail.

In a preferred form of the present invention, a sensor is provided to prevent linear actuator motor 35 from moving needle carriage 40 (and hence, needle 65 mounted to needle carriage 40) distally when manual brake release 55 is released (i.e., unlocked).

Figure 19:
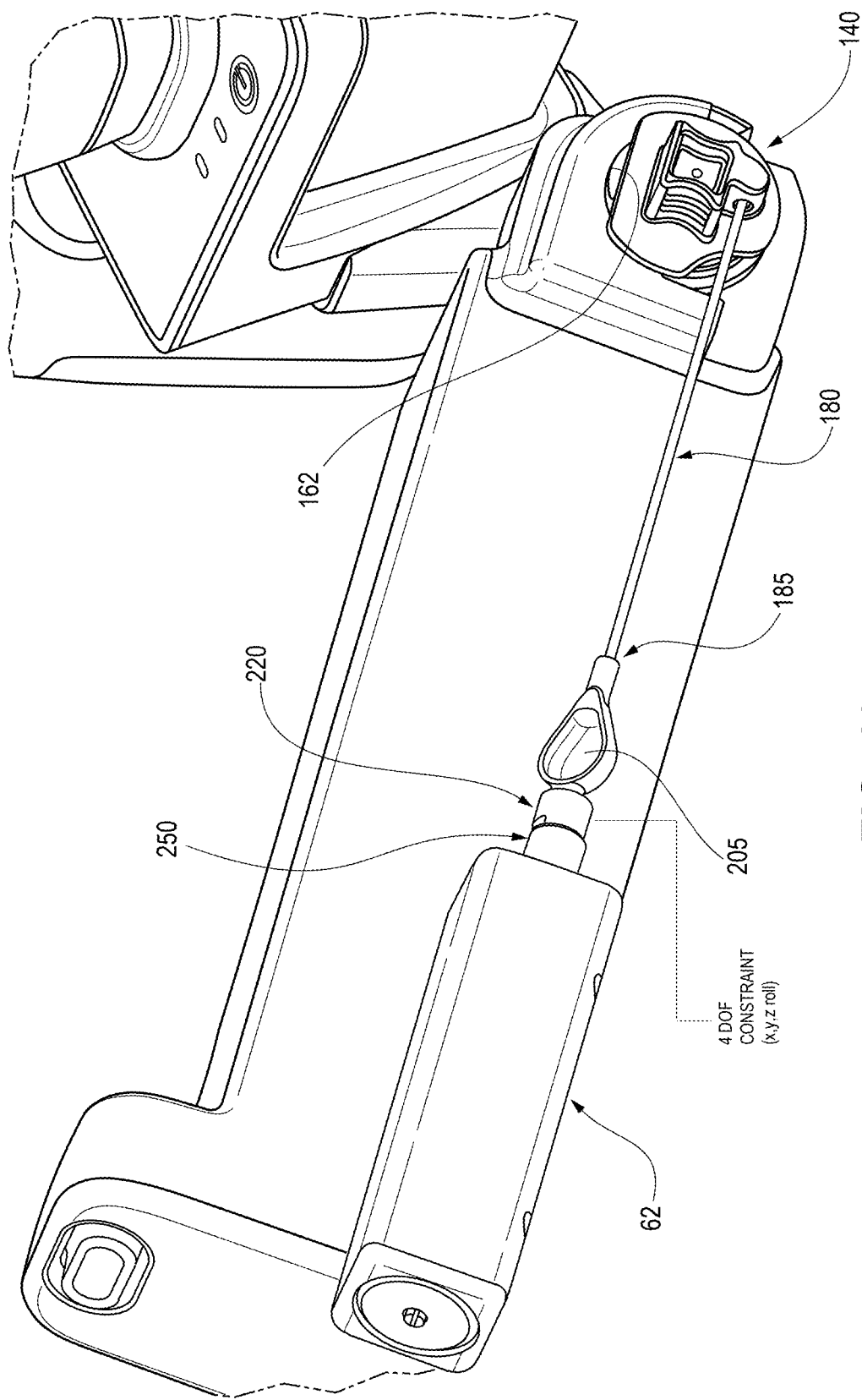
FIG. 19 is a schematic view showing a novel linear actuator formed in accordance with the present invention.

Needle guide seat 45 is formed in housing 30 of linear actuator 10, preferably aligned generally coincident with rotary link 70. See FIG. 1. Needle guide seat 45 comprises a geometry that matches the geometry of needle guide 50, whereby to retain needle guide 50 within needle guide seat 45 with a predetermined rotational disposition. More particularly, and looking now at FIGS. 13-17, in one preferred form of the invention, needle guide 50 comprises an inner surface 130 that faces housing 30 of linear actuator 10 when needle guide 50 is mounted in needle guide seat 45, an outer surface 135 comprising a gripping surface 140, and a needle passageway 145 for receiving needle 65, as will hereinafter be discussed in further detail. Inner surface 130 preferably comprises an inner surface projection 150 comprising a magnet 155 for magnetically interacting with housing 30 of linear actuator 10 (i.e., directly with needle guide seat 45 of housing 30 in the situation where needle guide seat 45 of housing 30 is formed out of a ferrous metal or, alternatively, interacting with a ferrous metal insert present in needle guide seat 45). Inner surface projection 150 of needle guide 50 further comprises a plurality of orientation tabs 160 disposed about the perimeter of inner surface projection 150. Orientation tabs 160 are received in counterpart orientation tab slots 162 (FIG. 19) disposed about the perimeter of needle guide seat 45. In a preferred form of the invention, a sterile surgical drape 165 (FIG. 1) is bonded (e.g., glued) to outer surface 135 of needle guide 50 prior to disposition of needle guide 50 in needle guide seat 45.

Figure 16:
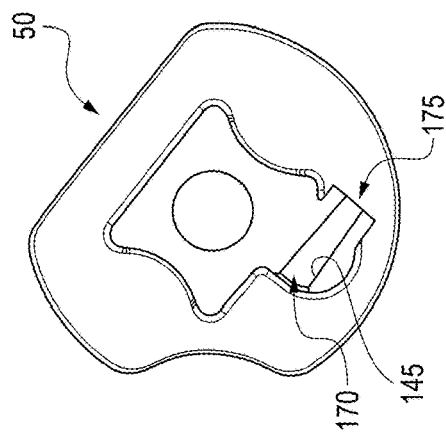
FIGS. 13-18 are schematic views showing further details of a novel needle guide formed in accordance with the present invention.
Figure 14:
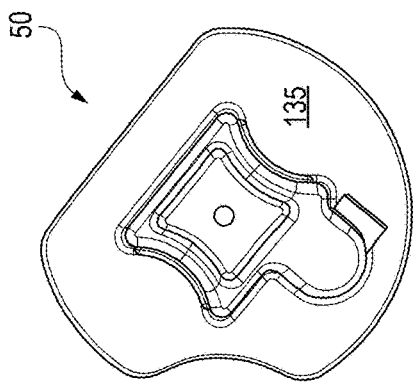
Figure 15:
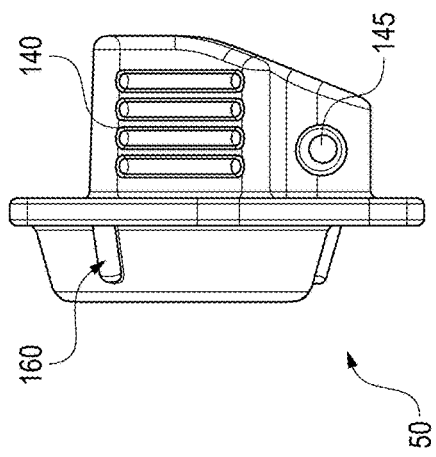
Figure 13:
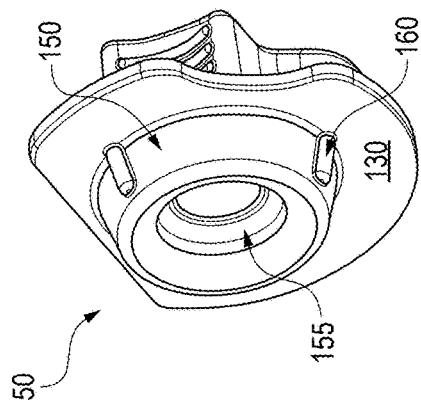
Figure 17:
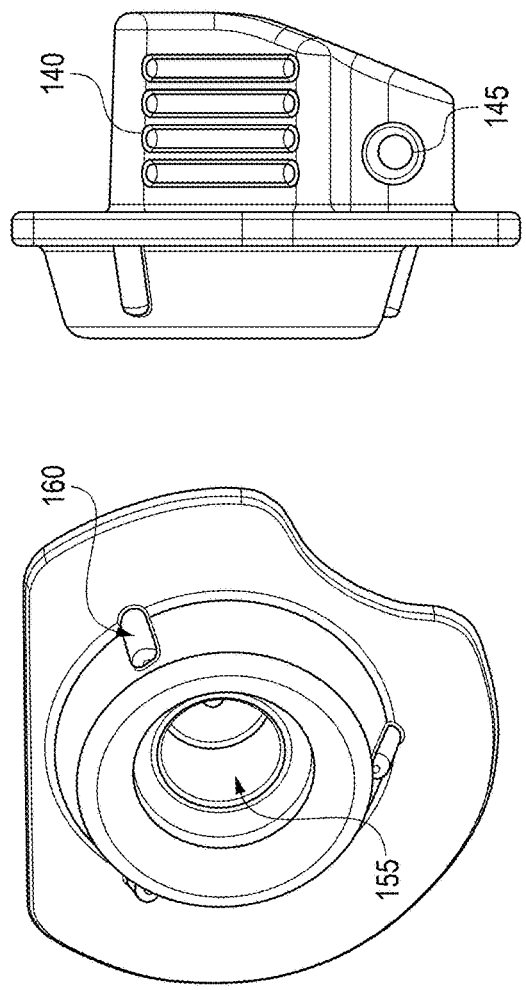
Figure 18:
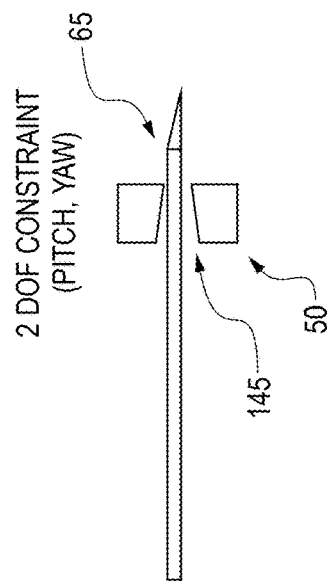

As a result of this construction, needle guide 50 can quickly and easily be mounted to, or removed from, needle guide seat 45 with a predetermined rotational disposition, such that needle inlet 145 is longitudinally aligned with, and able to receive, needle 65 when needle 65 is longitudinally advanced, as will hereinafter be discussed in further detail. To this end, needle passageway 145 is preferably generally "funnel shaped", such that the diameter of proximal inlet 170 of needle passageway 145 is larger than the diameter of distal outlet 175 of needle passageway 145 (FIG. 16). Forming needle passageway 145 with a taper will help guide the needle into the passageway and prevent the needle from bending as the needle is advanced into a patient. As shown in FIG. 18, passageway 145 also serves to constrain needle 65 as the needle is advanced into a patient).

Additionally, inasmuch as sterile surgical drape 165 is bonded to outer surface 135 of needle guide 50, surgical drape 165 can be used to cover linear actuator 10, needle housing 15 can be mounted to linear actuator 10, and needle guide 50 can then be inserted into needle guide seat 45 so that needle guide 50 and needle 65 are the only components of apparatus 5 disposed outside of drape 165. In this way, the needle does not need to puncture drape 165 when the needle advances into the skin of the patient. It will be appreciated that needle guide 50 and surgical drape 165 can be a disposable item that is discarded after each procedure performed with apparatus 5. Thus, apparatus 5 is configured to permit quick and easy attachment of a sterile surgical drape, while avoiding a situation in which needle 65 must pierce the surgical drape itself, thereby reducing the possibility of infection from transfer of microorganisms present on a surgical drape to the tip of the needle.

Needle Assembly 15

Looking now at FIGS. 19-27, there are shown further aspects of needle assembly housing 62, a motor 60, and a needle 65 of needle assembly 15.

More particularly, and looking now at FIGS. 19-22, needle 65 comprises a tissue penetrating member 180 comprising a proximal end 185, a pointed distal end 190, and a lumen 195 extending therebetween. A hub 200 is mounted to proximal end 185 of tissue penetrating member 180. Hub 200 comprises a distal teardrop-shaped cavity 205 defined by a bottom surface 210 and a perimeter wall 215 extending upwardly therefrom, and a proximally-extending magnetic mount 220. Teardrop-shaped cavity 205 comprises a distally-extending, funnel-shaped passageway 225 having a proximal end that opens on teardrop-shaped cavity 205, and a distal end in communication with lumen 195 of tissue penetrating member 180. Magnetic mount 220 comprises a proximal cavity 230 having one or more magnets 235 (FIG. 21) disposed therein for mating with a counterpart ferrous surface of needle assembly housing 62, as will hereinafter be discussed. A recess 240 (FIG. 20) is formed in the proximal most end of magnetic mount 220, whereby to mate with a projection formed on needle assembly housing 62, as will hereinafter be discussed.

Figure 23:
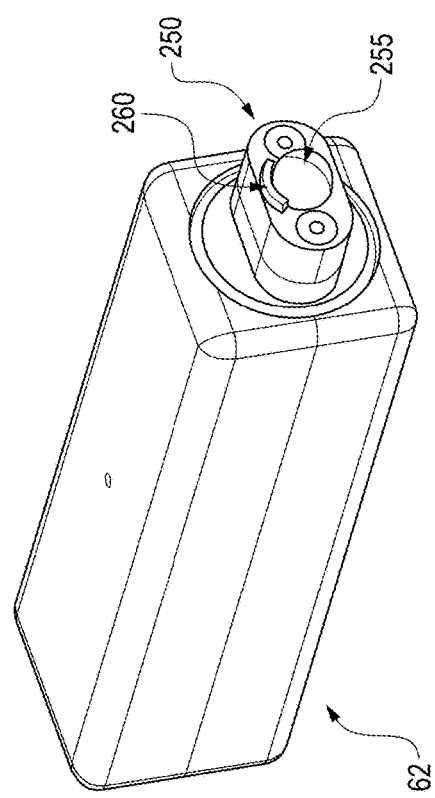
FIGS. 23-25 are schematic views showing further aspects of the novel linear actuator of FIG. 19.
Figure 24:
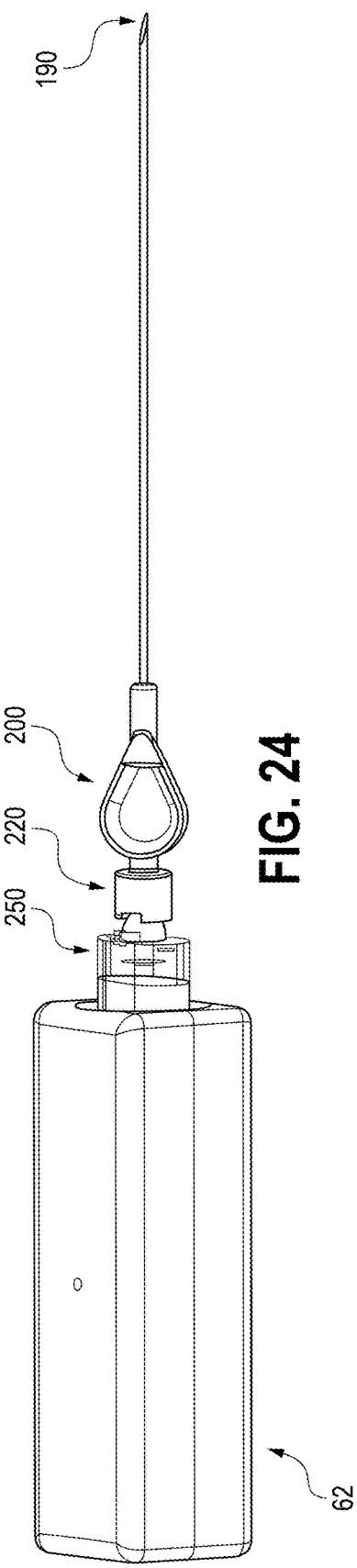

Looking now at FIGS. 23 and 24, needle assembly housing 62 comprises a distally-extending needle mount 250. Needle mount 250 extends distally from needle assembly housing 62 and is mechanically connected to needle assembly motor 60 such that vibrational energy may be mechanically transmitted by motor 60 to needle mount 250 (and hence to a needle 65 mounted thereto), as will hereinafter be discussed in further detail.

Needle mount 250 comprises a distal ferrous metal ball 255 sized to be received within proximal cavity 230 of magnetic mount 220 of needle 65, and a flange 260 sized to be received within recess 240 of magnetic mount 220 of needle 65. As a result of this construction, it will be appreciated that needle 65 can be quickly and easily mounted to needle assembly housing 62 by aligning proximal cavity 230 of needle 65 with ferrous ball 255 of needle mount 250. The interaction of magnet(s) 235 of hub 200 of needle 65 with ferrous metal ball 255 of needle mount 250 allows needle 65 to be magnetically mounted to motor 60 and maintained in mechanical connection therewith. Needle 65 can then be rotated (e.g., by the clinician during attachment of needle 65 to needle assembly housing 62) such that flange 260 of needle mount 250 seats within recess 240 of hub 200 of needle 65.

As a result of this construction, it is possible to quickly and easily mount needle 65 to needle assembly housing 62 such that it is rotationally disposed along its longitudinal axis in a desired manner, i.e., such that the open side of teardrop-shaped cavity 205 faces away from linear actuator 10, whereby to permit the clinician easy access to teardrop-shaped cavity 205. Thus, if desired, the clinician is able to easily access teardrop-shaped cavity 205 of needle 65 so as to insert a surgical element therein (e.g., a guidewire), and advance the surgical element distally through funnel-shaped passageway 225 of hub 200, and through lumen 195 of tissue penetrating member 180 such that the surgical element extends out of pointed distal end 190 of tissue penetrating member 180. It will be appreciated that this is typically done after tissue penetrating member 180 has been advanced into the tissue of a patient such that pointed distal end 190 of tissue penetrating member 180 is disposed within a lumen of a hollow structure (e.g., blood vessel), thus allowing the clinician to insert a guidewire into the internal lumen of a blood vessel and carry out additional surgical procedures, as will hereinafter be discussed in further detail. Specifically, in a preferred form of the present invention, needle 65 is mounted to needle assembly housing 62 such that the open side of teardrop-shaped cavity 205 faces away from linear actuator 10. This orientation facilitates the advancement of a surgical element (e.g., a guidewire) into teardrop-shaped cavity 205, through funnel-shaped passageway 225 of hub 200, and through lumen 195 of tissue penetrating member 180 so that the surgical element extends out of pointed distal end 190 of tissue penetrating member 180. Importantly, the clinician inserting the surgical element into teardrop-shaped cavity 205 is able to do so using only one hand, and without having to remove needle 65 from needle assembly housing 62 or disassemble a needle. This is a significant advance over the configuration of prior art systems in which a syringe is attached to the proximal end of a needle via a luer lock connector (or other connector) for use in confirming when a needle has penetrated a blood vessel. With such prior art systems, after access to the blood vessel has been confirmed (e.g., after the distal end of the needle penetrates the blood vessel and the syringe fills with blood), the clinician must disconnect the syringe from the proximal end of the needle in order to provide an opening in the proximal end of the needle for inserting the guidewire. Disconnecting the syringe from the needle is a challenging process that typically requires the use of two hands, particularly where the syringe is mounted to the needle by a rotating luer lock connector. Moreover, disconnecting the syringe from the needle often causes the needle to move, potentially dislodging the distal end of the needle from the blood vessel, thereby losing access to the blood vessel. By providing the teardrop-shaped cavity 205 at the proximal end of needle 65, the clinician can pass a surgical element through the proximal end of needle 65 without the risk of losing access to the blood vessel.

It should also be appreciated that, if desired, needle 65 may be replaced by substantially any surgical instrument that it is desired to advance through into the tissue of a patient using the novel apparatus of the present invention.

Specifically, novel magnetic mount 220 may be mounted to the proximal end of substantially any surgical instrument to be advanced distally into the tissue of a patient and, in turn, mounted to needle mount 250 of needle assembly housing 62. By way of example but not limitation, such alternative surgical instruments may include a biopsy device, a therapeutic (e.g., drug) delivery device, a neurostimulation electrode, a sheath needle, etc., and such alternative surgical instruments may be magnetically mounted to needle mount 250 of needle assembly housing 62 without departing from the scope of the present invention.

Vibrator 265

Figure 25:
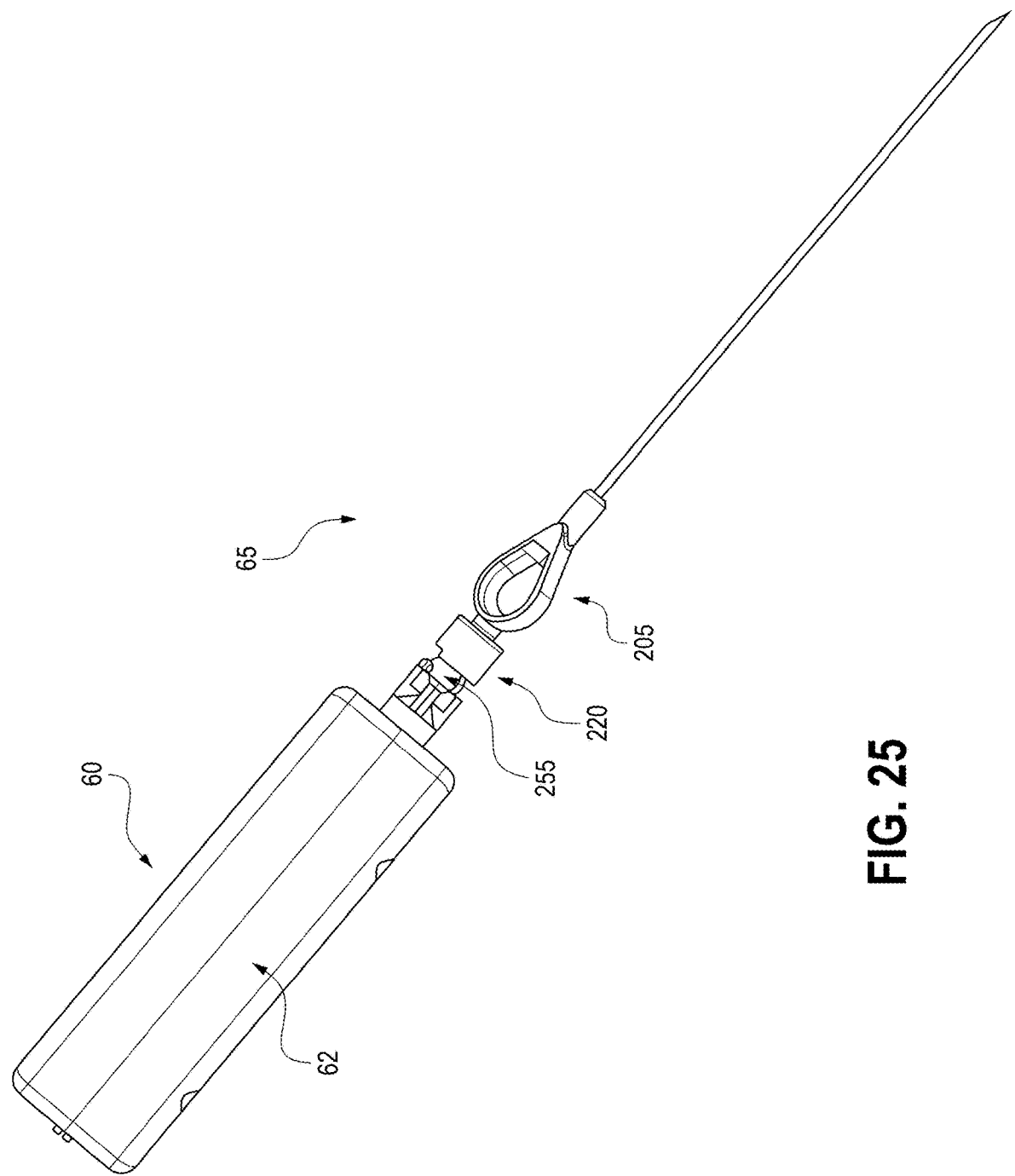
Figure 26:
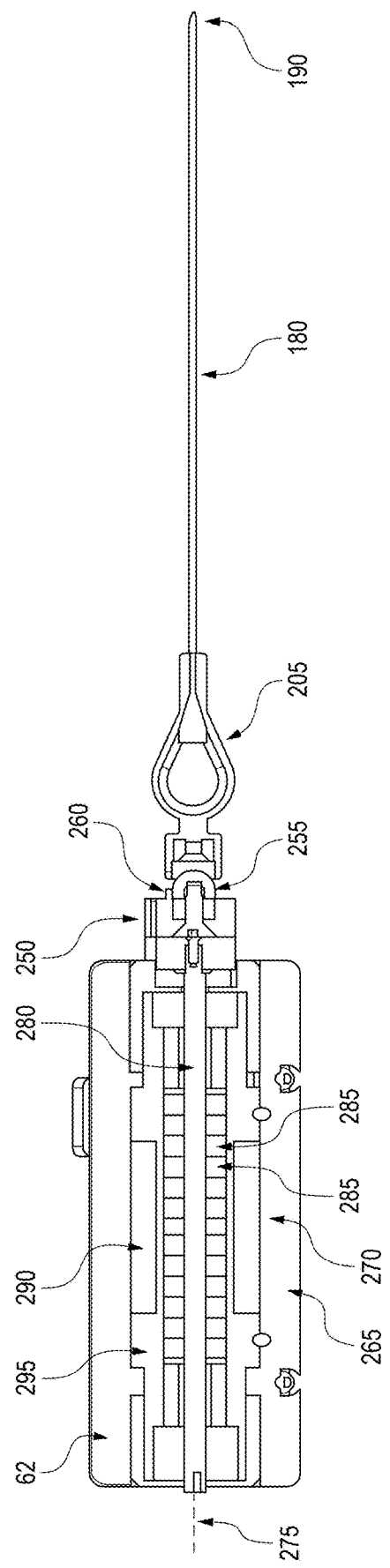
FIGS. 26 and 27 are schematic views showing further aspects of a novel vibrator formed in accordance with the present invention, configured for use with the novel linear actuator of FIG. 19.
Figure 27:
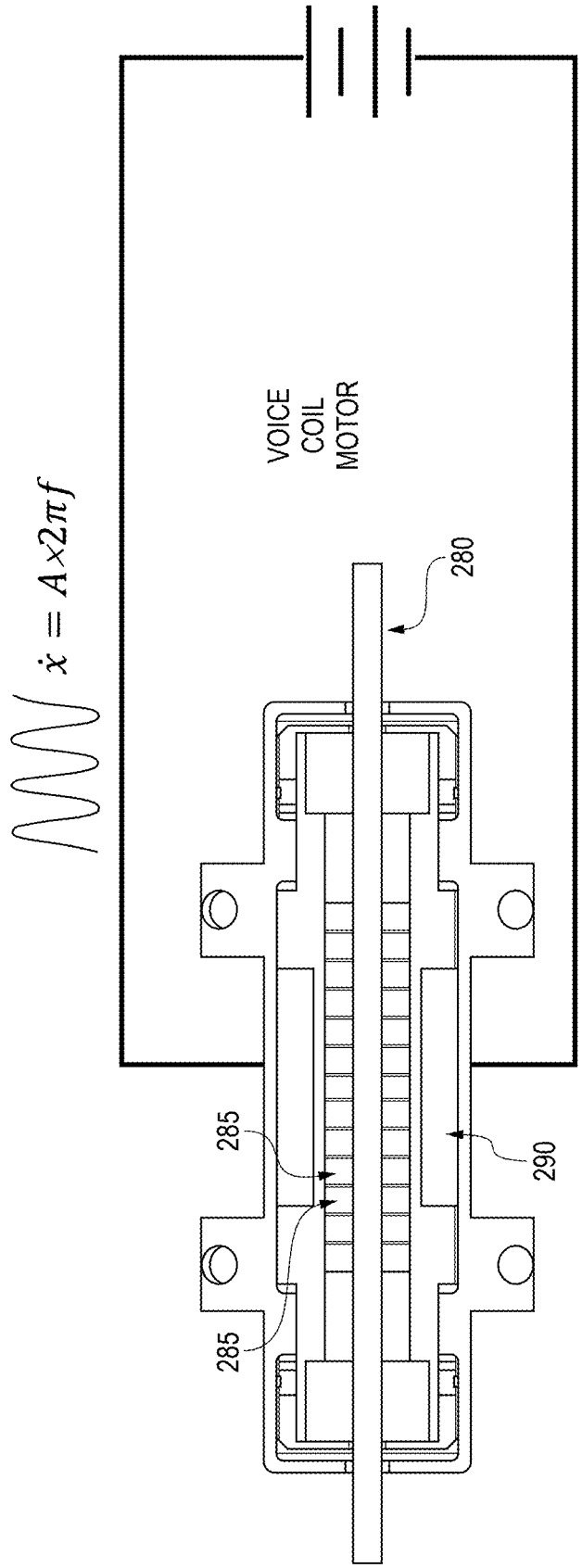

Looking now at FIGS. 25-27, needle assembly motor 60 preferably comprises a vibrator 265. Vibrator 265 comprises a vibrational actuator 270 in electrical communication with electronic device 80, e.g., with a processor of electronic device 80 that is configured to instruct vibrator 265 when to activate and the operational parameters to use, as will hereinafter be discussed in further detail. It will be appreciated that operation of vibrator 265 may be based on a variety of factors, including but not limited to the type of vibrational actuator 270 used, and the type and condition of the tissue being penetrated by tissue penetrating member 180. When activated, vibrational actuator 270 provides repetitive, reciprocating or oscillating motion to tissue penetrating member 180 back and forth along a longitudinal direction 275 (FIG. 26). Longitudinal direction 275 is coincident with the axis of the tissue penetrating member 180. As used herein, the terms "reciprocating," "oscillating," and "vibrating" may be used interchangeably, and refer to a back and forth motion of tissue penetrating member 180 in longitudinal direction 275 coincident with, or parallel to, the length of the tissue penetrating member 180.

Upon receiving an activation signal from electronic device 80 (e.g., the processor carried by electronic device 80), vibrational actuator 270 turns on. Activation may occur automatically, or only at a certain point in the insertion process, such as once tissue penetrating member 180 is properly positioned and aligned with the blood vessel to be accessed by tissue penetrating member 180, but prior to being deployed for insertion, as will hereinafter be discussed. If desired, activation of vibrational actuator 270 may occur only after the proper positioning of the tissue penetrating member 180 is confirmed by the clinician, or activation of vibrational actuator 270 may automatically begin once a target point on electronic device 80 is aligned with the blood vessel to be accessed, as will hereinafter be discussed.

Vibrator 265 comprises a drive shaft 280 that extends from vibrational actuator 270 to needle mount 250 (to which needle 65, including tissue penetrating member 180 is magnetically mounted, as discussed above). Drive shaft 280 transfers the mechanical vibrational motion generated by vibrational actuator 270 to tissue penetrating member 180. It should be appreciated that, if desired, vibrator 265, and hence, vibrational actuator 270, may be axially offset from tissue penetrating member 180, with an appropriate mechanical connection between drive shaft 280 of vibrator 265 and needle mount 250 being used to transmit vibrational energy from vibrator 265 to tissue penetrating member 180, as will be apparent to one of skill in the art in view of the present disclosure.

Figure 28:
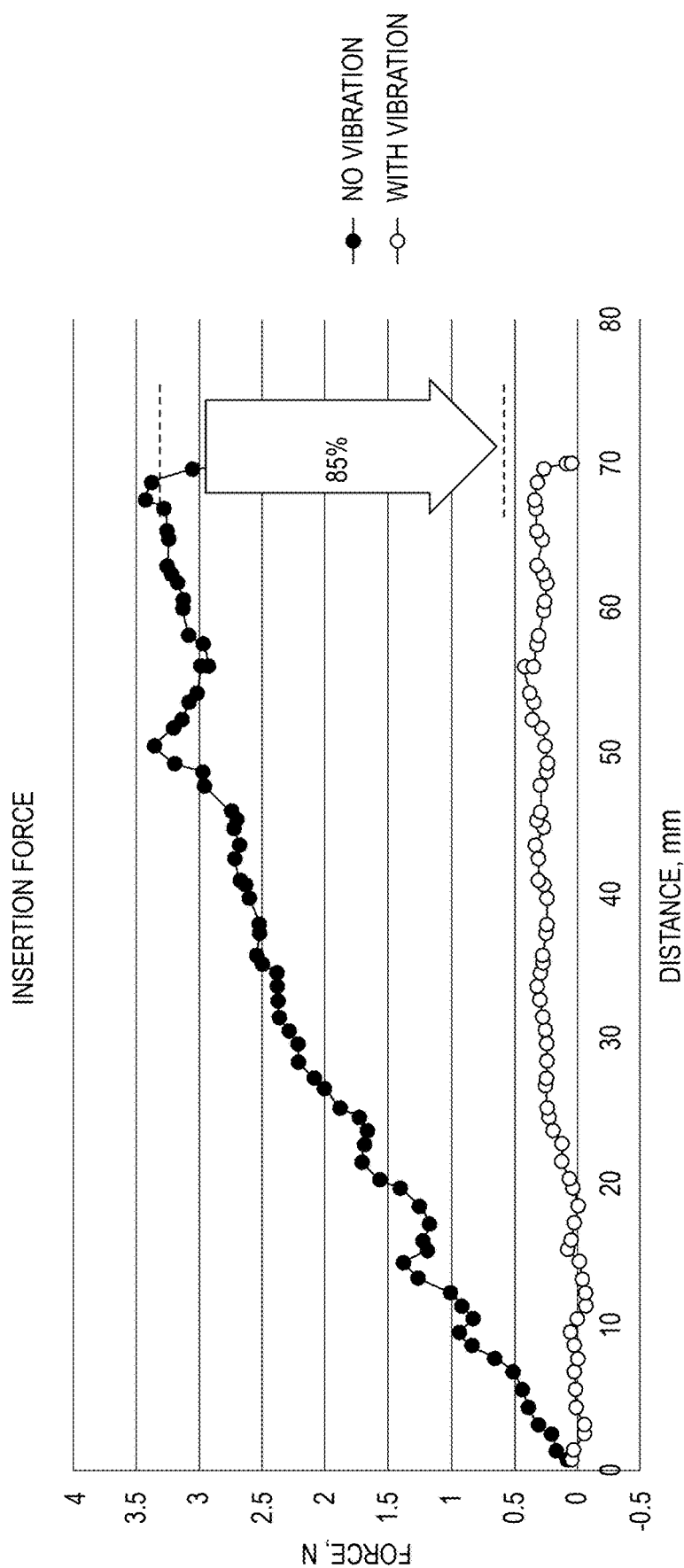
FIGS. 28 and 29 illustrate the reduction in the insertion force necessary to insert a needle into the tissue of a patient which is obtained by use of the novel image-guided robotic system of the present invention.
Figure 29:
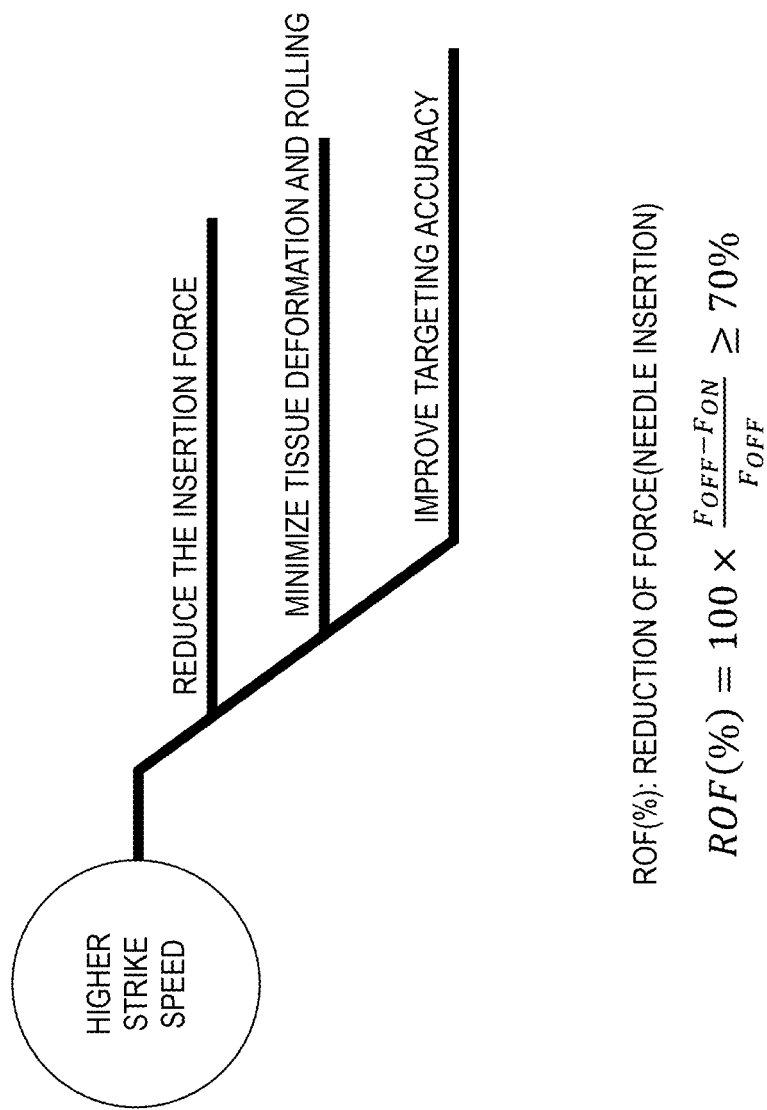

Vibration of tissue penetrating member 180 by vibrational actuator 270 may be accomplished in a variety of ways, which may be selected based on the type of tissue being penetrated. The particular actuation mechanism useful to overcome the tissue deformation and insertion force depends on the resonance frequency and other electromechanical properties of the system to beneficially interact with the resonance and other mechanical properties of the tissue, vessels or other structures encountered by sharpened distal end 190 of tissue penetrating member 180 as it is advanced into tissue. See, for example, FIG. 28 which shows the relationship between the insertion force necessary to advance tissue penetrating member 180 through the tissue of a patient with, or without, vibrating tissue penetrating member 180, and FIG. 29 which shows an equation for calculating the reduction of force necessary to advance tissue penetrating member 180 through tissue when tissue penetrating member 180 is caused to vibrate.

By way of example but not limitation, if desired, vibrational actuator 270 may be in the form of a piezoelectric motor. However, transducer technologies that rely on conventional, single or stacked piezoelectric ceramic assemblies for actuation can be hindered by the maximum strain limit of the piezoelectric materials themselves. Because the maximum strain limit of conventional piezoelectric ceramics is about 0.1% for poly crystalline piezoelectric materials, such as ceramic lead zirconate titanate (PZT) and 0.5% for single crystal piezoelectric materials, it would require a large stack of cells to approach displacement or actuation of several millimeters or even many tens of microns. Using a large stack of cells to actuate components would also require that the medical tool size be increased beyond usable biometric design for handheld instruments.

Flextensional transducer assembly designs have been developed which provide amplification in piezoelectric material stack strain displacement. The flextensional designs comprise a piezoelectric material transducer driving cell disposed within a frame, platen, endcaps or housing. The geometry of the frame, platen, endcaps or housing provides amplification of the axial or longitudinal motions of the driver cell to obtain a larger displacement of the flextensional assembly in a particular direction. Essentially, the flextensional transducer assembly more efficiently converts strain in one direction into movement (or force) in a second direction.

Examples of flextensional transducers which may be used to vibrate tissue penetrating member 180 are described in U.S. patent application Ser. No. 16/837,675, which patent application is hereby incorporated herein by reference.

By way of further example but not limitation, in one preferred embodiment of the present invention, vibrational actuator 270 is provided in the form of a voice coil motor. In this form of the invention, the voice coil motor creates low frequency reciprocating motion. The voice coil has a bandwidth of approximately 10-60 Hz and a displacement of up to 10 mm that is dependent upon applied AC voltage. In particular, when an alternating electric current is applied through a conducting coil, the result is a Lorentz Force in a direction defined by a function of the cross-product between the direction of current through the conductive coil and magnetic field vectors of the magnetic member. The force results in a reciprocating motion of the magnetic member relative to the coil support tube which is held in place by the body. With a magnetic member fixed to a driving tube, the driving tube communicates this motion to an extension member, such as drive shaft 280 of vibrator 265, which in turn communicates motion to tissue penetrating member 180. A first attachment point fixes the distal end of the coil support tube to the motor housing. A second attachment point fixes the proximal end of the coil support tube to the motor housing. The magnetic member may be made of a Neodymium-Iron-Boron (NdFeB) composition. However, other compositions such as, but not limited to, Samarium-Cobalt (SmCo), Alnico (AlNiCoCuFe), Strontium Ferrite (SrFeO), or Barium Ferrite (BaFeO) could be used. Slightly weaker magnets could be more optimal in some embodiments, such as a case where the physical size of the system is relatively small and strong magnets would be too powerful.

Looking back to FIG. 27, there is shown a preferred form of the present invention in which vibrational actuator 270 is provided in the form of a voice coil motor. In this form of the invention, vibrational actuator 270 comprises a plurality of magnets 285 mounted to drive shaft 280. Magnets 285 are preferably cylindrical, comprising a central opening sized to receive drive shaft 280 therein such that magnets 285 extend circumferentially about drive shaft 280. A conducting coil 290 is mounted to a support tube 295 which surrounds magnets 285 so as to permit linear motion of magnets 285 relative to conducting coil 290 and support tube 295. As a result of this construction, when an alternating electric current is applied through conducting coil 290, the result is a Lorentz Force in a direction defined by a function of the cross-product between the direction of current through conducting coil 290 and magnetic field vectors of the magnetic member (i.e., a Lorentz Force directed along longitudinal direction 275). The force results in a reciprocating motion of magnets 285 relative to the support tube 295 (which is, in turn, held in place by the housing of vibrator 265). Thus, selective energizing of conducting coil 290 effects longitudinal movement of magnets 285 (and hence, drive shaft 280 mounted thereto) in a longitudinal direction, whereby to generate vibrational energy proportional to the current used to energize conducting coil 290.

Conducting coil 290 may be made in different configurations including, but not limited to, several layers formed by a single wire, several layers formed of different wires, either round or other geometric shapes. In a first embodiment of conducting coil 290, a first layer of conductive wire is formed by wrapping the wire in a turn-like and spiral fashion and in a radial direction around the coil-support tube, with each complete revolution forming a turn next to the previous one and down a first longitudinal direction of the coil support tube 295. After a predetermined number of turns, an additional layer is formed over the first layer by overlapping a first turn of a second layer of the wire over the last turn of the first layer and, while continuing to wrap the wire in the same radial direction as the first layer, forming a second spiral of wiring with at least the same number of turns as the first layer, each turn formed next to the previous one and in a longitudinal direction opposite to that of the direction in which the first layer was formed. Additional layers may be added by overlapping a first turn of each additional layer of the wire over the last turn of a previous layer and, while continuing to wrap the wire in the same radial direction as the previous layer, forming an additional spiral of wiring with at least the same number of turns as the previous layer, each turn formed next to the previous one and in a longitudinal direction opposite to that of the direction in which the previous layer is formed.

It should be appreciated that, if desired, the locations of magnets 285 and conducting coil 290 may be swapped. In other words, if desired, conducting coil 290 may be wrapped around and attached to drive shaft 280 and magnets 285 may be located along an outside radius of drive shaft 280 mounted to support tube 295. An electrical current may then be applied at appropriate conductive attachment sites so as to energize conducting coil 290, whereby to cause the formation of the Lorentz Force that moves conducting coil 290 (and hence, drive shaft 280 to which conducting coil 290 is mounted) reciprocally along longitudinal direction 275. Conductive coil 290 is physically in contact with the drive shaft 280 of vibrator 265 in this form of the invention.

Alternatively, if desired, vibrational actuator 270 may employ a dual-coil mechanism in which the magnets 285 are replaced with a second conducting coil (not shown). In this form of the invention, the second conducting coil is wrapped around, and attached to, drive shaft 280 of vibrator 265, and the first conductive coil is located along an outside radius of the support tube 295 in the manner discussed above. In a first version according to this embodiment of the invention, the inner coil conducts direct current DC and the outer coil conducts alternating current AC. In a second version according to this embodiment of the invention, the inner coil conducts alternating current AC and the outer coil conducts direct current DC. In a third version according to this embodiment of the invention, both the inner and outer coils conduct alternating current AC.

It will be appreciated that in all of the voice coil actuator configurations discussed above, springs (not shown) may be used to limit and control certain dynamic aspects of tissue penetrating member 180.

By way of still further example but not limitation, in still another embodiment of the present invention, if desired, vibrational actuator 270 may be provided in the form of a solenoid actuator. As with the other voice coil embodiments using coils, the basic principle of actuation with a solenoid actuator is caused by a time varying magnetic field created inside a solenoid coil which acts on a set of very strong permanent magnets. The magnets and the entire penetrating member assembly oscillate back and forth through the solenoid coil. Springs absorb and release energy at each cycle, amplifying the vibrational energy imparted to tissue penetrating member 180. With this form of the invention, the resonant properties of the vibrational actuator 270 can be optimized by magnet selection, number of coil turns in the solenoid, mass of the shaft, and the stiffness of the springs.

It should be appreciated that, while piezoelectric, voice coil and solenoid mechanisms have been discussed above for providing the vibrational energy generated by vibrational actuator 270, there exist various other approaches to actuating or oscillating the tissue penetrating member 180 that will be apparent to those of skill in the art in view of the present disclosure. Other approaches, such as a rotating motor, could be used to provide the vibrational energy generated by vibrational actuator 270. Generally, any type of motor comprising an actuator assembly, further comprising a mass coupled to a piezoelectric material, or a voice coil motor, or solenoid, or any other translational motion device, would also fall within the spirit and scope of the invention and will be apparent to those of skill in the art in view of the present disclosure.

As discussed above, vibrator 265 of motor 245 is configured to generate oscillations of drive shaft 280 in longitudinal direction 275. Since drive shaft 280 is connected to tissue penetrating member 180 through a needle mount 250, vibrations or oscillations generated by vibrator 265 are transferred to tissue penetrating member 180. As used herein, the terms "vibration" and "oscillation" may be used interchangeably. Vibrational actuator 270 of vibrator 265 may be any suitable motor such as discussed above, including, but not limited to, a voice coil motor (VCM), a piezoelectric motor having at least one piezo element therein, and a DC motor. Vibrational actuator 270 is capable of producing vibrations at a rate of 50-50,000 oscillations per second depending on the type of vibrational actuator, frequency and/or input power. In at least one embodiment of present invention, the vibration rate may preferably be up to a maximum of about 200 oscillations per second, and preferably between 20 and 200 oscillations per second. The vibrations produced can vibrate the penetrating member 310 at amplitudes of about 5 μm to 1 mm, and preferably 0.5 mm.

Figure 4:
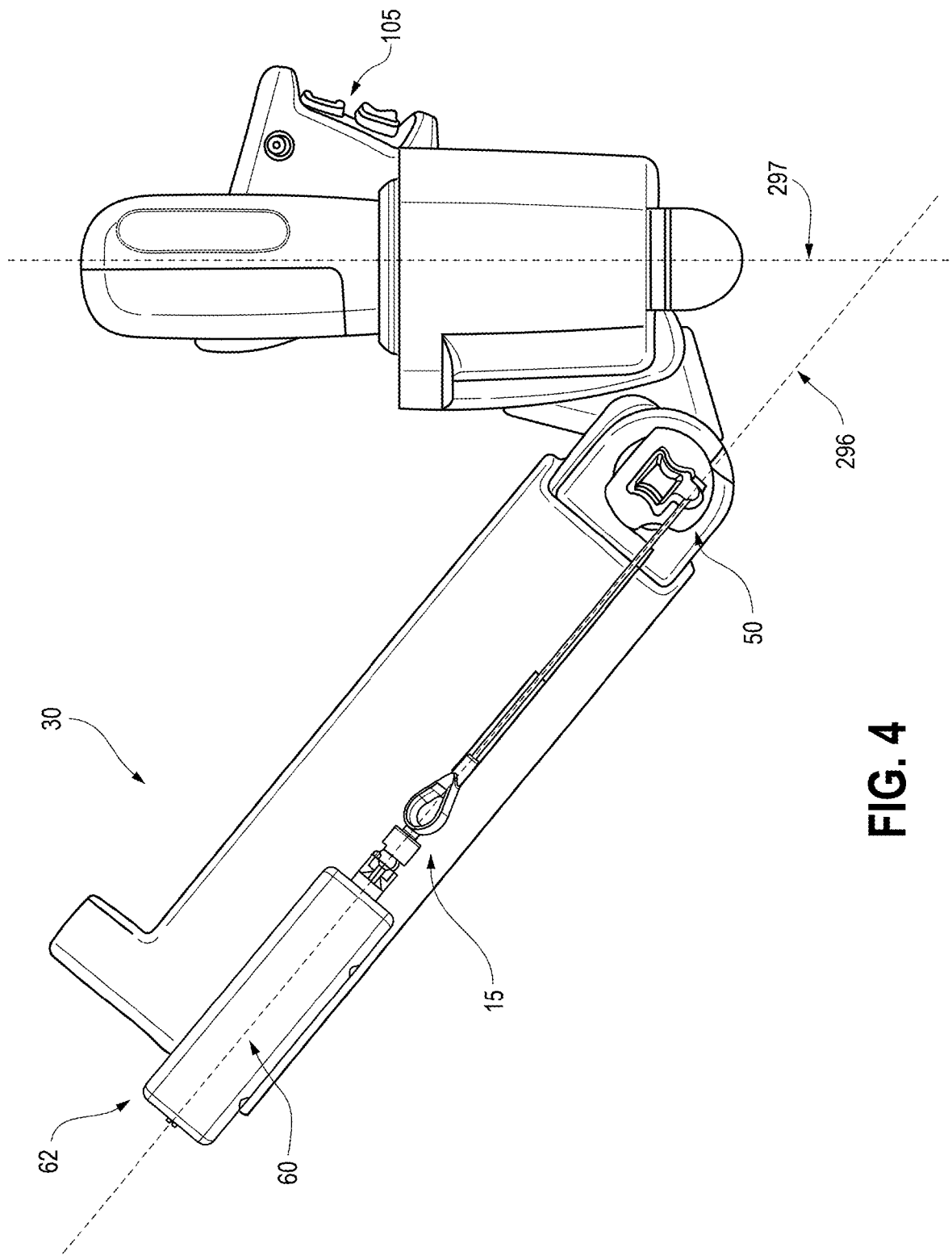
Figure 6:
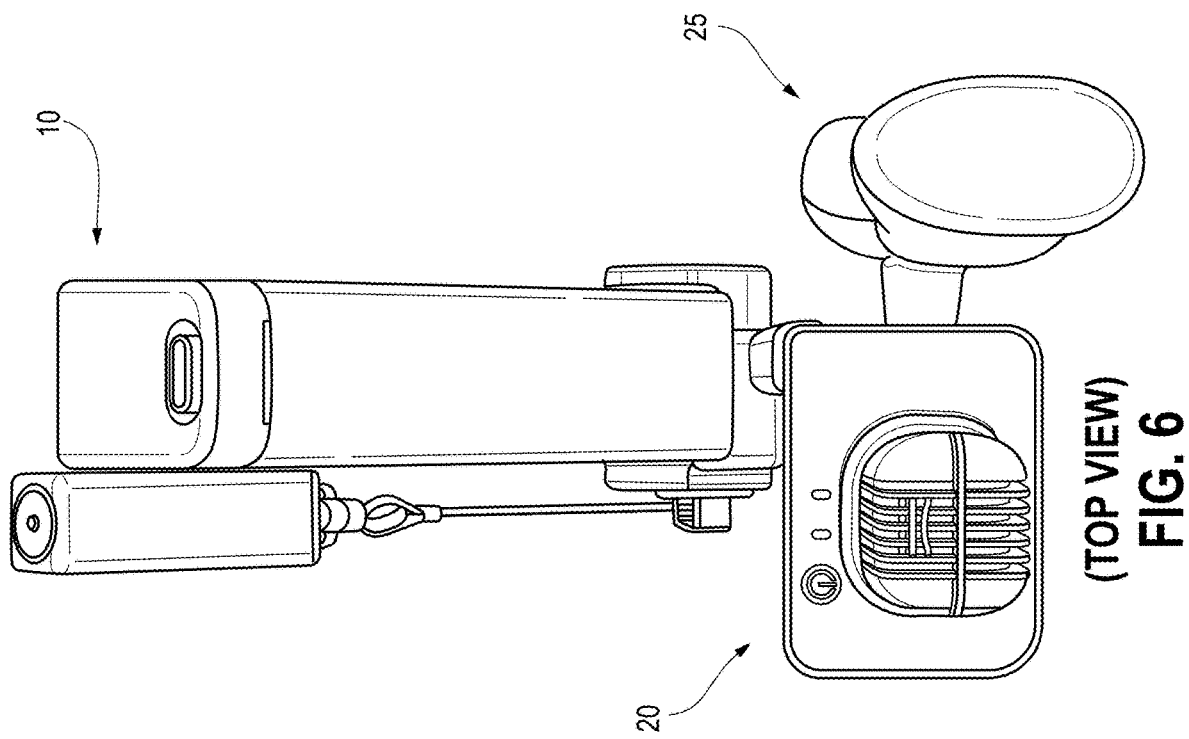
Figure 5:
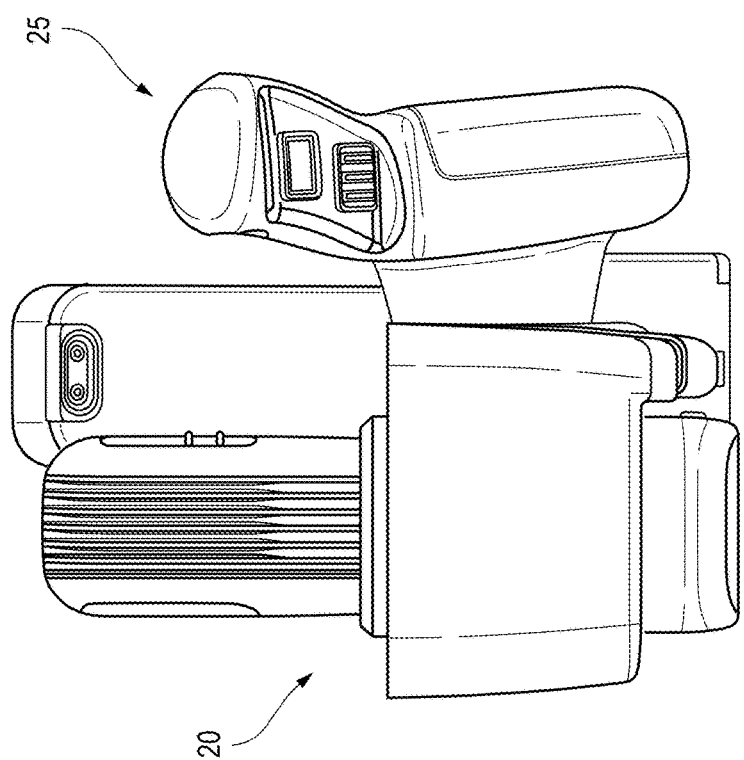
Figure 9:
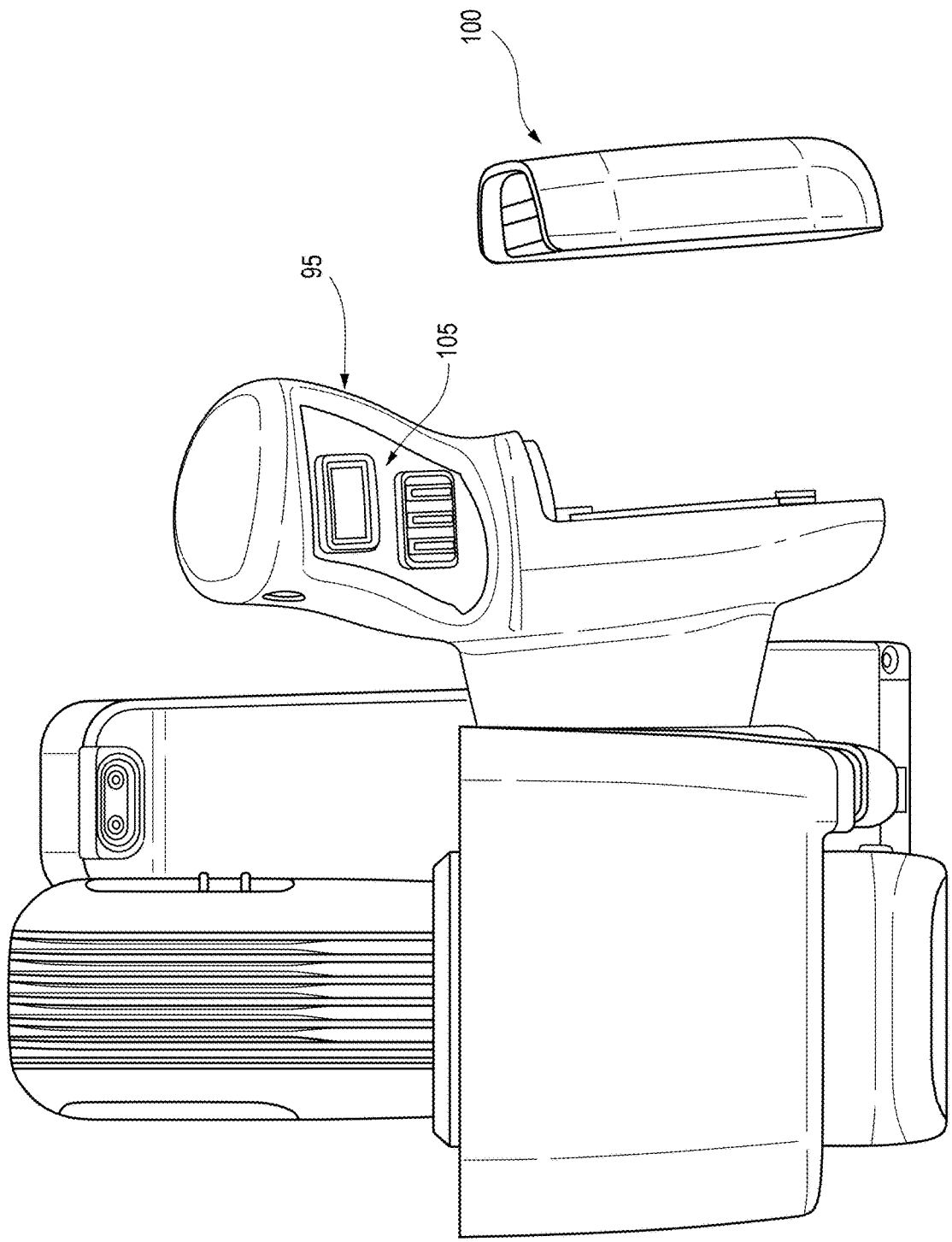

It will be appreciated that a key feature of the present invention is the angle of a longitudinal axis 296 (FIG. 4) of tissue penetrating member 180 relative to a longitudinal axis 297 (FIG. 4) which passes through the center of ultrasound probe 75 of ultrasound device 20. For the sake of clarity, this angle will be discussed herein as the angle between linear actuator 10 and ultrasound device 20 (i.e., the components of apparatus 5 that are configured to move relative to one another about rotary link 70), however, it should be appreciated that reference to these components to describe this angle is a shorthand way to discuss the angle between longitudinal axis 296 of tissue penetrating member 180 and longitudinal axis 297 of ultrasound probe 75 (as can be seen in FIG. 4).

Ultrasound Device 20

Figure 30:
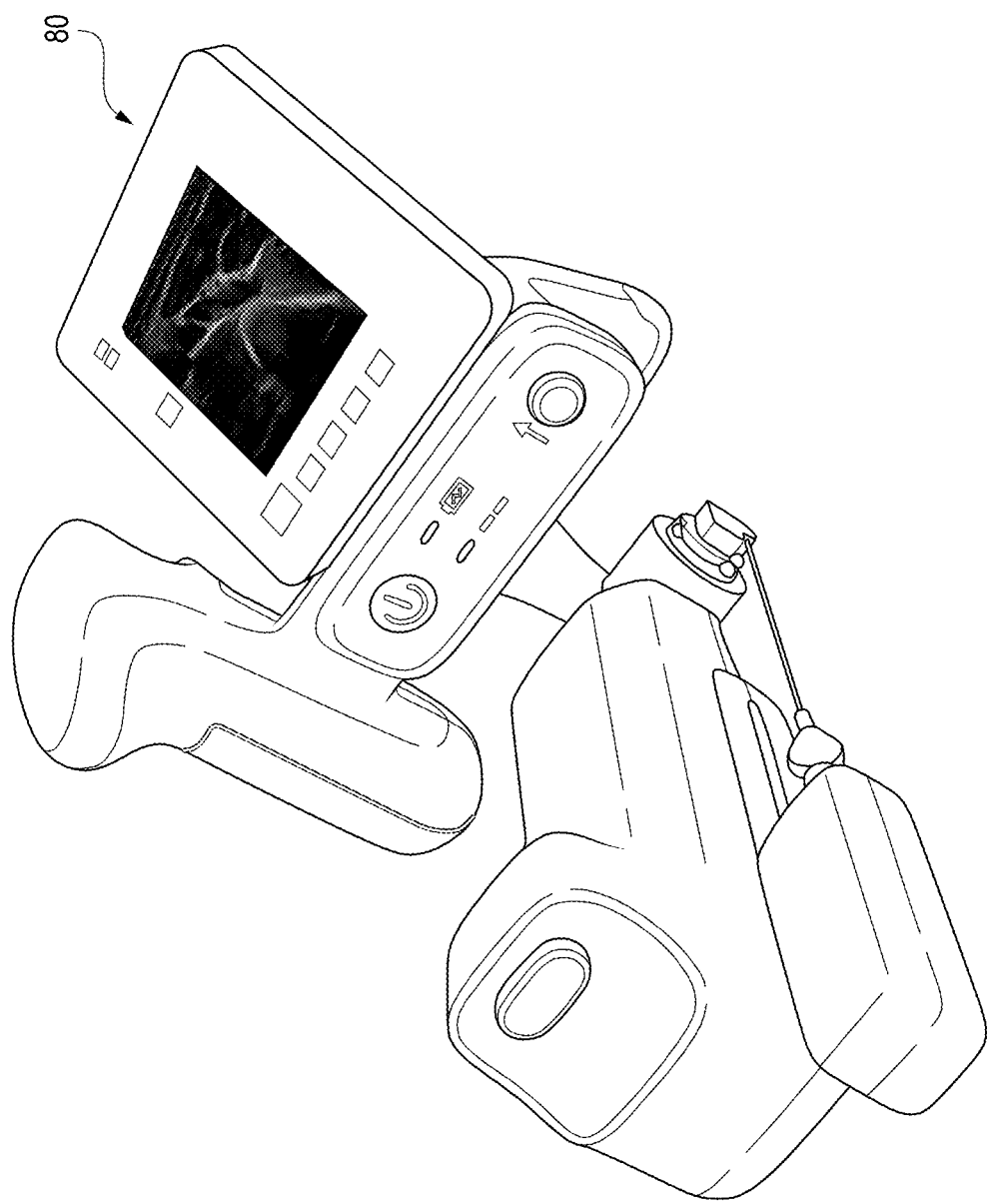
FIGS. 30 and 31 are schematic views showing details of an electronic device configured for use with the present invention.

As discussed above, apparatus 5 comprises an ultrasound device 20 configured to obtain data and information on the tissue of a subcutaneous area, and an electronic device 80 (e.g., a tablet computer) for interacting with and controlling electronics components of apparatus 5. It will be appreciated that, if desired, electronic device 80 may instead be physically integrated into apparatus 5 (e.g., as a monitor and accompanying electronics mounted to ultrasound device 20), or provided as a component that is selectively detachable from apparatus 5 (e.g., a tablet that is magnetically mounted to ultrasound device 20 so as to be selectively removed therefrom and used as an external device if desired). See FIG. 30.

Electronic Device 80

Figure 31:
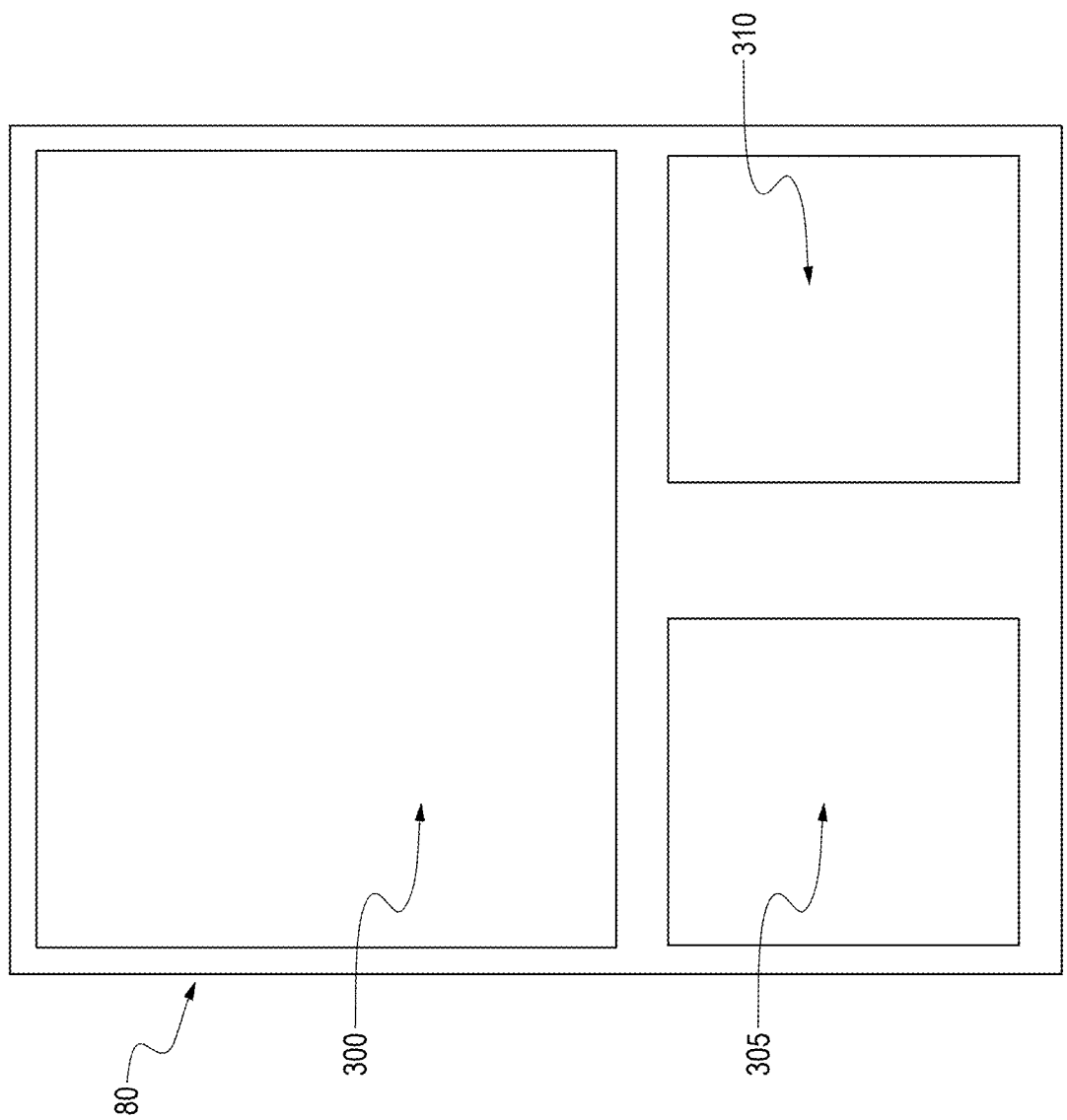

In one preferred form of the invention, and looking now at FIG. 31, electronic device 80 comprises a display 300 (e.g., a touchscreen) and a wireless transceiver 305 for wirelessly communicating with ultrasound device 20 (e.g., via Wi-Fi, Bluetooth, etc.). Electronic device 80 preferably comprises appropriate software and a processor 310 (i.e., a CPU) configured to use data received from ultrasound device 20 (e.g., imaging data from ultrasound probe 75) and/or positional data from rotary angle sensor 72 and/or linear potentiometer 115 to calculate various positioning and adjustment parameters for tissue penetrating member 180 such that tissue penetrating member 180 can be inserted through the tissue of a patient aligned with a predetermined target hollow structure (e.g., a blood vessel) with the result that pointed distal end 190 of tissue penetrating member 180 pierces the hollow structure and is disposed in communication with a lumen of the hollow structure.

Figure 32:
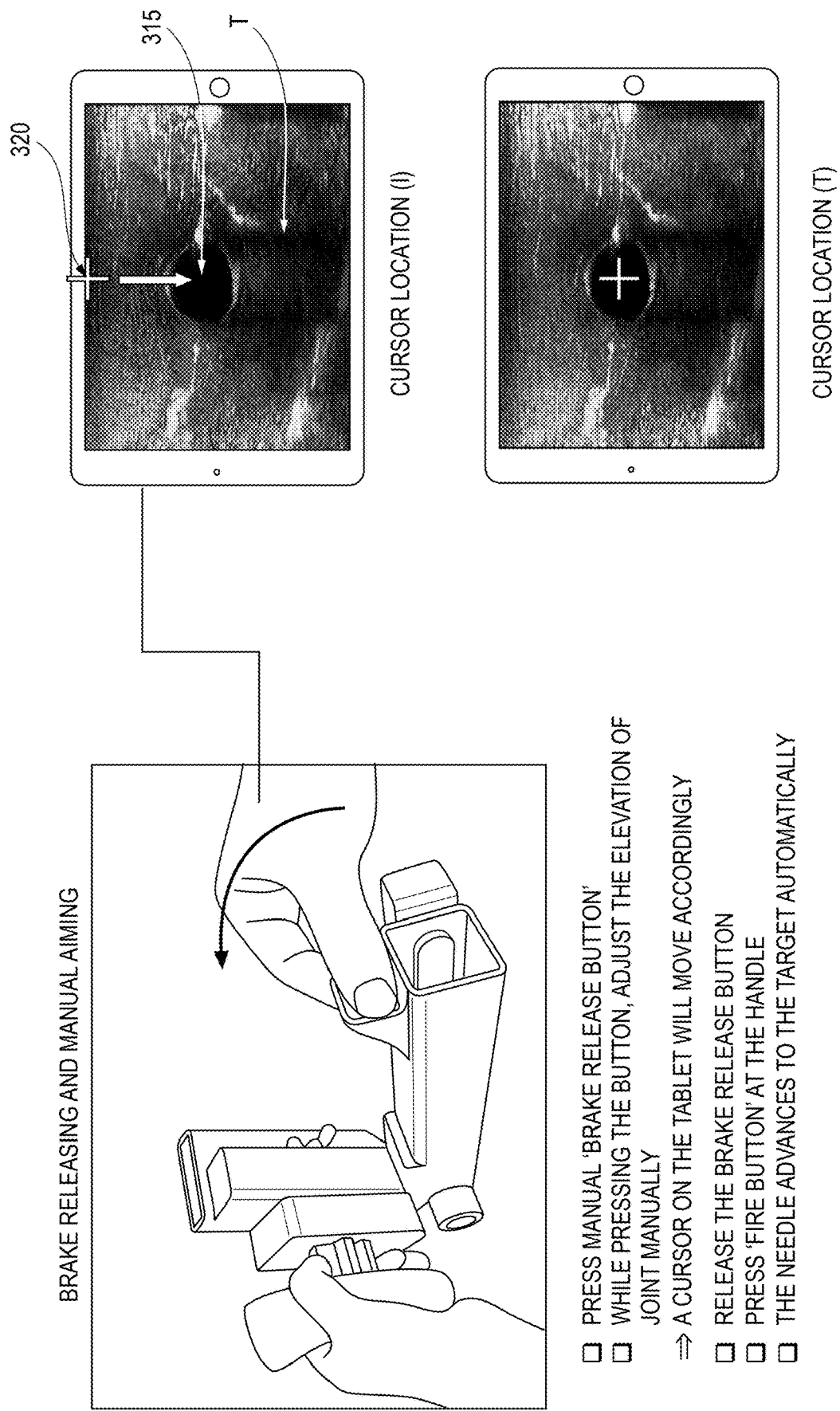

To that end, and looking now at FIG. 32, electronic device 80 may be configured to display an ultrasound image of the subcutaneous anatomy of the patient imaged by the ultrasound probe 75 in real time. Thus, electronic device 80 may be used by the clinician to visualize a desired preselected target T located within the tissue based on the calculated parameters for insertion of tissue penetrating member 180. Target T may be any point located subcutaneously within a patient, such as in a blood vessel. Identifying target T is a skill typical of many trained medical professionals in the healthcare industry. Guiding tissue penetrating member 180 to target T is the challenge, however, given the complications and risks to the patient from tissue deformation and vein rolling.

Figure 34:
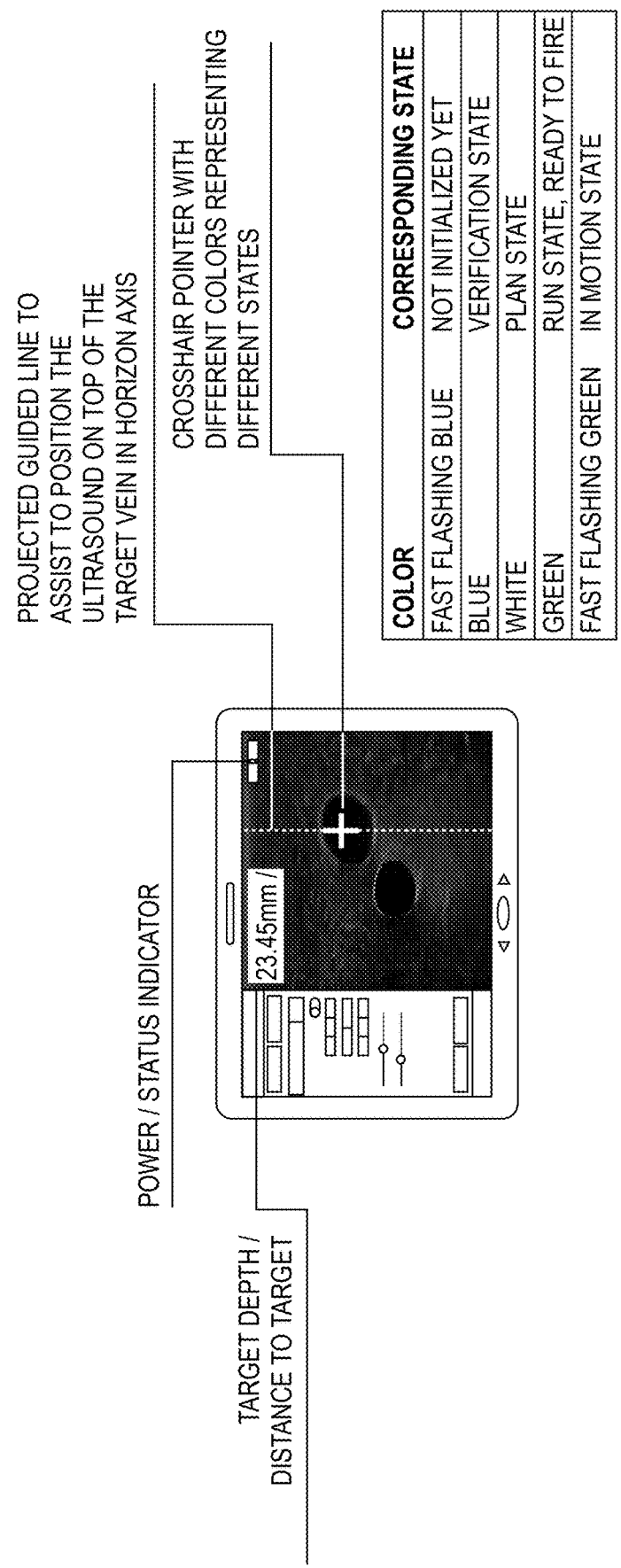
Figure 35:
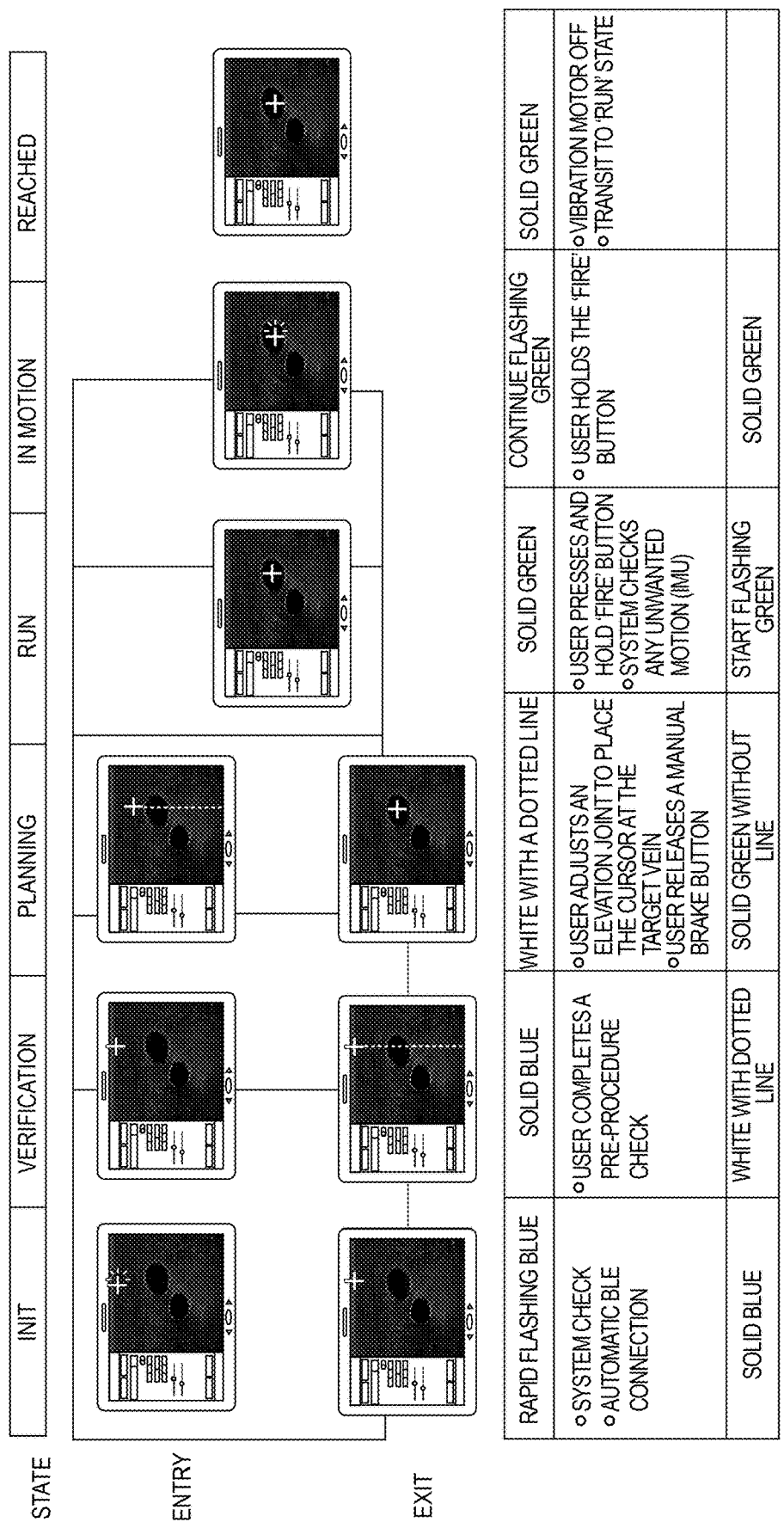
FIG. 35 illustrates exemplary screenshots of the software of FIGS. 32-34 used in concert with the novel image-guided robotic system of the present invention.

To address these issues, apparatus 5 is configured to help the clinician obtain information about a target T located subcutaneously within tissue via ultrasound using ultrasound device 20, and then permit the clinician to select a target point 315 on display 300 of electronic device 80 showing a corresponding image of the vessel. Target point 315 can be adjusted on the display 300 by the clinician (e.g., where display 300 comprises a touch screen, by interacting with the image via appropriate software running on electronic device 80), and processor 310 can automatically calculate where the pointed distal end 190 (i.e., the tip) of tissue penetrating member 180 would end up in the anatomy if deployed from its current position relative to the targeted location within the patient. In a preferred form of the invention, rotary angle sensor 72 provides positional data to processor 310 to indicate the angular disposition of linear actuator 10 relative to ultrasound device 20. The data provided by rotary angle sensor 72 is used by appropriate software to display a cursor 320 (e.g., a crosshair) on display 300 of electronic device 80 (i.e., with cursor 320 being superimposed over the imaged anatomy shown on display 300). See FIGS. 33-35. By moving apparatus 5 and/or by selectively adjusting the angular disposition of linear actuator 10 relative to ultrasound device 20, the clinician causes cursor 320 to move on display 300. As a result, the clinician can selectively move apparatus 5 and adjust the angular disposition of linear actuator 10 relative to ultrasound device 20 such that cursor 320 is appropriately aligned with the target anatomy (e.g., a blood vessel).

Once the desired position is achieved (i.e., once cursor 320 is aligned with target T, apparatus 5 may be actuated (e.g., via the clinician actuating control elements 105 of grip 95) so as to deploy the tissue penetrating member 180, whereby to move tissue penetrating member 180 distally such that it advances a predetermined distance. It will be appreciated that processor 310 is preferably configured to instruct apparatus 5 (i.e., linear actuator 10 of apparatus 5) to automatically stop distal movement of tissue penetrating member 180 once pointed distal tip 190 of tissue penetrating member 180 reaches the preselected target point 315 within target T so that it does not go past the target point 315. Processor 310 may also provide instructions to a vibrational actuator 270 of vibrator 265 to initiate and induce vibrating (e.g., reciprocating) motion to tissue penetrating member 180 during deployment so as to overcome the tissue deformation and vein rolling complications typically encountered in needle insertion into tissue.

Figure 36:
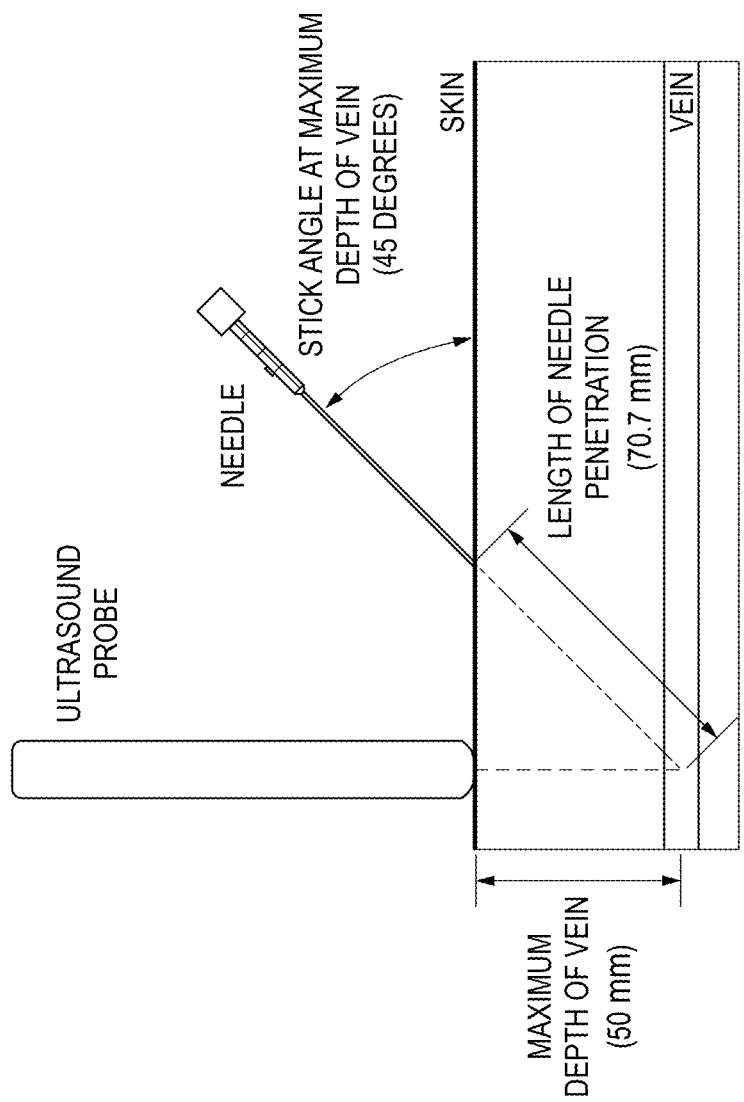
FIG. 36 is a schematic view showing how the novel image-guided robotic system of the present invention is used to access a target structure located beneath the skin of a patient.
Figure 37:
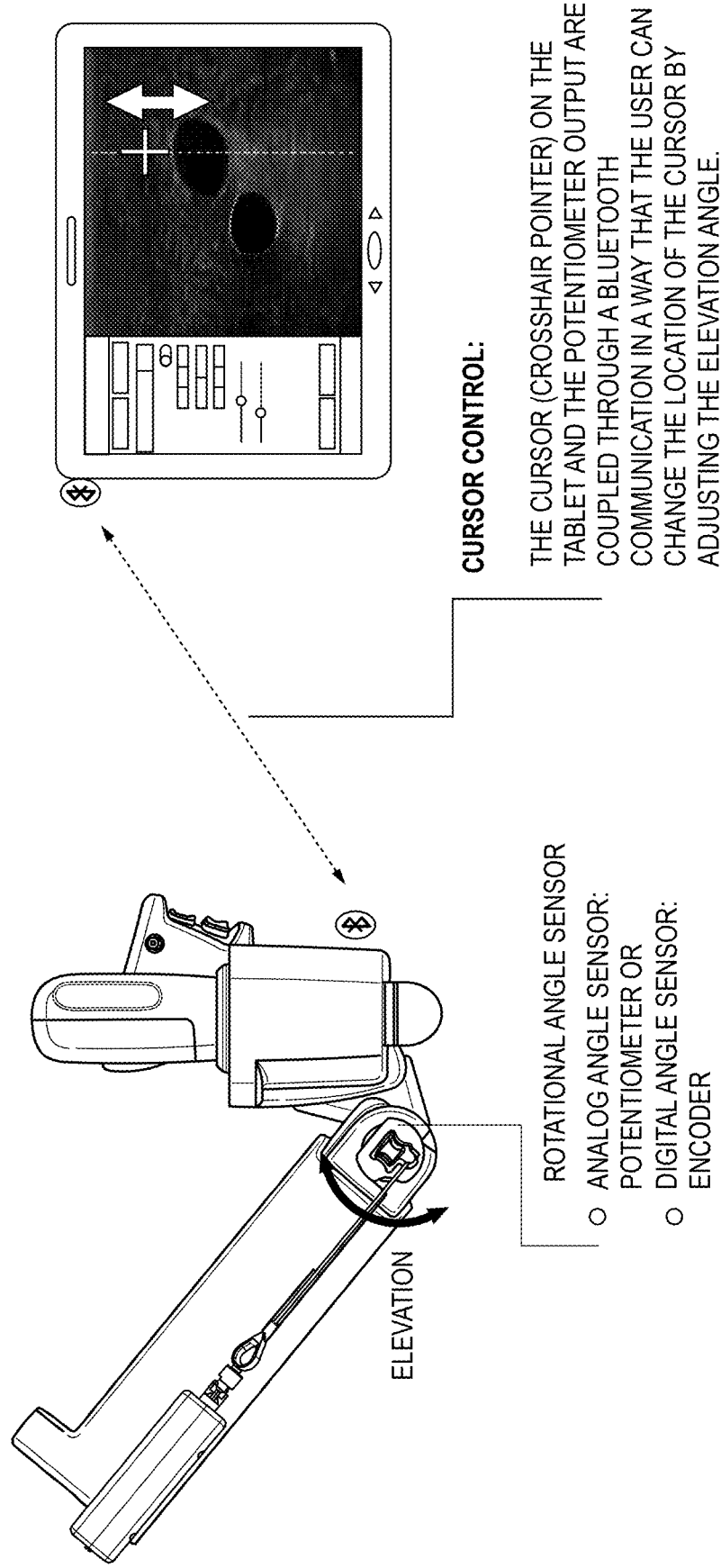
FIGS. 37 and 38 are schematic views showing novel software which can be used when adjusting the position of the novel image-guided robotic arm of the present invention.

By way of example but not limitation, and looking now at FIG. 36, ultrasound device 20 may be used to determine the distance $D_p$ from the tip of ultrasound probe 75 (i.e., the surface of the patient's skin, which is contacted by ultrasound probe 75) to the target hollow structure T located beneath the surface of the patient's skin. Rotary angle sensor 72 provides data concerning the angle of tissue penetrating member 180 relative to ultrasound probe 75. It will be appreciated that the clinician can selectively adjust the angle of linear actuator 10 relative to ultrasound device 20, and that rotary angle sensor 72 will provide data to processor 310 that permits calculation of the angle of linear actuator 10 relative to ultrasound device such that target point 315 moves in an appropriate manner on the ultrasound image provided on display 300 in real time relative to target T. See FIG. 37.

Figure 38:
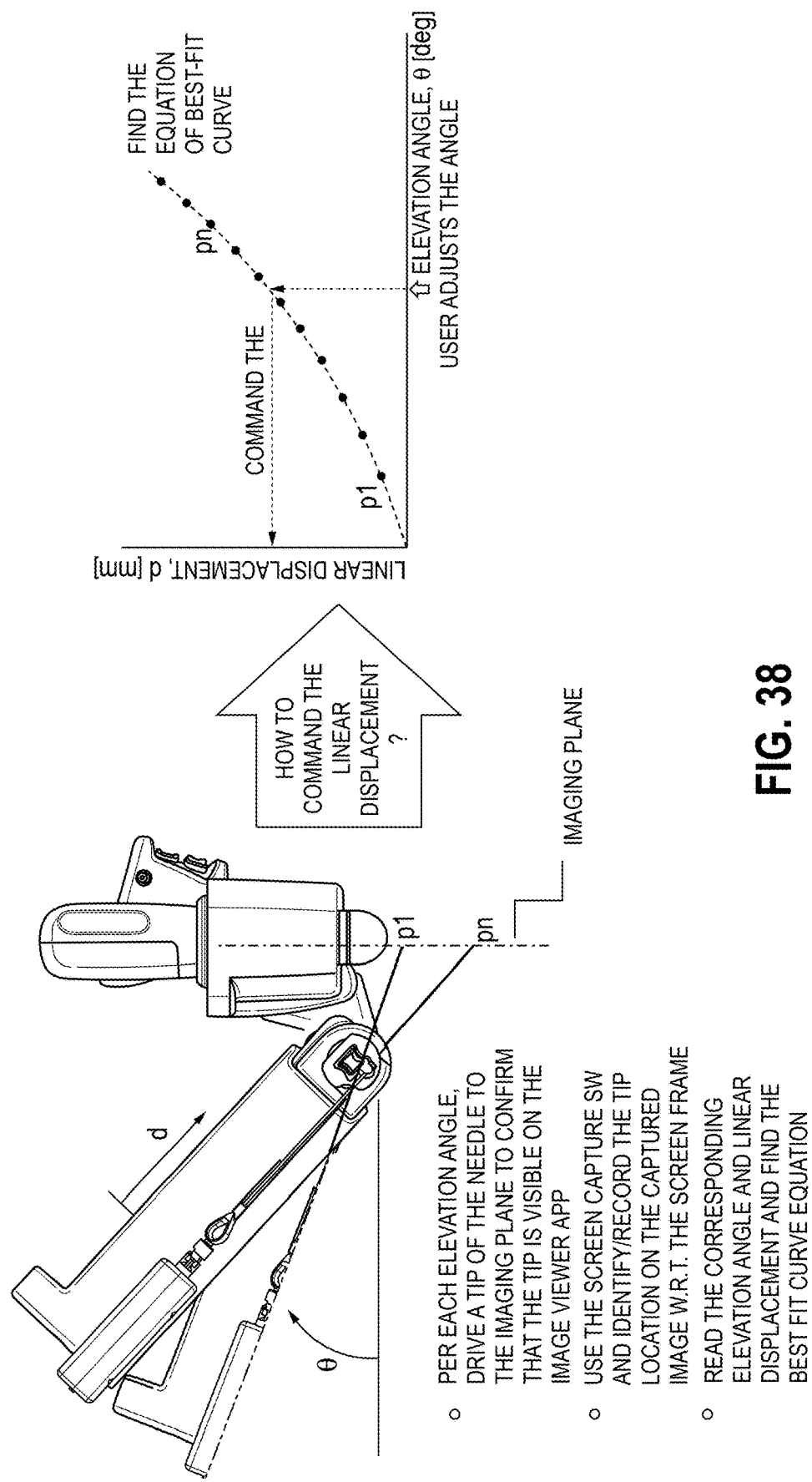

Processor 310 can then calculate the distance $D_N$ (FIG. 36) that tissue penetrating member 180 needs to be advanced distally in order to intersect target T (without passing through target T) such that pointed distal end 190 of tissue penetrating member 180 is disposed at target point 315 within a lumen of target T. By way of example but not limitation, processor 310 can calculate distance $D_N$ using trigonometric functions such as those disclosed in U.S. patent application Ser. No. 16/837,675, which patent application is hereby incorporated herein by reference. Alternatively and/or additionally, because the imaging plane is known (i.e., the projection of longitudinal axis 297 from the distal tip of ultrasound probe 75 through the patient's anatomy to the target T), and since the distance $D_N$ to be traversed by tissue penetrating member 180 along longitudinal axis 296 is a function of the angle of linear actuator 10 relative to ultrasound device 20, processor 310 may use a predetermined best-fit curve to determine the distance D that needle carriage 40 (and hence, tissue penetrating member 180 mounted thereto) is to be advanced. See, for example, FIG. 38, which shows a best-fit curve that can be pre-stored in memory so as to link the distance $D_N$ (i.e., "Linear displacement, d" in FIG. 38) that needle carriage 40 is to be moved to the angle of linear actuator 10 relative to ultrasound device 20 (i.e., "Elevation angle $\theta$" in FIG. 38). With this form of the invention, rotary angle sensor 72 provides the data indicating the angle of linear actuator 10 relative to ultrasound device 20 (i.e., "Elevation angle $\theta$" in FIG. 38), and processor 310 can use a stored best-fit curve to determine the appropriate distance $D_N$ (i.e., "Linear displacement, d" in FIG. 38) that needle carriage 40 is to be moved.

Once the clinician has selected the appropriate angle for linear actuator 10 to be disposed relative to ultrasound device 20, and once processor 310 has calculated the appropriate distance $D_N$ for tissue penetrating member 180 to be advanced distally so as to intersect target T, the clinician can initiate distal movement of tissue penetrating member 180 by pressing (and, if desired, by holding) an appropriate control element 105 disposed in grip 95.

Figure 39:
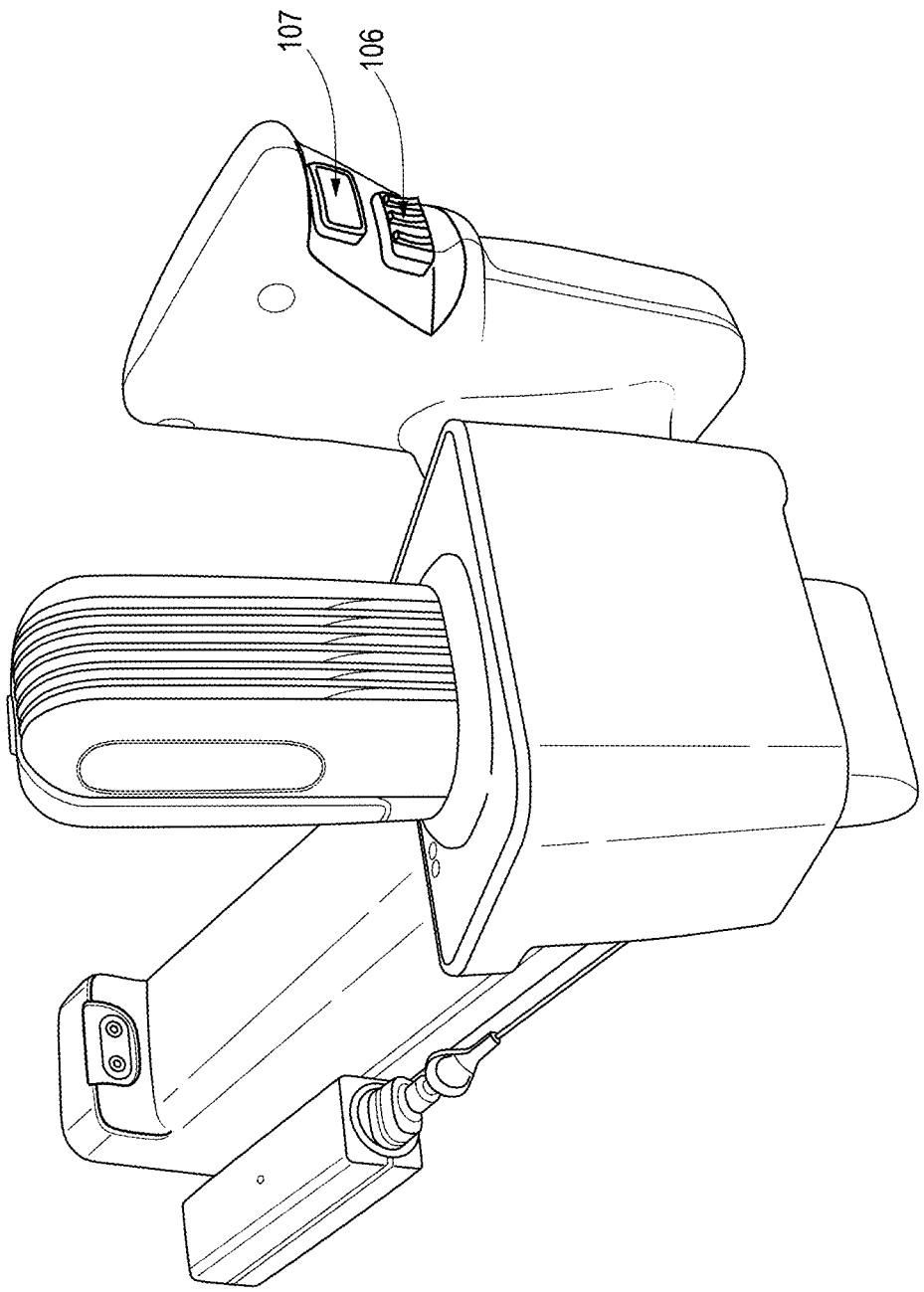
FIG. 39 is a schematic view showing further aspects of the novel image-guided robotic system of the present invention.

To this end, in one preferred form of the invention, and looking now at FIG. 39, control elements 105 preferably comprise an actuation button 106 for initiating distal movement of needle carriage 40 of linear actuator 10 (and hence, distal movement of tissue penetrating member 180 mounted thereto). When actuated, actuation button 106 causes processor 310 to actuate linear actuator motor 35, whereby to move needle carriage 40 (and hence, tissue penetrating member 180 mounted thereto) distance $D_N$ such that pointed distal end 190 of tissue penetrating member 180 is disposed within a lumen of target T and halts at target point 315. In a preferred form of the invention, processor 310 is configured to continue actuation of linear actuator motor 35 while actuation button 106 is depressed by the clinician up until carriage 40 has moved distance $D_N$. However, if desired, processor 310 can be configured to automatically move carriage 40 distance $D_N$ upon actuation of actuation button 106 without requiring actuation button 106 to be depressed by the clinician for the entire period of time that carriage 40 moves distance D. Additionally, if desired, grip 95 may comprise a retraction button 107 configured to move carriage 40 (and hence, distal movement of tissue penetrating member 180 mounted thereto) proximally when retraction button 107 is depressed by the clinician. This permits the clinician to interrupt distal movement of carriage 40 (and hence, tissue penetrating member 180 mounted thereto) and reverse the direction of movement of tissue penetrating member 180, if desired (e.g., as may be useful in the situation in which the patient moves during the insertion of tissue penetrating member 180 and it is necessary to obtain a new alignment with target T).

Figure 40:
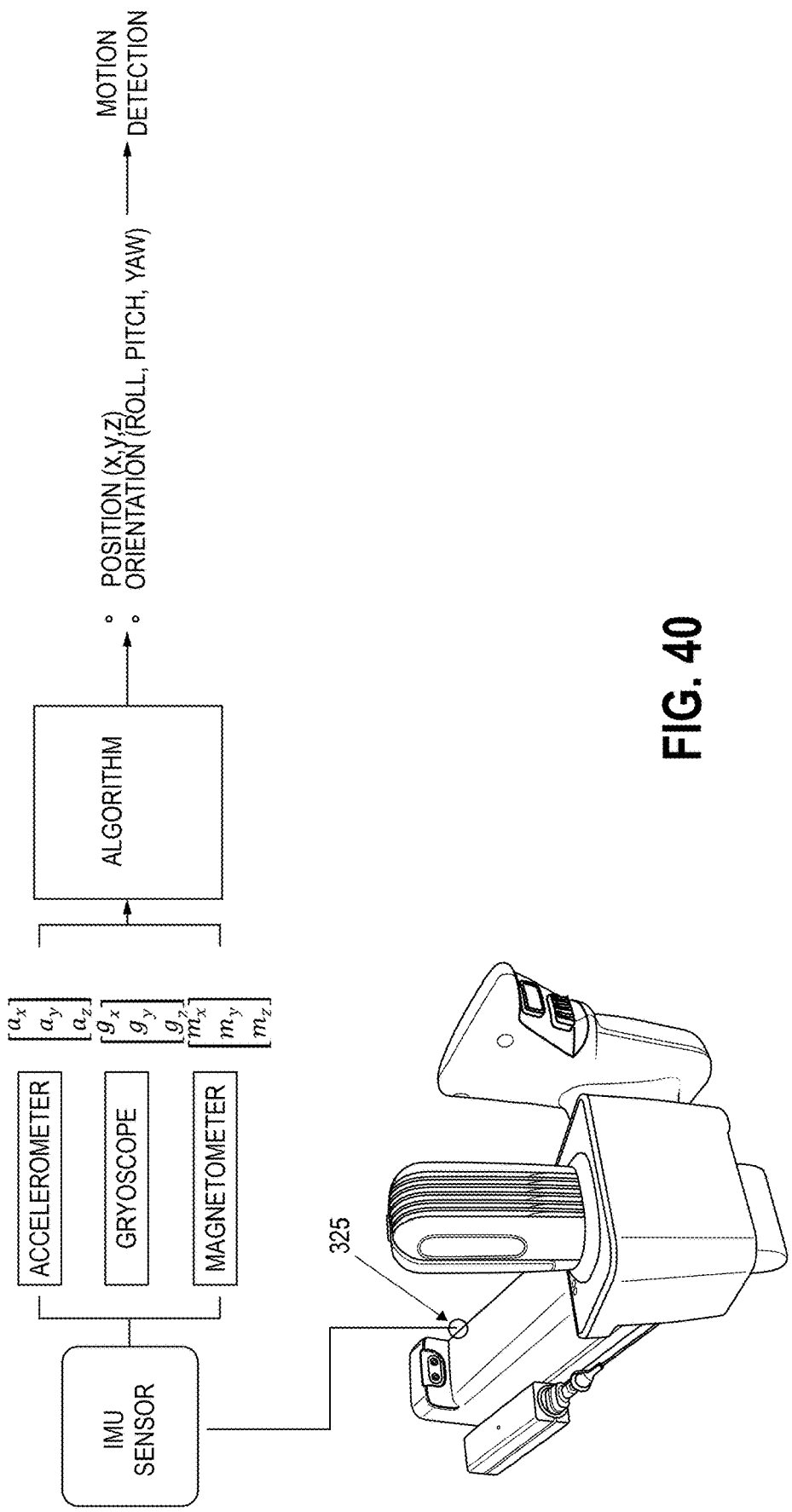
FIGS. 40 and 41 are schematic views showing how novel sensors for adjusting the positioning of the novel image-guided robotic system of the present invention.

In another form of the present invention, and looking now at FIG. 40, if desired, an Inertial Measurement Unit (IMU) sensor 325 may be provided for measuring movement of apparatus 5. By way of example but not limitation, IMU sensor 325 may comprise an accelerometer, gyroscope and/or magnetometer configured to detect movement of apparatus 5 along any one of a number of axes (e.g., pitch, yaw, roll). Detection of movement of apparatus 5 may be used by processor 310 of electronic device 80 to either move cursor 320 on display 300, i.e., in a manner consistent with movement of apparatus 5 that is measured by IMU sensor 325. Alternatively, and/or additionally, IMU sensor 325 may be used to activate a flag (e.g., an indicator shown on display 300) to indicate that apparatus 5 has been excessively moved relative to the patient and movement of tissue penetrating member 180 should be halted.

Load Sensor

If desired apparatus 5 may comprise a load sensor for measuring the force encountered by tissue penetrating member 180 as it enters the skin of the patient, whereby to provide data that may be helpful in indicating when pointed distal end 190 of tissue penetrating member 180 has entered into an internal lumen of target T and reached target point 315.

Figure 41:
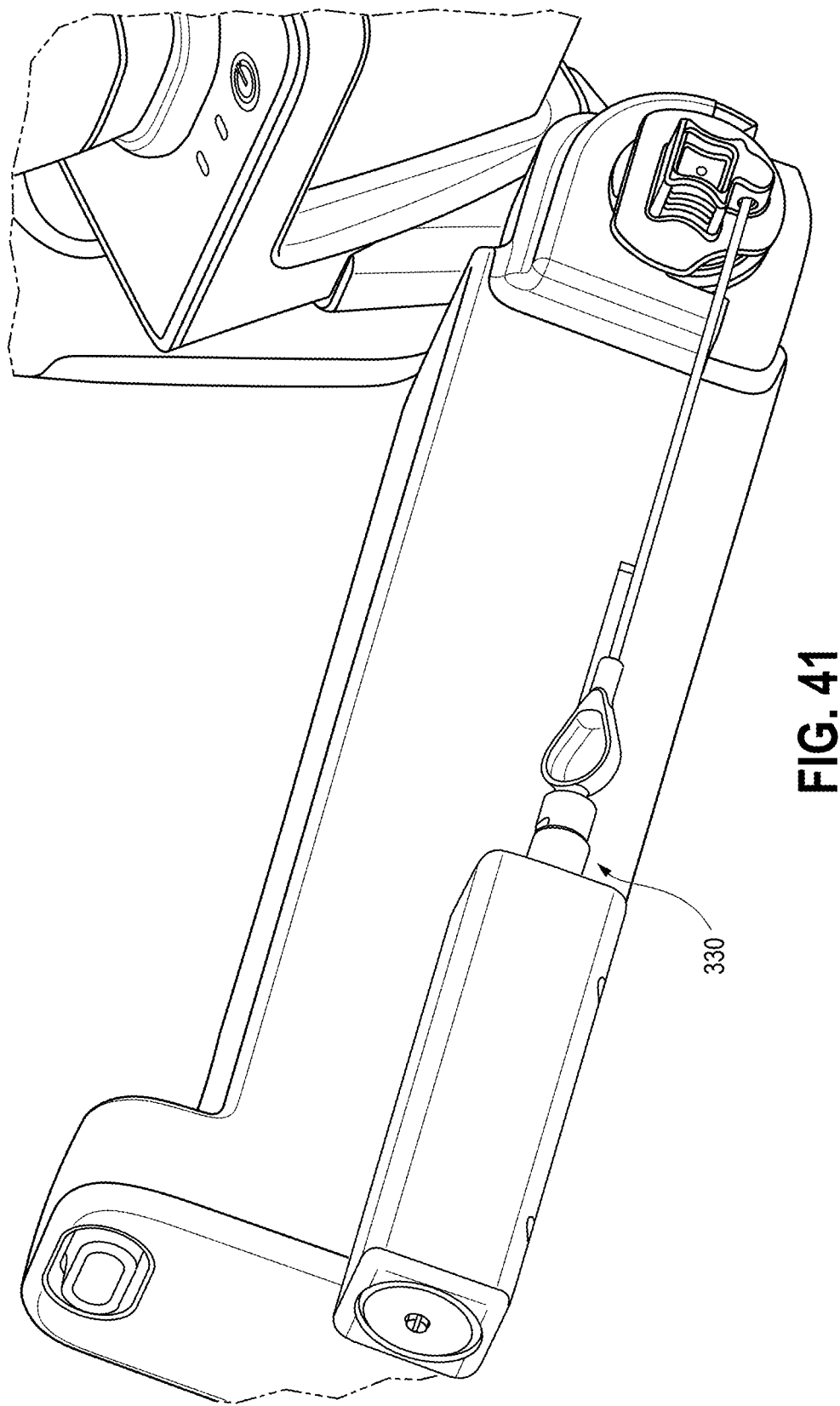
Figure 43:
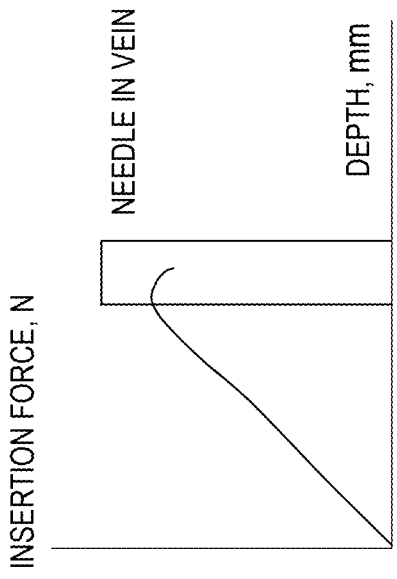
FIGS. 42 and 43 are schematic views showing the novel image-guided robotic system of the present invention used to access a body lumen located beneath the surface of the skin of a patient and the resulting drop in the insertion force as the body lumen is accessed.
Figure 42:
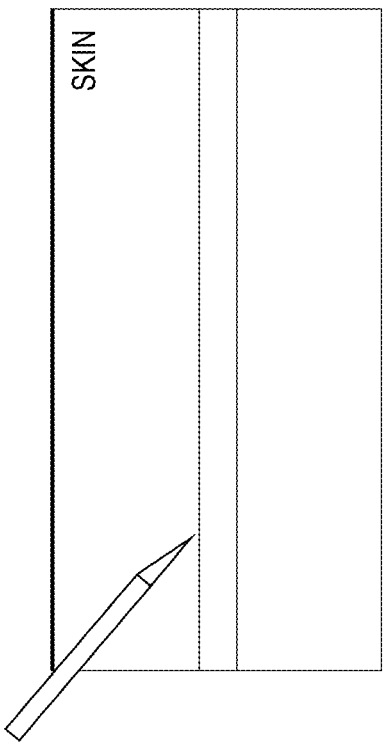

More particularly, and looking now at FIGS. 41 and 42, in this form of the present invention, a load sensor 330 is disposed in needle mount 250 of housing 6 of needle assembly 15. Alternatively (and/or additionally), if desired, load sensor 330 (and/or a second load sensor 330) may be disposed between an element of linear actuator 10 (e.g., needle carriage 40) and housing 62 of needle assembly 15, whereby to permit measuring of a proximally-directed force encountered when linear actuator 10 moves needle carriage 40 (and hence, tissue penetrating member 180 mounted thereto) distally into the tissue of the patient, as will be apparent to one of ordinary skill in the art in view of the present disclosure. Load sensor 330 is configured to measure a proximally-directed force (such as will be encountered as tissue penetrating member 180 is moved distally and encounters resistance from the tissue of the patient), which force data may then be communicated to processor 310 of electronic device 80. It will be appreciated that the tissue to be pierced by tissue penetrating member 180 will generally present a linearly-increasing proximally-directed force to penetrating member 180 as a function of needle depth until pointed distal end 190 of tissue penetrating member 180 enters into the lumen of target T and arrives at target point 315 (i.e., the internal lumen of a blood vessel). At that point, since pointed distal end 190 is disposed inside the lumen of target T, the proximally-directed insertion force will drop off slightly (see FIG. 43), which force data may be used by processor 310 to determine that pointed distal end 190 of tissue penetrating member 180 is disposed within the internal lumen of target T at target point 315 (e.g., the internal lumen of a blood vessel). At that point, processor 310 may be configured to command needle carriage 40 to halt further distal movement.

It will also be appreciated that, if desired, the current load of vibrator 265 of needle assembly motor 60 may be monitored by processor 310 of electronic device 80 in order to indirectly measure the force encountered by tissue penetrating member 180 as it enters the skin of the patient and penetrates through tissue, whereby to permit the adjustment of the vibrational frequency imparted by vibrator 265 to tissue penetrating member 180, as will hereinafter be discussed in further detail.

More particularly, it will be appreciated that as tissue penetrating member 180 encounters resistance from the tissue of the patient, additional current is needed to operate vibrator 265 so as to reciprocate tissue penetrating member 180 at the desired frequency. As processor 310 detects a rise in the current delivered to vibrator 265 as tissue penetrating member 180 is passing through the tissue of the patient, appropriate software and/or an appropriate artificial intelligence platform may be used to automatically adjust the vibrational frequency imparted by vibrator 265 to tissue penetrating member 180.

Additionally (or alternatively), if desired, the current load of linear actuator motor 35 may be monitored by processor 310 of electronic device 80 in order to indirectly measure the force encountered by tissue penetrating member 180 as tissue penetrating member 180 passes through the tissue of the patient, whereby to permit the adjustment of the speed at which tissue penetrating member 180 is distally advanced, as will also hereinafter be discussed in further detail.

More particularly, it will be appreciated that as tissue penetrating member 180 encounters resistance from the tissue of the patient, additional current is needed to continue to operate linear actuator motor 35 so as to advance tissue penetrating member 180 at the desired rate of advancement. As processor 310 detects a rise in the current delivered to linear actuator motor 35 during insertion into the tissue of the patient, appropriate software and/or an appropriate artificial intelligence platform may be used to automatically adjust the speed at which linear actuator motor 35 rotates (and hence, the speed at which tissue penetrating member 180 is advanced distally).

As a result of the foregoing, apparatus 5 is configured to make automatic real-time adjustments that facilitate smooth insertion of tissue penetrating member 180 into the patient's tissue, whereby to avoid tissue deformation or displacement (i.e., deformation or displacement of target T), as will hereinafter be discussed in further detail.

Novel Software and/or Artificial Intelligence Platform for Controlling Apparatus 5

As discussed above, when inserting tissue penetrating member 180 into the tissue of a patient such that pointed distal end 190 of tissue penetrating member 180 reaches the preselected target point 315 within target T, it is critical to avoid deflecting (e.g., passing by) or deforming (e.g., collapsing) target T.

To that end, the present invention is configured to impart vibrational energy to tissue penetrating member 180, whereby to reduce the force required to pass tissue penetrating member 180 through the tissue between the outer skin of the patient and the target point 315 within target T, which intervening tissue is sometimes hereinafter referred to as "intervening tissue" and to eliminate deformation of the intervening tissue. However, it will be appreciated that there exists significant variation in the composition of this "intervening tissue" between different patients. By way of example but not limitation, the "toughness" of the intervening tissue, varying compositions of subdermal fat or muscle, scar tissue, bone, etc., may vary from one patient to another patient. As tissue penetrating member 180 encounters resistance from the intervening tissue while being advanced distally towards target point 315, this resistance from intervening tissue can be understood as imparting some force upon target T, which force can act to deform target T (e.g., collapse the lumen of a blood vessel, making it difficult to pass pointed distal end 190 into the lumen of the blood vessel), and/or the force from intervening tissue acted upon by distal movement of tissue penetrating member 180 may cause the target T to be moved out of the path of tissue penetrating member 180 (e.g., a targeted blood vessel may be moved laterally out of the way of tissue penetrating member 180, resulting in a "miss").

To address this, as discussed above, apparatus 5 may include (i) a load sensor 330 configured to measure the proximally-directed force resulting from resistance encountered by tissue penetrating member 180 as it is advanced distally into the tissue of the patient, and/or (ii) a current monitoring scheme whereby processor 310 is configured to monitor the current load of vibrator 265 (i.e., in order to detect resistance encountered from intervening tissue), and/or (iii) a current monitoring scheme whereby processor 310 is configured to monitor the current load of linear actuator motor 35 (i.e., in order to detect resistance encountered from intervening tissue).

It will thus be appreciated that appropriate software running on electronic device 80 can be configured to utilize data from load sensor 330 and/or the current load of vibrator 265 monitored by processor 310 and/or the current load of linear actuator motor 35 monitored by processor 310 in order to adjust, in real-time, at least one of (i) the vibrational frequency imparted by vibrator 265 to tissue penetrating member 180, and/or (ii) the speed of distal advancement of tissue penetrating member 180 into the tissue of the patient.

In one preferred form of the invention, software running on electronic device 80 comprises artificial intelligence heuristics configured to permit processor 310 to make real-time adjustments to at least one of (i) the vibrational frequency imparted by vibrator 265 to tissue penetrating member 180, and/or (ii) the speed of distal advancement of tissue penetrating member 180 into the tissue of the patient in response to force changes due to intervening tissue as sensed by load sensor 330 or inferred from changes in the current load of vibrator 265 or linear actuator motor 35. As a result of this novel software/artificial intelligence paradigm, apparatus 5 can automatically adapt to variations in patient tissue composition in real-time without clinician interaction, maximizing the chances that pointed distal end 190 of tissue penetrating member 180 arrives at target point 315 within target T.

More particularly, if desired the speed of distal movement of tissue penetrating member 180 and/or the amplitude (and/or vibrational frequency) at which tissue penetrating member 180 is vibrated) can be autonomously adjusted in response to sensor data obtained during insertion of distal penetrating member 180 into tissue. As tissue penetrating member 180 is advanced distally into the tissue of the patient, load sensor 330 measures the amount of "reaction force" (i.e., the proximally-directed counterforce) encountered by tissue penetrating member 180 due to resistance to distal movement of tissue penetrating member 180 from the patient's tissue. It will be appreciated that, inasmuch as load sensor 330 may be affected by the oscillation imparted to tissue penetrating member 180 via vibrator 265, selective filtering of the wave form generated from data measured by load sensor 330 at 120-160 hertz can be used to eliminate noise introduced into the wave form by vibrator 265 from the digital signal.

In one preferred form of the invention, the nominal speed at which tissue penetrating member 180 is advanced distally into the tissue of the patient is 3.0 cm/sec, and vibrator 265 is configured to oscillate the needle axially at a frequency of 140 hertz, with an amplitude of 0.6 mm. However, it should be appreciated that, if desired, any values may be selected for the nominal speed at which tissue penetrating member 180 is advanced into tissue, the frequency of vibration imparted to tissue penetrating member 180, and/or the amplitude of vibration imparted to tissue penetrating member 180, without departing from the scope of the present invention. In the event that the reaction force exceeds 0.1 N, software running on electronic device 80 (e.g., artificial intelligence heuristics-based software) can be configured to autonomously adjust the amplitude of vibration imparted to tissue penetrating member 180 by vibrator 265. To this end, when load sensor 330 senses a reaction force exceeding a predetermined threshold (e.g., 0.1 N), the software is configured to send an appropriate signal to the vibrator 265 to modify the amplitude of vibration provided by vibrator 265 to tissue penetrating member 180 such that the amplitude of axial oscillation of tissue penetrating member 180 is increased. By way of example but not limitation, in the situation in which the nominal amplitude of vibration imparted to tissue penetrating member 180 via vibrator 265 is 0.6 mm, the amplitude would be increased 33% to 0.8 mm. If, following such an increase in the amplitude of vibration imparted to tissue penetrating member 180, the reaction force still does not drop below another predetermined threshold (e.g., 0.06 N), the software is configured to autonomously increase the amplitude of axial oscillation imparted to tissue penetrating member 180 via vibrator 265.

By way of further example but not limitation, in the situation in which the nominal amplitude of vibration imparted to tissue penetrating member 180 is initially 0.6 mm, the software may be configured to effect an additional increase in the amplitude of vibration of 25% (i.e., to 1.0 mm) when load sensor 330 senses a reaction force exceeding a predetermined threshold (e.g., 0.1 N) or where the reaction force has not dropped below another predetermined threshold (e.g., 0.06 N).

Alternatively and/or additionally, if desired, the software may be configured to increase or decrease the frequency of vibration imparted to tissue penetrating member 180 via vibrator 265 if a reaction force of less than 0.06 N is not obtained by autonomously adjusting the amplitude of the vibration imparted to tissue penetrating member 180 via vibrator 265.

Alternatively, if the reaction force remains excessively high despite autonomous adjustment of vibration amplitude by the software (e.g., in the manner discussed above), a discontinuous needle advance strategy may be automatically and autonomously used by the software. Specifically, the software may autonomously instruct linear actuator motor 35 to advance needle carriage 40 (and hence, tissue penetrating member 180 mounted thereto) distally in small increments with multiple starts and stops of distal (and proximal) motion, as will hereinafter be discussed in further detail. By way of example but not limitation, if desired, the software may comprise a mode in which the software is configured to autonomously advance tissue penetrating member 180 a predetermined distance distally (e.g., 4 mm), then withdraw tissue penetrating member 180 a predetermined distance proximally (e.g., 1 mm), repeating distal advancement, and proximal withdrawal, in this manner until target T is reached by the distal tip of tissue penetrating member 180. This "intermittent" start-and-stop motion of tissue penetrating member 180, when combined with small amplitude needle vibration at 130 hertz, further decreases the likelihood of hollow structure collapse, compression of hollow structure or bending of tissue penetrating member 180 as the hollow structure is engaged by tissue penetrating member 180. In one preferred form of the present invention, such an "intermittent" mode of discontinuous advancement of tissue penetrating member 180 is autonomously selected by the software if the force needed to achieve penetration (i.e., the force necessary to overcome the reaction force sensed by sensor 330) remains above 0.06 N after more than 1 second at 1 mm amplitude vibration of tissue penetrating member 180.

Other autonomous adjustments of vibration amplitude, vibration frequency, advancement speed of tissue penetrating member 180 and/or changes in needle advancement mode may be programmed into the software, and will be apparent to one of ordinary skill in the art in view of the present disclosure.

In another form of the invention, if desired, power consumption (i.e., "load") of the vibrator 265 and/or linear actuator motor 35 is continuously monitored by the software, inasmuch as load data can act as a "surrogate" for determining the force of penetration. If power consumption of either motor (i.e., either vibrator 265 or linear actuator motor 35) increases, such an increase would indicate that the motion (e.g., distal motion of tissue penetrating member 180) is being restricted. By way of example but not limitation, in the instance in which linear actuator motor 35 is consuming excessive power (i.e., the software detects a "high" current load), the software may autonomously adjust the speed at which tissue penetrating member 180 is advanced distally, e.g., the speed at which tissue penetrating member 180 is advanced distally may be decreased by 33%. Similarly, and by way of further example but not limitation, if the power consumption of the vibrator 265 actuator increases (i.e., the software detects a "high" current load), the software may autonomously adjust the power supplied to vibrator 265, whereby to increase the amplitude of motion of tissue penetrating member 180 by 33%.

Visual Guidance for Application of Local Anesthesia

It will be appreciated that inasmuch as tissue penetrating member 180 is to be advanced into the tissue of a patient, in some circumstances it may be desirable for the clinician to apply a local anesthetic in the area of the tissue to be penetrated by tissue penetrating member 180 in order to increase patient comfort during the procedure.

Figure 44:
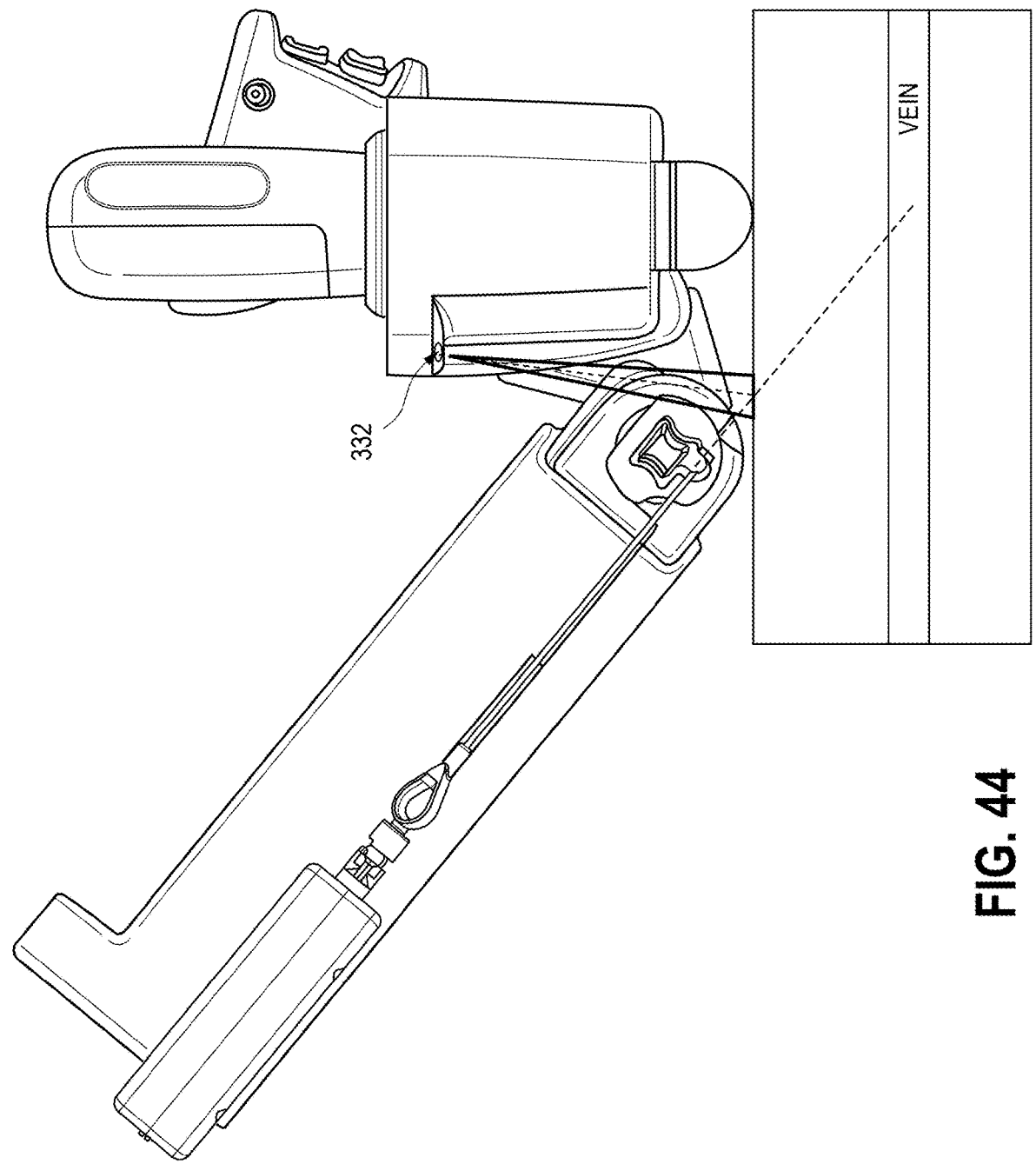
FIGS. 44-47 are schematic views showing how the novel image-guided robotic system of the present invention may be used to access a body lumen located beneath the surface of the skin of a patient, including aspects of novel visual guidance elements for use in connection with the same.
Figure 45:
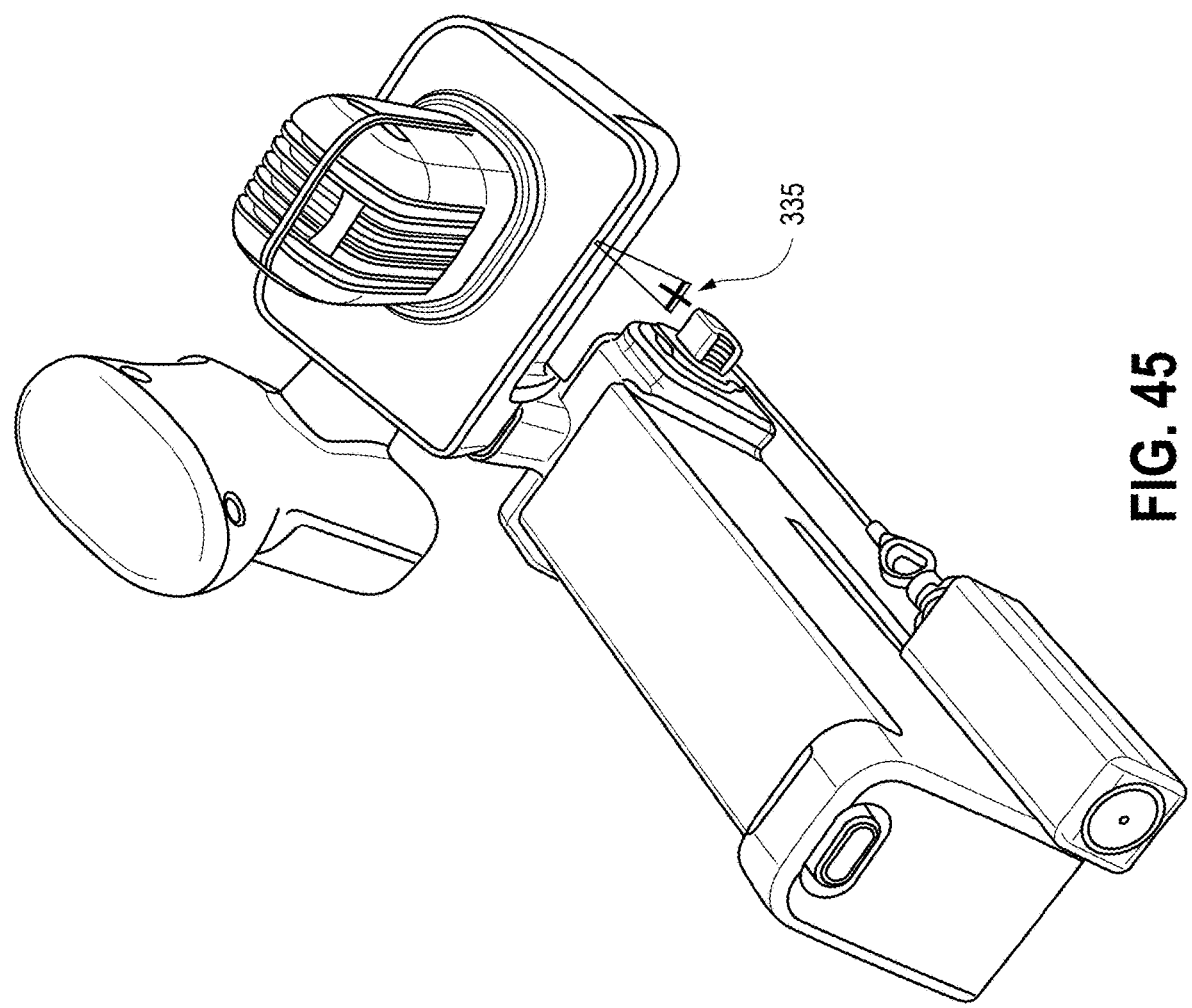

To that end, and looking now at FIGS. 44 and 45, if desired, apparatus 5 may comprise a visual guidance element 332 for projecting a beam of light 335 onto the patient's skin. Visual guidance element 332 may be any type of visual projection that is visible on the patient's skin. By way of example but not limitation, visual guidance element may be in the form of a laser projection or a micro projector. Visual guidance element 332 is preferably mounted to the exterior of ultrasound device 20 and configured to direct beam of light 335 at the location on the surface of the patient's skin where tissue penetrating member 180 will pierce the patient's skin in order to advance to target point 315 within target T. Since the location at which the patient's skin will be pierced by tissue penetrating member 180 is a function of the angle of linear actuator 10 relative to ultrasound device 20, it will be appreciated that visual guidance element 332 is configured to move in an appropriate fashion (e.g., as directed by processor 310 according to the angle measured by rotary angle sensor 72) such that the beam of light 335 projected on the patient's skin is appropriately aligned with the location to be pierced by tissue penetrating member 180 for a given angle. Beam of light 335 projected on the patient's skin by visual guidance element 330 permits the clinician to identify where to administer an appropriate anesthetic (e.g., a topical anesthetic, an injected anesthetic, etc.) coincident with the location where tissue penetrating member 180 will enter the patient's skin.

Figure 46:
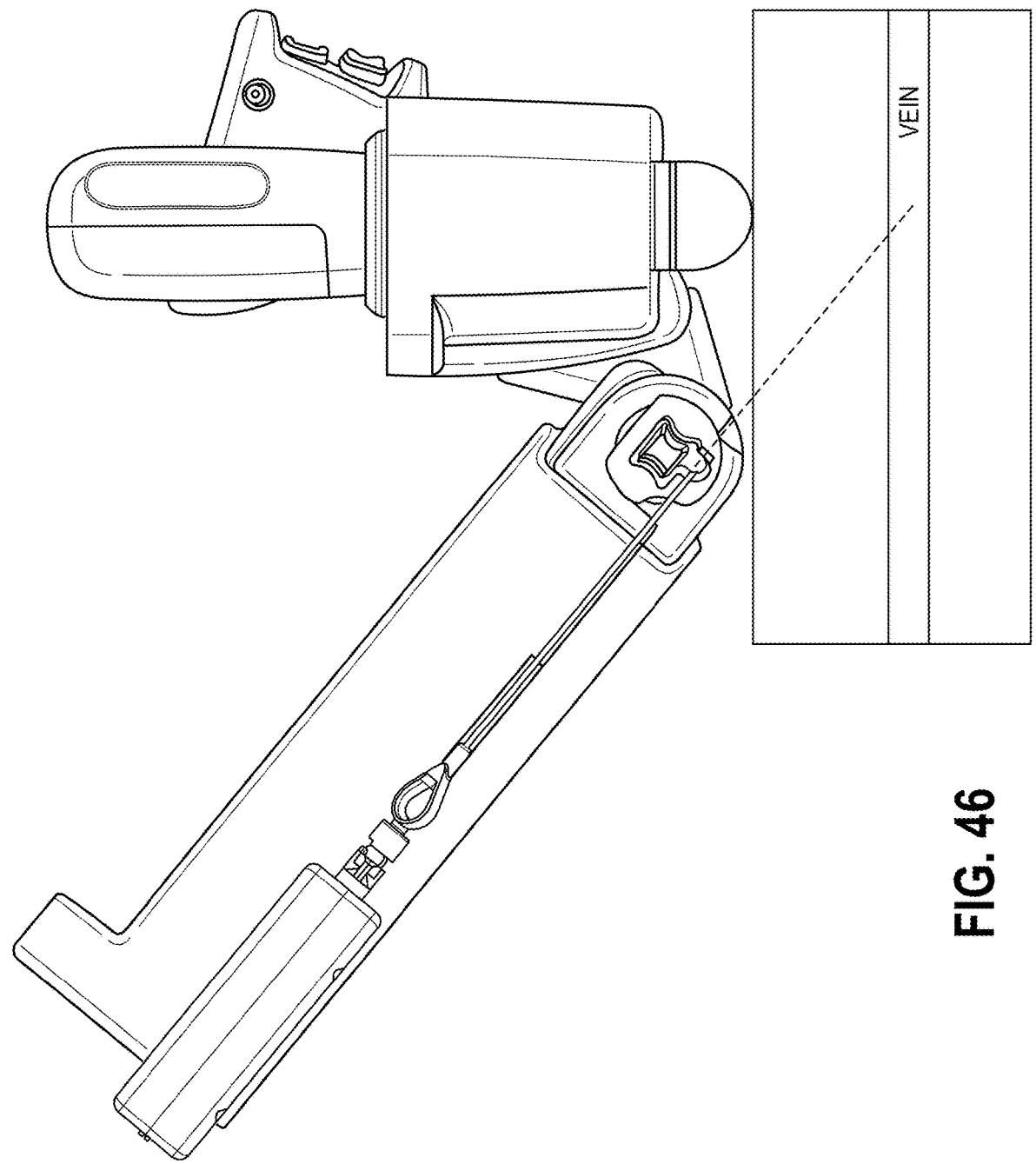
Figure 47:
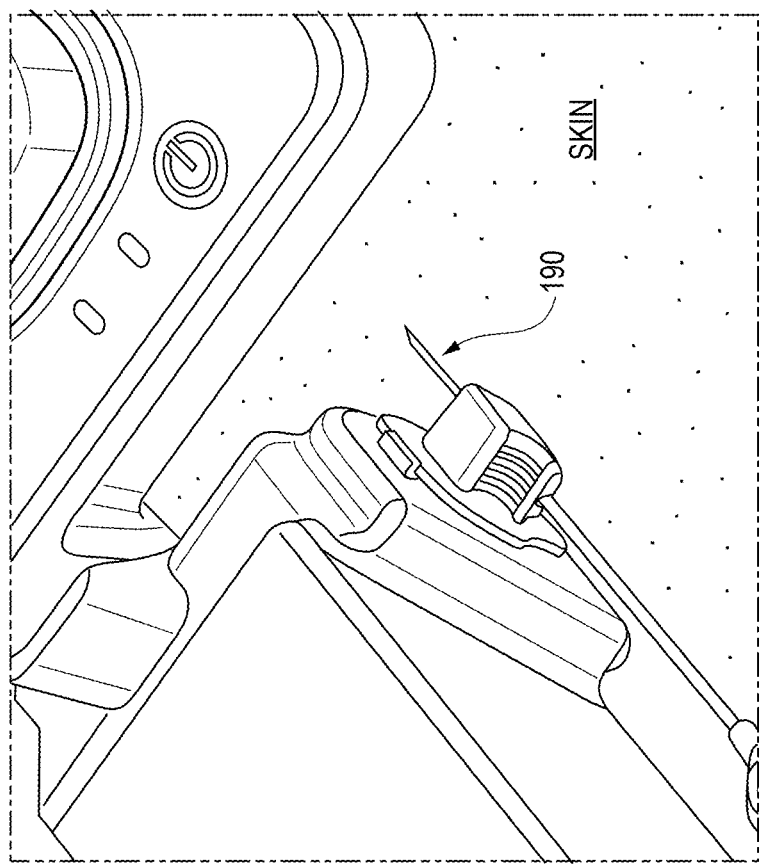
Figure 49:
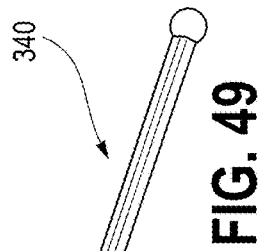
FIGS. 48-50 are schematic views showing a novel verification tool for calibrating the novel image-guided robotic system of the present invention.
Figure 50:
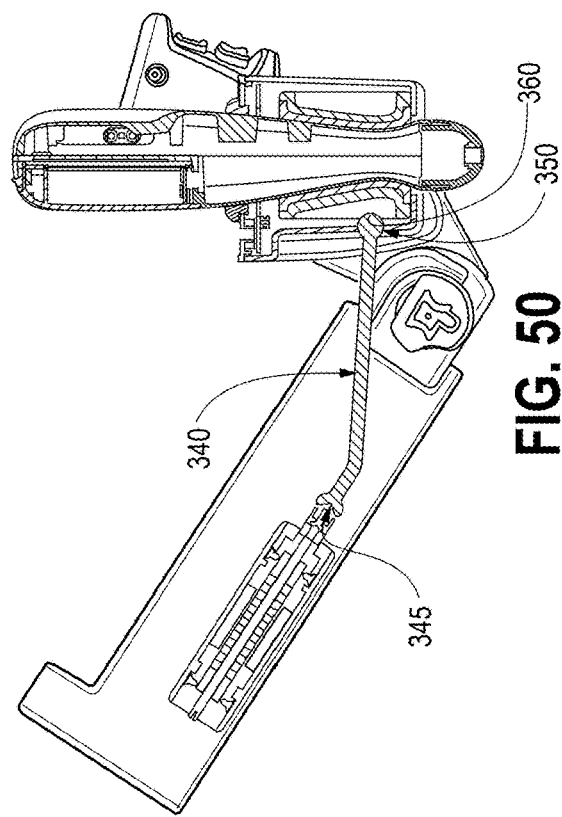
Figure 48:
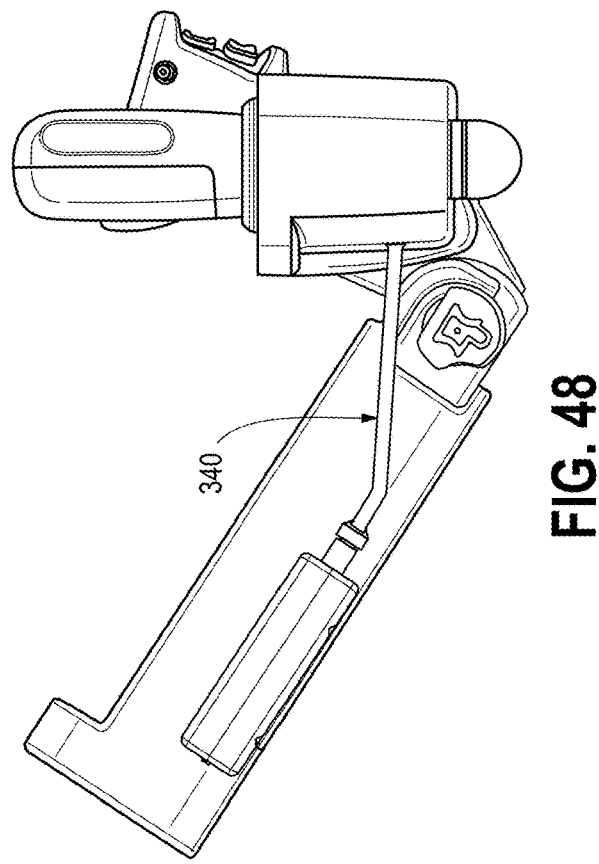

Alternatively and/or additionally, if desired, it will be appreciated that tissue penetrating member 180 may be used as a "mechanical" visual guidance element. Looking now at FIGS. 46 and 47, in this form of the invention, processor 310 instructs needle carriage 40 to move distally a predetermined distance until pointed distal end 190 of tissue penetrating member 180 is disposed just above the area of the patient's skin that is to be pierced by further distal movement of tissue penetrating member 180. With pointed distal end 190 of tissue penetrating member 180 halted just prior to entering into the skin of the patient, the clinician can visually approximate the location on the patient's skin where the needle will pierce the skin and the clinician can administer an appropriate anesthetic (e.g., a topical anesthetic, an injected anesthetic, etc.) coincident with the location where tissue penetrating member 180 will enter the patient's skin.

Pre-Procedure Calibration of Apparatus 5

It will be appreciated that since accurate measurement of the angle of linear actuator 10 relative to ultrasound device 20 is critical to achieving correspondence between alignment of target point 315 with target T such that tissue penetrating member 180 intersects with target T when apparatus 5 is actuated, it may be desirable to periodically calibrate apparatus 5 such that the angle determined by rotary angle sensor 72 is accurate.

To that end, and looking now at FIGS. 1 and 48-50, there is shown a verification tool 340. Verification tool 340 preferably comprises a proximal fiducial divot 345 and a distal ball 350 connected by an angled rod 355. Fiducial divot 345 is sized to releasably mount to needle mount 250 of housing 62 of needle assembly 15, and distal ball 350 is sized to be received in a fiducial divot 360 (FIG. 50) formed in the housing of ultrasound device 20. If desired, fiducial divot 345 and/or fiducial divot 360 may comprise one or more magnets to facilitate temporary mounting of verification tool 340, as will hereinafter be discussed in further detail. Where fiducial divot 360 comprises a magnet for releasably mounting distal ball 350, distal ball 350 comprises a ferrous metal for making magnetic attachment to fiducial divot 360.

With this form of the invention, when it is desired to calibrate apparatus 5, needle carriage 40 is moved to a pre-determined calibration position (e.g., its proximalmost position) and verification tool 340 is mounted to needle mount 250 of housing 62 of needle assembly 15 by placing fiducial divot 345 over metal ball 255 of needle mount 250. The clinician than manually adjusts the angle of linear actuator 10 relative to ultrasound device 20 by moving linear actuator 10 about rotary link 70 until distal ball 350 of verification tool 340 is received within fiducial divot 360 of ultrasound device 20. Inasmuch as the length and geometry of verification tool 340 is known with precision, it is possible to know, with precision, the angle of linear actuator 10 relative to ultrasound device 20 when verification tool 340 is so mounted. Thus, rotary angle sensor 72 can be reset at this known angle, and verification tool 340 can thereafter be removed (and apparatus 5 can be used to perform a procedure).

Figure 51:
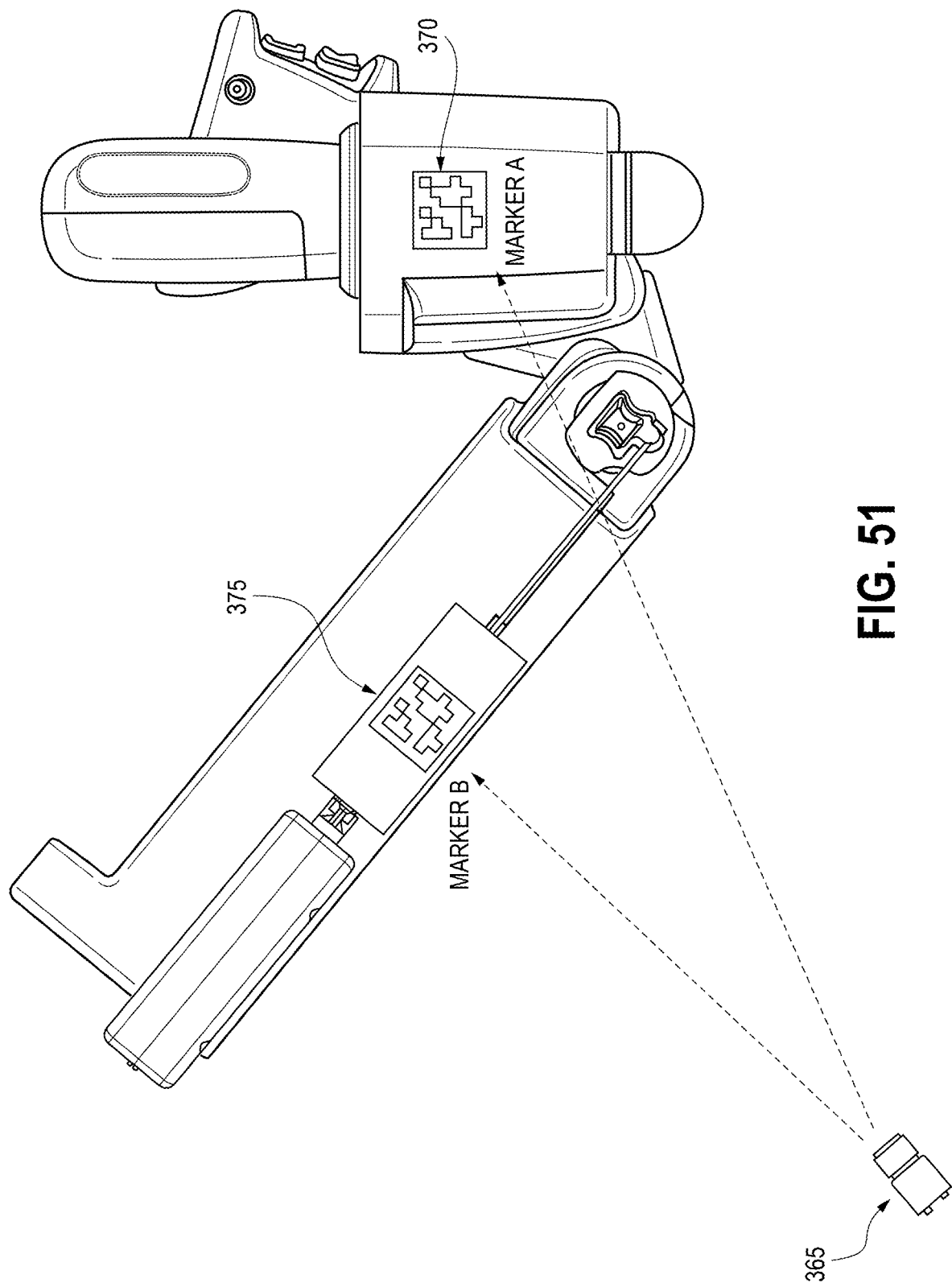
FIG. 51 is a schematic view showing a novel camera-based system for calibrating the novel image-guided robotic system of the present invention.

In another form of the invention, and looking now at FIG. 51, if desired, a camera 365 (e.g., carried by electronic device 80) may be used to calculate the distance between a first marker 370 mounted to the exterior of ultrasound device 20 and a second marker 375 mounted to the exterior of linear actuator 10. If desired, one or both of first marker 370 and second marker 375 may comprise QR codes for allowing camera 365 to lock onto and recognize the marker. Since the distance between first marker 370 and second marker 375 is known with precision for a pre-determined angle of linear actuator 10 relative to ultrasound device 20, first marker 370 and second marker 375 can be used by a clinician to calibrate apparatus 5 by moving linear actuator 10 relative to ultrasound device 20 until a pre-determined distance between first marker 370 and second marker 375 is observed by camera 365. At that point, the angle of linear actuator 10 relative to ultrasound device 20 is known with precision, and hence, rotary angle sensor 72 can be calibrated for the known angle.

Figure 52:
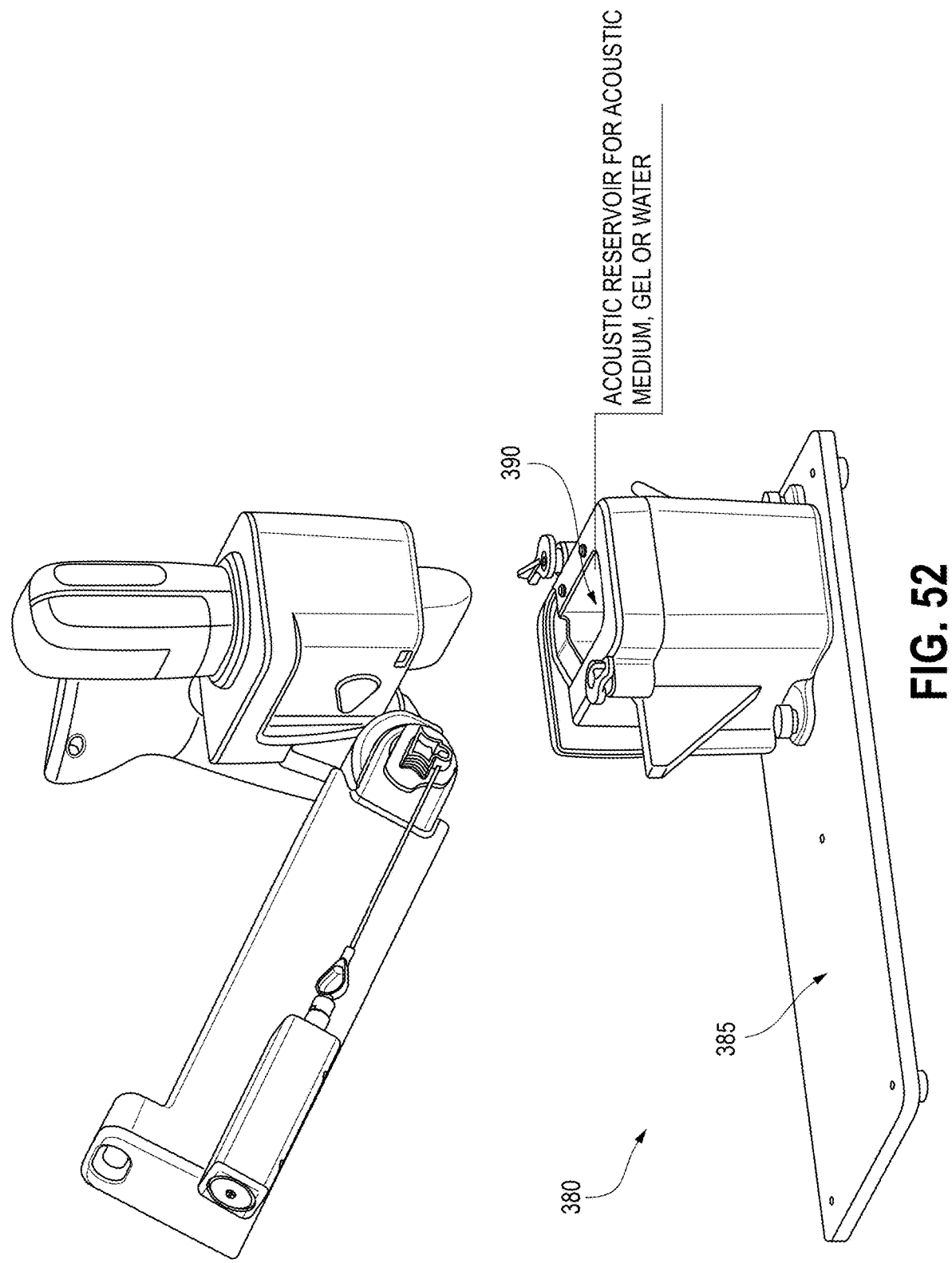
FIGS. 52 and 53 are schematic views showing a novel cradle for storing and/or calibrating the novel image-guided robotic system of the present invention.
Figure 53:
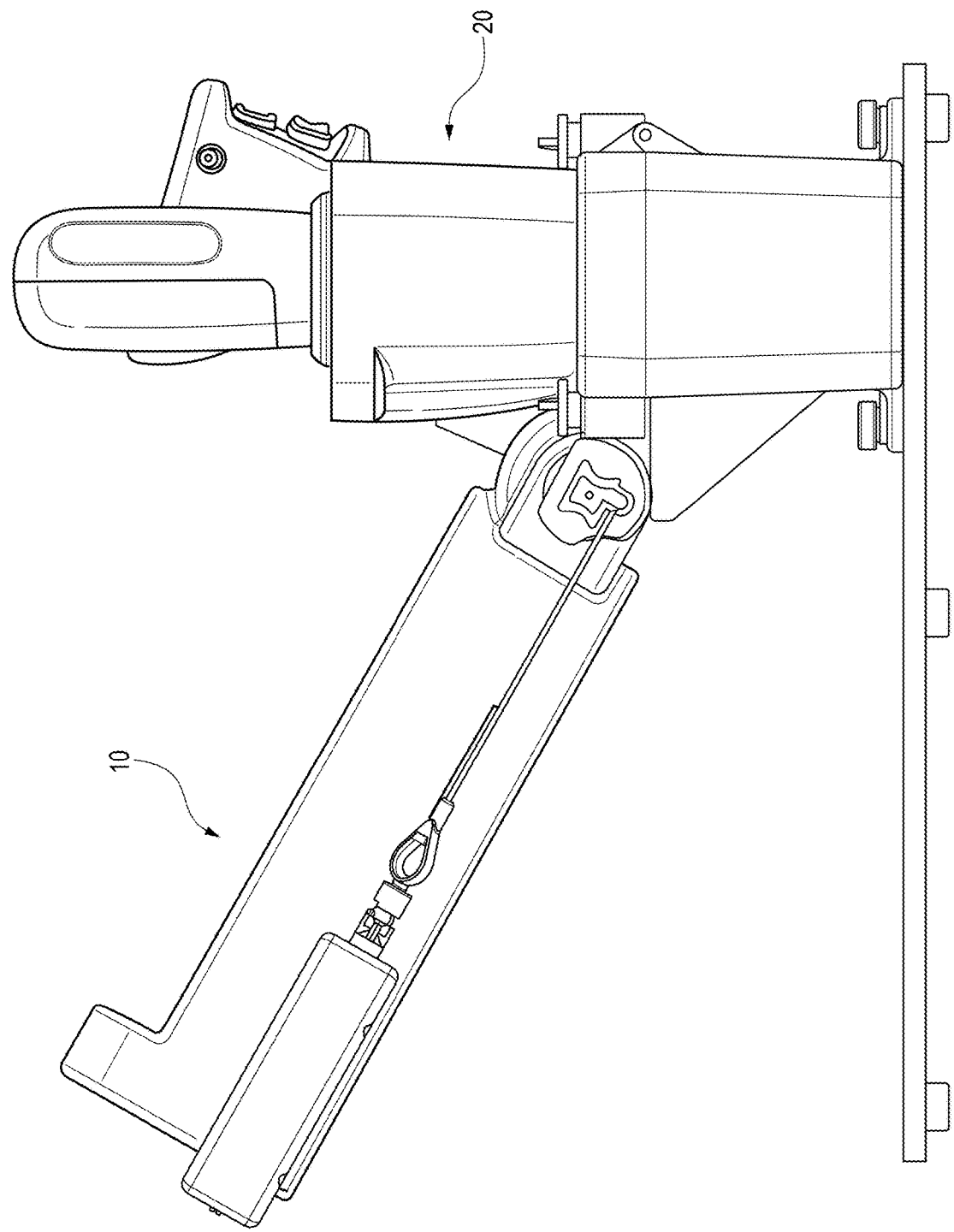

In still another form of the invention, and looking now at FIGS. 52 and 53, if desired, a calibration fixture 380 may be provided for calibrating ultrasound device 20. Calibration fixture 380 generally comprises a base 385, and an acoustic reservoir 390 mounted to base 385 and sized to receive ultrasound probe 75 therein. Acoustic reservoir 390 may be filled with an appropriate medium (e.g., ultrasound gel or water) which may be used to calibrate ultrasound probe 75 in a manner that will apparent to one of skill in the art in view of the present disclosure.

Use of Apparatus 5

As discussed above, apparatus 5 may be used by a clinician to access an internal lumen of a structure (e.g., a blood vessel) disposed beneath the surface of the skin in order to perform a medical procedure such as the installation of a central venous catheter (CVC).

More particularly, in an exemplary procedure, needle carriage 40 is moved to its proximalmost position and a needle 65 is mounted to housing 62 of needle assembly 15 by mounting magnetic mount 220 of hub 200 of needle 65 to needle mount 250 such that funnel-shaped passageway 225 can be accessed by a guidewire. The clinician then mounts needle guide 50 (carrying a surgical drape 165 mounted thereto) within needle guide seat 45 of housing 30 so that tissue penetrating member 180 of needle 65 is aligned with needle passageway 145 of needle guide 50. Surgical drape 165 is moved so that needle passageway 145 and tissue penetrating member 180 are exposed, but all other components of apparatus 5 are covered by sterile surgical drape 165.

The clinician holds apparatus 5 by grasping handle 25, and maneuvers apparatus 5 such that ultrasound probe 75 of ultrasound device 20 is disposed over the area of the skin above the structure that is to be accessed. The clinician uses display 300 of electronic device 80 to visualize the structure that is to be accessed using ultrasonography. Appropriate software running on electronic device 80 superimposes cursor 320 over the image displayed on display 300, and the clinician moves apparatus 5 until the structure to be accessed is aligned with cursor 320. It will be appreciated that where the structure to be accessed is a structure with a significant longitudinal axis (e.g., a blood vessel), the clinician can move apparatus 5 such that either the "short" axis of the structure to be accessed (FIG. 54) or the "long axis" of the structure to be accessed (FIG. 55), is visible on display 300. The "short axis" of the structure to be accessed may be visualized by moving apparatus 5 such that the imaging plane provided by ultrasound probe 75 is disposed perpendicular to the longitudinal axis of the structure to be accessed (in which case the structure will appear as a generally circular structure on display 300). The "long axis" of the structure to be accessed may be visualized by moving apparatus 5 such that the imaging plane provided by ultrasound probe 75 is disposed parallel to the longitudinal axis of the structure to be accessed (in which case the structure will appear as a generally elongated structure on display 300). It will be appreciated that one significant advantage of apparatus 5 is that the clinician can initiate the procedure regardless of whether the structure to be accessed is visualized along its short axis or its long axis.

Figure 56:
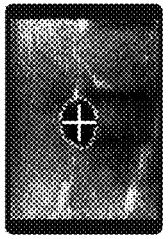
FIG. 56 illustrates exemplary uses of software for use with the novel image-guided robotic system of the present invention in order to facilitate accessing a body lumen located beneath the skin surface of a patient.

Looking now at FIG. 56, once the clinician has identified the structure to be accessed on display 300 of electronic device 80 and vertically aligned cursor 320 with the structure to be accessed on display 300, the clinician adjusts the angle of linear actuator 10 relative to ultrasound device 20 by rotating linear actuator 10 about rotary link 70, as necessary. More particularly, the clinician actuates manual brake release 55 (i.e., by pushing manual brake release 55 distally), whereby to release brake mechanism 125 and permit rotation of linear actuator 10 about rotary link 70. The clinician then rotates linear actuator 10 as desired about rotary link 70 (which rotation is measured in real time by rotary angle sensor 72), causing cursor 320 to move in a corresponding manner on display 300. Thus, by adjusting the angle of linear actuator 10 relative to ultrasound device 20, the clinician can align cursor 320 with the structure to be accessed on display 300.

Once the clinician has adjusted the angle of linear actuator 10 relative to ultrasound device 20 such that cursor 320 aligns with the structure to be accessed on display 300, the clinician releases manual brake release 55, whereby to lock brake mechanism 125 and prevent further rotation about rotary link 70. If desired, the clinician administers a local anesthetic to the patient's skin in the region that tissue penetrating member 180 is to enter the patient's skin. This may be accomplished either by utilizing a visual guidance element 330, or by mechanical means (i.e., visually approximating the area of the skin to be impacted by tissue penetrating member 180 by taking note of the position of tissue penetrating member 180 vis-à-vis the skin of the patient), in the manner discussed above.

Processor 310 of electronic device 80 calculates the distance $D_N$ to be traversed by tissue penetrating member 180 through the patient's tissue in order to intersect target point 315 (i.e., the location in three-dimensional space within the internal lumen of target T identified by cursor 320 on display 300). The clinician then holds apparatus 5 stationary, and actuates actuation button 106 of grip 95, whereby to cause linear actuator motor 35 to move needle carriage 40 (and hence, needle 65 mounted to housing 62 of needle assembly 15 mounted to needle carriage 40) distally distance $D_N$. Processor 310 causes linear actuator motor 35 to halt movement of needle carriage 40 once needle carriage 40 has moved distance $D_N$.

As discussed above, electronic device 80 may be configured to automatically adjust at least one of (i) the vibrational frequency imparted by vibrator 265 to tissue penetrating member 180, and/or (ii) the speed of distal advancement of tissue penetrating member 180 into the tissue of the patient, in response to force load changes sensed by load sensor 330 and/or the current load delivered to vibrator 265 and/or the current load delivered to linear actuator motor 35, with automatic adjustments being made in real-time by appropriate software and/or an appropriate artificial intelligence platform. Thus, apparatus 5 is able to account for variations in the composition of the intervening tissue between different patients so as to facilitate smooth insertion of tissue penetrating member 180 into the patient's tissue without moving target T out of the insertion path (or otherwise deforming target T).

At this point, pointed distal end 190 of tissue penetrating member 180 of needle 65 is disposed within the internal lumen of target T at target point 315, such that lumen 195 of tissue penetrating member 180 is in connection with the internal lumen of target T. Thus, it is now possible for the clinician to use needle 65 to access the internal lumen of target T in order to perform a procedure (e.g., installation of a CVC).

By way of example but not limitation, if the clinician wishes to install a CVC, the clinician next advances a guidewire G into teardrop-shaped cavity 205 of hub 200 of needle 65, passing the guidewire through funnel-shaped passageway 225 and distally into lumen 195 of tissue penetrating member 180, until the distal end of guidewire G exits out pointed distal end 190 of tissue penetrating member 180 and is appropriately disposed in the lumen of target T. It will be appreciated that the geometry of teardrop-shaped cavity 205 and funnel-shaped passageway 225 facilitates easy insertion of guidewire G into lumen 195 of tissue penetrating member 180. It will also be appreciated that teardrop-shaped cavity 205 at the proximal end of tissue penetrating member 180 permits the clinician to insert Guidewire G into lumen 195 of tissue penetrating member 180 using only one of the clinician's hands (while the other of the clinician's hands can still be used to hold or operate an ultrasound device, e.g., ultrasound device 20). Facilitating the single-handed insertion of Guidewire G into lumen 195 of tissue penetrating member 180 is a significant improvement over the prior art method which requires the clinician to use both hands to disconnect a syringe from a tissue penetrating member (e.g., a needle) after the tissue penetrating member has been disposed in the lumen of a blood vessel, and then insert the guidewire through the lumen of the tissue penetrating member and into the blood vessel.

Once guidewire G has been installed within the lumen of target T, needle 65 may be withdrawn from the patient's anatomy (e.g., by actuating retraction button 107 of grip 95, whereby to cause linear actuator motor 35 to move needle carriage 40, and hence needle 65 mounted thereto, proximally).

Figure 57:
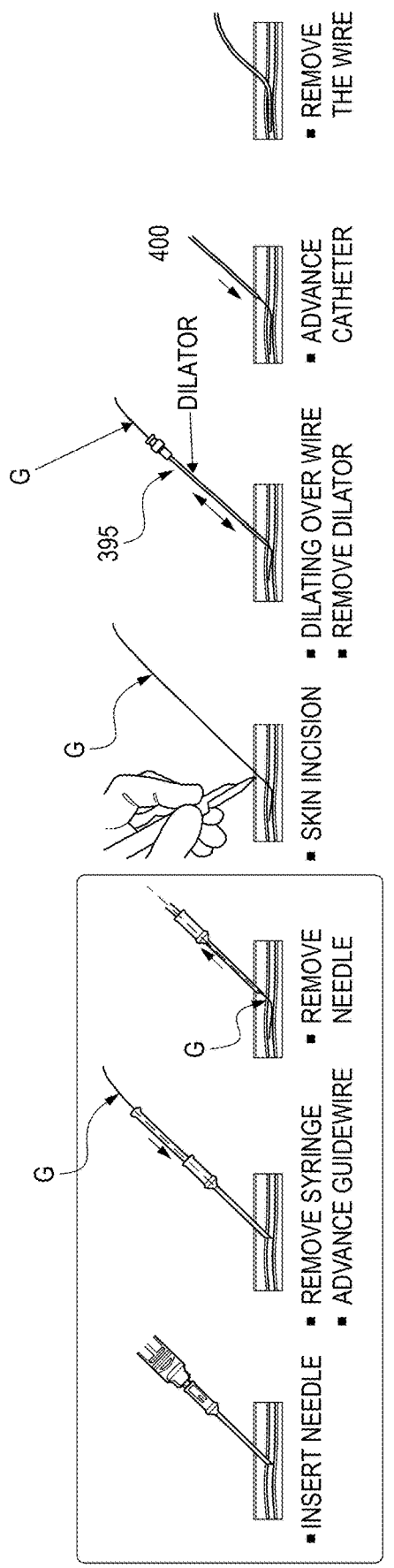
FIG. 57 illustrates how a guidewire may be inserted into a body lumen located beneath the skin surface of a patient using the novel image-guided robotic system of the present invention.

After needle 65 has been completely withdrawn from the skin of the patient, apparatus 5 may be removed and the CVC procedure completed in the traditional manner. By way of example but not limitation, once apparatus 5 has been removed (leaving guidewire G in place and extending into the lumen of the target T), the clinician may make a small incision in the skin proximate to guidewire G (i.e., in order to permit a larger-bore medical element to be inserted over guidewire G. One or more tissue dilators 395 (FIG. 57) may be passed over guidewire G so as to increase the diameter of the tunnel through the patient's tissue and into the lumen of target T. A catheter 400 may then be installed over guidewire G such that the catheter extends into, and is fluidically connected with, the internal lumen of target T. Finally, guidewire G is removed, leaving only catheter 400 installed in the patient and available for medical treatment, as desired.

In another exemplary method of using apparatus, 5, needle 65 can be used to advance substantially any surgical instrument into a body lumen of a patient (e.g., a blood vessel) using the novel apparatus of the present invention and/or needle 65 may be replaced by substantially any surgical instrument that it is desired to advance into a body lumen of a patient (e.g., a blood vessel) using the novel apparatus of the present invention. By way of example but not limitation, such alternative surgical instruments may include a biopsy device, a therapeutic (e.g., drug) delivery device, a neurostimulation electrode, a sheath needle, etc., and such alternative surgical instruments may be magnetically mounted to needle mount 250 of needle assembly housing 62 in substantially the same manner as needle 65 without departing from the scope of the present invention.

In another exemplary method of using apparatus 5, apparatus 5 can be used to insert a hollow needle (e.g., tissue penetrating member 180) into other hollow and non-hollow structures within the anatomy (e.g., into any body lumen or body cavity or solid structure such as a tumor or a nerve). By way of example but not limitation, apparatus 5 could be used to insert a hollow needle (e.g., tissue penetrating member 180) into a body lumen, body cavity or solid structure to perform a biopsy, for oblation, to inject a nerve block, etc. Furthermore, apparatus 5 could be used to insert a hollow needle (e.g., tissue penetrating member 180) into a fluid-filled body lumen, body cavity or solid structure for draining fluid from the fluid-filled body cavity, body lumen or solid structure (e.g., a cyst in a breast, a deep abscess, amniotic fluid within the uterus, the bladder, fluid from the lung, fluid from the pericardial cavity around the heart, fluid from the perineal cavity around the abdomen, cerebrospinal fluid around the spinal cord or brain, hydronephrosis in the kidney, etc.) and/or injecting fluid into a body lumen, body cavity or solid structure (e.g., oncologic drugs, epidural, etc.).

MODIFICATIONS

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An image-guided robotic system for advancing a penetrating member into a body lumen located beneath a skin surface of a patient, the image-guided robotic system comprising:
   a detector for obtaining data representative of a location of the body lumen beneath the skin surface of the patient;
   a robotic arm comprising:
      a penetrating member;
      a linear actuator for linearly advancing the penetrating member into the body lumen;
      a vibrational actuator for vibrating the penetrating member at a selected frequency;
   a processor in communication with the detector, the linear actuator and the vibrational actuator, the processor being configured to:
      (i) receive the data representative of the location of the body lumen from the detector;
      (ii) calculate the distance to a preselected target point within the body lumen;
      (iii) transmit linear advancement instructions to the linear actuator to linearly advance the penetrating member through the skin surface, through tissue between the skin surface and the body lumen and into the preselected target point within the body lumen, wherein the linear advancement instructions comprise the speed and distance required for the linear actuator to advance the penetrating member through the skin surface, through tissue between the skin surface and the body lumen and into the body lumen at the preselected target point within the body lumen;
      (iv) transmit vibrational instructions to the vibrational actuator to vibrate the penetrating member; and
      (v) automatically modify at least one of the linear advancement instructions and the vibrational instructions in order to account for resistance encountered by the penetrating member during advancement of the penetrating member through the skin surface, through the tissue between the skin surface and the body lumen and into the preselected target point within the body lumen, wherein at least one of the linear advancement instructions and the vibrational instructions is modified to mitigate deformation of the body lumen as the penetrating member advances through the skin surface, through tissue between the skin surface and the body lumen and into the preselected target point within the body lumen.

2. The image-guided robotic system of claim 1 wherein mitigating deformation of the body lumen comprises reducing the force required to advance the penetrating member into the body lumen.

3. The image-guided robotic system of claim 1 wherein mitigating deformation of the body lumen comprises mitigating at least one from the group consisting of:
   movement of the body lumen from its original position as the penetrating member passes through the skin surface, through the tissue between the skin surface and the body lumen and into the preselected target point within the body lumen;
   rolling of the body lumen as the penetrating member engages the body lumen; and
   collapse of the body lumen as the penetrating member engages the body lumen.

4. The image-guided robotic system of claim 1 wherein at least one of the speed of distal advancement of the penetrating member and the vibration imparted on the penetrating member are adjusted to mitigate deformation of the body lumen as the penetrating member advances.

5. The image-guided robotic system of claim 1 wherein the linear actuator comprises a force load sensor for sensing the force load on the penetrating member.

6. The image-guided robotic system of claim 1 wherein the linear actuator comprises a current load sensor.

7. The image-guided robotic system of claim 1 wherein the vibrational actuator comprises a current load sensor.

8. The image-guided robotic system of claim 1 wherein the processor is further configured to stop movement of the penetrating member when the penetrating member reaches the preselected target point.

9. The image-guided robotic system of claim 1 wherein the angular disposition of the penetrating member relative to the skin surface of the patient is adjustable.

10. The image-guided robotic system of claim 1 wherein the penetrating member is mounted to the robotic arm with a magnetic connection.

11. The image-guided robotic system of claim 1 wherein the penetrating member comprises a funnel-shaped guide for guiding an instrument through the penetrating member.

12. The image-guided robotic system of claim 1 wherein the robotic arm comprises a needle guide for preventing the penetrating member from bending as the penetrating member penetrates through the skin of the patient.

13. The image-guided robotic system of claim 1 further comprising a drape for covering the robotic arm.

14. The image-guided robotic system of claim 13 wherein the drape is mounted to the robotic arm so that the penetrating member is disposed outside of the drape.

15. The image-guided robotic system of claim 1 further comprising a display configured to present the image data representative of the location of the body lumen.

16. The image-guided robotic system of claim 15 wherein the display is further configured to present a visual representation of the preselected target point within the body lumen.

17. The image-guided robotic system of claim 16 wherein the display is interactive and the visual representation of the preselected target point within the body lumen can be moved on the display.

18. The image-guided robotic system of claim 1 further comprising a handle for gripping by a user.

19. The image-guided robotic system of claim 1 wherein the vibrational actuator is configured to vibrate the penetrating member at approximately 125-175 Hz.

20. The image-guided robotic system of claim 1 wherein the vibrational actuator is configured to vibrate the penetrating member with displacements up to 1 mm.

21. A method for advancing a penetrating member into a body lumen located beneath a skin surface of a patient, the method comprising:

obtaining data representative of a location of a preselected target point within the body lumen;

calculating a distance to the preselected target point within the body lumen;

advancing the penetrating member through the skin surface, through tissue between the skin surface and the body lumen and into the preselected target point within the body lumen; and vibrating the penetrating member during advancement of the penetrating member through the skin surface, through tissue between the skin surface and the body lumen and into the preselected target point within the body lumen;

wherein at least one of speed of distal advancement of the penetrating member and frequency of vibration are modified during advancement of the penetrating member through the skin surface, through tissue between the skin surface and the body lumen and into the preselected target point within the body lumen in order to mitigate deformation of the body lumen as the penetrating member advances through the skin surface, through tissue between the skin surface and the body lumen and into the preselected target point within the body lumen.

\* \* \* \* \*